US012590137B2

(12) United States Patent
Williams et al.

(10) Patent No.: US 12,590,137 B2
(45) Date of Patent: Mar. 31, 2026

(54) MEDITOPE-ENABLED T CELLS

(71) Applicant: CITY OF HOPE, Duarte, CA (US)

(72) Inventors: John C. Williams, Monrovia, CA (US);
Christine Brown, Pasadena, CA (US);
Kurt Jenkins, Duarte, CA (US);
Yi-Chiu Kuo, Duarte, CA (US);
Cheng-Fu Kuo, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 532 days.

(21) Appl. No.: 16/958,614

(22) PCT Filed: Dec. 31, 2018

(86) PCT No.: PCT/US2018/068235
§ 371 (c)(1),
(2) Date: Jun. 26, 2020

(87) PCT Pub. No.: WO2019/134001
PCT Pub. Date: Jul. 4, 2019

(65) Prior Publication Data
US 2021/0061879 A1      Mar. 4, 2021

Related U.S. Application Data

(60) Provisional application No. 62/680,442, filed on Jun. 4, 2018, provisional application No. 62/611,924, filed on Dec. 29, 2017.

(51) Int. Cl.
| | |
|---|---|
| *C07K 14/705* | (2006.01) |
| *A61K 38/00* | (2006.01) |
| *A61K 40/11* | (2025.01) |
| *A61K 40/31* | (2025.01) |
| *A61K 40/42* | (2025.01) |
| *C07K 14/725* | (2006.01) |
| *C07K 16/28* | (2006.01) |
| *C12N 5/0783* | (2010.01) |
| *C12N 15/86* | (2006.01) |

(52) U.S. Cl.
CPC ........ *C07K 14/70521* (2013.01); *A61K 40/11* (2025.01); *A61K 40/31* (2025.01); *A61K 40/4205* (2025.01); *C07K 14/7051* (2013.01); *C07K 16/2878* (2013.01); *C12N 5/0636* (2013.01); *C12N 15/86* (2013.01); *A61K 38/00* (2013.01); *A61K 2239/31* (2023.05); *A61K 2239/59* (2023.05); *C07K 2317/31* (2013.01); *C07K 2317/526* (2013.01)

(58) Field of Classification Search
CPC ................ A61K 40/31; A61K 2239/28; A61K 2239/10; A61K 2239/11; A61K 2239/15
See application file for complete search history.

(56) References Cited

U.S. PATENT DOCUMENTS

| | | | | |
|---|---|---|---|---|
| 2003/0105000 A1* | 6/2003 | Pero | ...................... | C07K 1/047 |
| | | | | 514/19.3 |
| 2012/0301400 A1* | 11/2012 | Williams | ........... | A61K 47/6811 |
| | | | | 424/139.1 |
| 2015/0038684 A1* | 2/2015 | Jensen | ................. | C12N 5/0636 |
| | | | | 530/391.9 |
| 2016/0311907 A1* | 10/2016 | Brogdon | ............ | C07K 14/7051 |
| 2017/0226223 A1* | 8/2017 | Williams | ......... | C07K 14/70521 |

FOREIGN PATENT DOCUMENTS

| | | | | |
|---|---|---|---|---|
| WO | WO-2016040441 A1 * | 3/2016 | ............. | A61K 35/17 |
| WO | WO-2016/054603 A2 | 4/2016 | | |
| WO | WO-2016/054603 A3 | 4/2016 | | |
| WO | WO-2016120218 A1 * | 8/2016 | ............. | A61K 35/17 |
| WO | WO-2016/154621 A1 | 9/2016 | | |
| WO | WO-2016/187158 A1 | 11/2016 | | |
| WO | WO-2017/132486 A1 | 8/2017 | | |

OTHER PUBLICATIONS

Rudikoff et al. (PNAS USA, 1982, 79: 1979-1983) (Year: 1982).*
Burgess et al. (J of Cell Bio. 111:2129-2138, 1990) (Year: 1990).*
Ibragimova and Wade (Biophysical Journal, Oct. 1999, vol. 77, pp. 2191-2198) (Year: 1999).*
Bzymek et al. (Acta Cryst 2016 F72: 434-442) (Year: 2016).*
Caratelli, S. et al. (Apr. 27, 2017). "FCγ Chimeric Receptor-Engineered T Cells: Methodology, Advantages, Limitations, and Clinical Relevance," *Front Immunol* 8:457.
D'Aloia, M.M. et al. (Feb. 2016). "T lymphocytes engineered to express a CD16-chimeric antigen receptor redirect T-cell immune responses against immunoglobulin G-opsonized target cells," *Cytotherapy* 18(2):278-290.
Donaldson, et al. (Oct. 22, 2013, e-published Oct. 7, 2013). "Identification and grafting of a unique peptide-binding site in the Fab framework of monoclonal antibodies," *PNAS USA* 110(43):17456-17461.
Extended European Search Report mailed Oct. 8, 2021, for EP Patent Application No. 18896671.7, 8 pages.

(Continued)

*Primary Examiner* — Peter J Reddig
(74) *Attorney, Agent, or Firm* — Mintz Levin Cohn Ferris Glovsky and Popeo PC

(57) ABSTRACT

Provided herein are compositions which exhibit novel therapeutic capabilities and allow to reduce the off-target effect of therapeutic antibodies. The compositions include recombinant proteins that if expressed by a T cell can efficiently recruit therapeutic antibodies to their site of action.

18 Claims, 50 Drawing Sheets
Specification includes a Sequence Listing.

(56)        References Cited

OTHER PUBLICATIONS

International Search Report mailed on Mar. 18, 2019, for PCT Application No. PCT/US2018/068235, filed Dec. 31, 2018, 3 pages.
Priceman, S.J. et al. (Oct. 16, 2017). "Co-stimulatory signaling determines tumor antigen sensitivity and persistence of CAR T cells targeting PSCA+ metastatic prostate cancer," *Oncoimmunology* 7(2):1380764, pp. 1-13.
Written Opinion mailed on Mar. 18, 2019, for PCT Application No. PCT/US2018/068235, filed Dec. 31, 2018, 7 pages.

* cited by examiner

| | Sample Name | Subset Name | Count |
|---|---|---|---|
| ▣ | CH3647 Fab 200 nME7.0001.fcs | CD19+ | 596 |
| ▦ | CH3647 Fab 200nM + Her2 200nMF7.0001.fcs | CD19+ | 622 |

647^I83E Fab

| | Sample Name | Subset Name | Count |
|---|---|---|---|
| | CH3647 Ipi 100 nMG7.0001.fcs | CD19+ | 704 |
| | CH3No Stain647 Ipi 100nM + Her2 200nMH9.0001.fcs | CD19+ | 551 |

647^Ipi IgG

T cells with memAb pre-binding    Cancer cells with memAb pre-binding

Lower T cell activation compared to memAb pre-binding to cancer cells

Similar T cell activation with memAb pre-binding to cancer cells

Higher T cell activation compared to memAb pre binding to cancer cells

Similar T cell activation with memAb pre-binding to cancer cells

FIG. 31

*Jurkat*

*fill: 2ⁿᵈ anti-kappa-647*
*blank: memAb*
*Trastuzumab + 2ⁿᵈ anti-*
*kappa-647*

*fill: 2ⁿᵈ anti-kappa-647*
*blank: Cetuximab + 2ⁿᵈ*
*anti-kappa-647*

*FabRack*
*Jurkat*

*fill: 2ⁿᵈ anti-kappa-647*
*blank: Herceptin + 2ⁿᵈ*
*anti-kappa-647*

| | BT474 | SKBR3 | MCF7 | SKOV3 | OVCAR3 |
|---|---|---|---|---|---|
| IC50 (nM) | 0.3272 | 0.113 | 0.06878 | 0.2298 | 0.0245 |

| | 468 | SKOV3 | SKBR3 |
|---|---|---|---|
| EC50 (nM) | 0.2061 | 0.1314 | 0.1222 |

MEDITOPE-ENABLED T CELLS

CROSS REFERENCE TO RELATED APPLICATIONS

This application is a National Stage Entry of PCT Application No. PCT/US2018/68235, filed Dec. 31, 2018, which claims priority to U.S. Provisional Application No. 62/611,924, filed Dec. 29, 2017, and U.S. Provisional Application No. 62/680,442, filed Jun. 4, 2018, which are hereby incorporated by reference in their entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 048440-621N01US_Sequence_Listing_ST25.txt, created Jul. 13, 2020, 29,689 bytes, machine format IBM-PC, MS Windows operating system, is hereby incorporated by reference.

SUMMARY OF THE INVENTION

In one aspect, a first recombinant protein is provided. The first recombinant protein includes (i) a first non-CDR Fab binding peptide domain; (ii) a first intracellular T-cell signaling domain; and (iii) a first transmembrane domain connecting the first non-CDR Fab binding peptide domain to the first intracellular T-cell signaling domain. In embodiments, the first recombinant protein includes a first spacer region connecting the first non-CDR Fab binding peptide domain to the first transmembrane domain. In embodiments, the first spacer region is a first CH3 region.

In one aspect, an isolated nucleic acid encoding a first recombinant protein provided herein including embodiments thereof is provided.

In one aspect, an expression vector including a nucleic acid provided herein including embodiments thereof is provided. In embodiments, the vector is a lentivirus or onco-retrovirus.

In one aspect, a T lymphocyte including an expression vector provided herein including embodiments thereof is provided.

In one aspect, a T lymphocyte including a first recombinant protein provided herein including embodiments thereof is provided.

In one aspect, a T lymphocyte including a first recombinant protein provided herein including embodiments thereof is provided, wherein the transmembrane domain is within the cell membrane of the T lymphocyte.

In one aspect, a method of treating cancer is provided. The method includes administering to a subject in need thereof an effective amount of the T-lymphocyte provided herein including embodiments thereof is provided, wherein the first antigen-binding domain and the second antigen-binding domain are independently an anti-cancer antigen-binding domain.

In an aspect, a recombinant protein is provided. The recombinant protein includes: (i) a non-CDR Fab binding peptide domain; (ii) an intracellular T-cell signaling domain; and (iii) a transmembrane domain connecting the non-CDR Fab binding peptide domain to the intracellular T-cell signaling domain.

In an aspect, an isolated nucleic acid encoding a recombinant protein provided herein including embodiments thereof is provided.

In an aspect, an expression vector including the nucleic acid provided herein including embodiments thereof is provided.

In an aspect, a T lymphocyte including the expression vector provided herein including embodiments thereof is provided.

In an aspect, a T lymphocyte including the recombinant protein provided herein including embodiments thereof is provided.

In an aspect, a T lymphocyte including the recombinant protein provided herein including embodiments thereof is provided, wherein the transmembrane domain is within the cell membrane of the T lymphocyte.

In an aspect, a method of treating cancer is provided. The method includes administering to a subject in need thereof an effective amount of the T lymphocyte provided herein including embodiments thereof and an antigen-binding domain capable of binding to the non-CDR Fab binding peptide domain, wherein the antigen-binding domain is a cancer antigen-binding domain.

BRIEF DESCRIPTION OF THE DRAWINGS

FIG. 1A) Chimeric Antigen Receptor (CAR) T cells are typically created by fusing an antigen specific single chain Fab variable (e.g., the heavy and light variable domains of a mAb) to the CD3 zeta chain. As such, each CAR T cell requires the creation of a new gene to change the target specificity. FIG. 1B) To remove this restriction, Applicants have used the meditope technology to 'snap' on antibody fragments to engineered T Cells. Specifically, Applicants have replaced the scFv with the cQFD meditope. FIG. 1C) Cartoon demonstration of the current technology for single antigen-specific CAR T cells and how meditope technology can be used to create universal CARs.

Figures 2A, 2B, 2C:
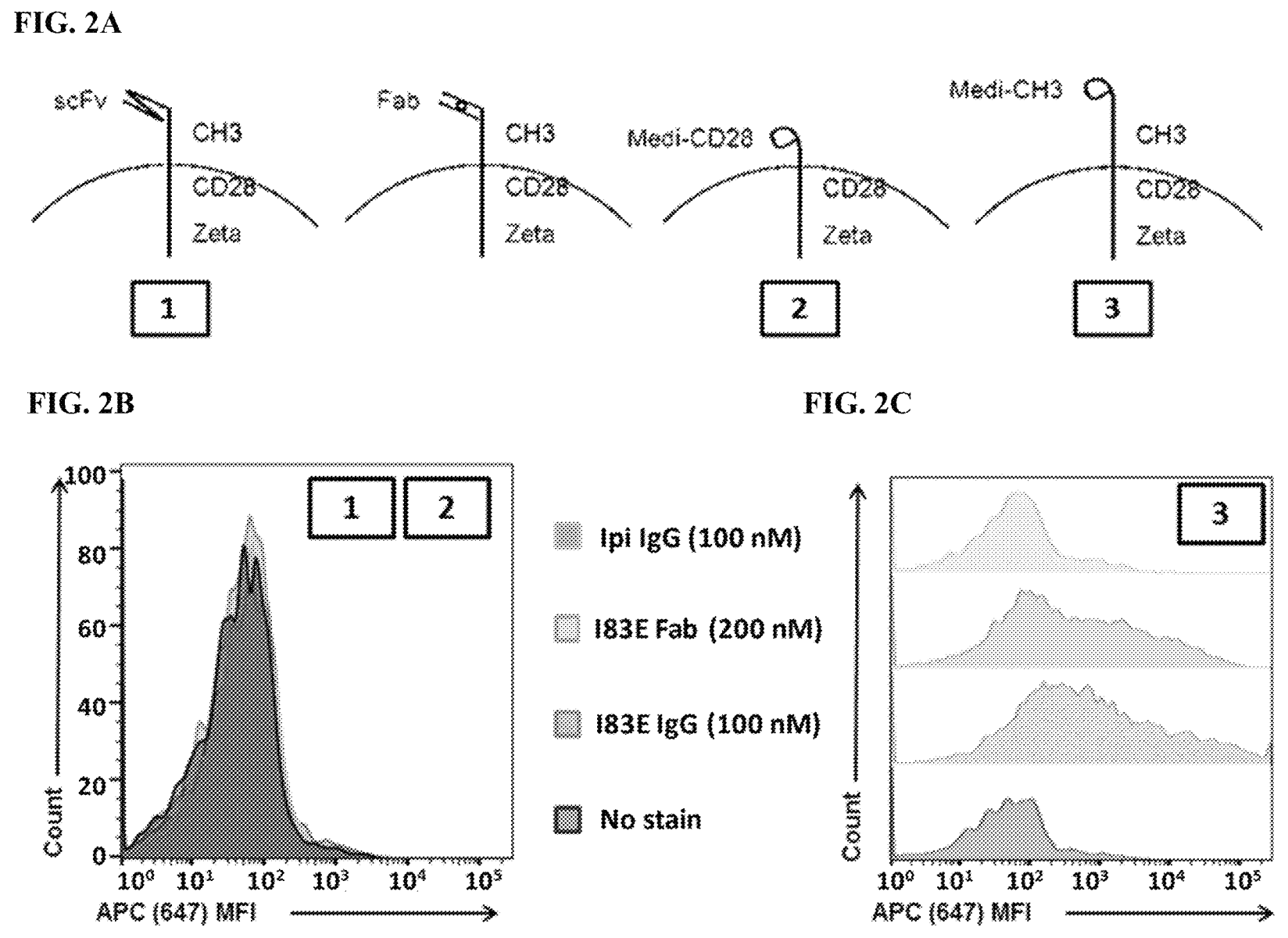

FIG. 2A-2C. FIG. 2A) CHO-S cells were transfected with either no vector (Mock), Parental CAR (1), Meditope-CH3 (3), or Meditope-CD28 (2) to test the binding of meditope-enabled I83E trastuzumab IgG conjugated to fluorescent dye Alexa Fluor 647 (647^I83E IgG), meditope-enabled I83E trastuzumab Fab conjugated to fluorescent dye Alexa Fluor 647 (647^I83E Fab), and non-meditope-enabled Ipilimumab IgG conjugated to fluorescent dye Alexa Fluor 647 (647^Ipi IgG). Live transfected cells were identified using FSC/SSC→PI⁻→CD19⁺ gating (See FIG. 3A). Cells were analyzed for mean fluorescence intensity (MFI) of APC signal. FIG. 2B) Cells transfected with no vector (Mock), Parental CAR (1), or Meditope-CD28 (2) failed to show a shift in MFI went stained with 647^I83E IgG, 647^I83E Fab, or 647^Ipi IgG. FIG. 2C) Cells transfected with Meditope-CH3 (3) showed a significant shift in MFI when stained with 647^I83E IgG or 647^I83E Fab, but only a minimal shift when stained with 647^Ipi IgG.

FIG. 3A) Cells were gated by FSC/SSC (left panel), PI⁻ staining (indicates live cells; middle panel), and CD19 expression (a transfection marker; right panel). FIG. 3B) Further analyses of the gated cells measured 647 (left panel) and VioBlue (right panel) signals indicating antibody and Her2 binding, respectively.

FIG. 4A) Live transfected cells were identified using FSC/SSC→PI⁻→CD19⁺ gating. Cells were analyzed for mean fluorescence intensity (MFI) of APC signal. Cells with no stain were used to set gate for APC⁺ cells. Cells stained with non-meditope-enabled 647^Ipi IgG showed minimal shift in APC MFI. Cells stained with meditope-enabled 647^I83E IgG and Fab showed a significant shift in APC MFI, demonstrating binding of 647-conjugated protein to Meditope-CH3 expressing cells. FIG. 4B) This trend was not seen in the Meditope-CD28 construct. FIG. 4C) Percentage of live CD19$^+$ cells that are positive for 647^IgG or 647^Fab (Gated cells: FSC/SSC→PI$^-$→CD19$^+$→APC$^+$; APC$^+$ cells frequency of parent population).

FIG. 5A) Histogram of Her2 mean fluorescence intensity (MFI) on Meditope-CH3 CAR cells that are APC$^+$ (Gated cells: FSC/SSC→PI$^-$→CD19$^+$→APC$^+$). FIG. 5B) Percentage of live CD19$^+$ 647$^+$ cells that are positive for Her2 (Her2$^+$ cells frequency of grandparent population, same gating strategy as above).

FIG. 6A) Analysis of cells stained with meditope-enabled 647^I83E Fab. FIG. 6B) Analysis of cells stained with meditope-enabled 647^I83E IgG. FIG. 6C) Analysis of cells stained with non-meditope enabled 647^Ipi IgG.

FIG. 8A) Percentage of live CD19$^+$ cells that are positive for 647^Fab (Gated cells: FSC/SSC→PI$^-$→CD19$^+$→APC$^+$; APC$^+$ cells frequency of parent population). FIG. 8B) Live cells transfected with Meditope-CH3 were identified using FSC/SSC→PI$^-$→CD19$^+$ gating. Cells were analyzed for mean fluorescence intensity (MFI) of APC signal. Cells with no stain were used to set gate for APC$^+$ cells. Cells stained with non-meditope-enabled 647^Ipi Fab showed minimal shift in APC MFI. Cells stained with meditope-enabled 647^I83E cetuximab (cetux) Fab and 647^I83E trastuzumab (tras) Fab showed a significant shift in APC MFI, demonstrating binding of 647-conjugated protein to Meditope-CH3 expressing cells.

FIG. 9A) Analysis of cells stained with meditope-enabled 647^I83E cetuximab (cetux) Fab. FIG. 9B) Analysis of cells stained with meditope-enabled 647^I83E trastuzumab (tras) Fab.

202832) or anti-human-IgG Fc-488 (ThermoFisher #H10120). The result showed that only memAb trastuzumab can bind to meditope-CAR expressing Jurkat cells after cells were analyzed by flow cytometry.

Figure 16:
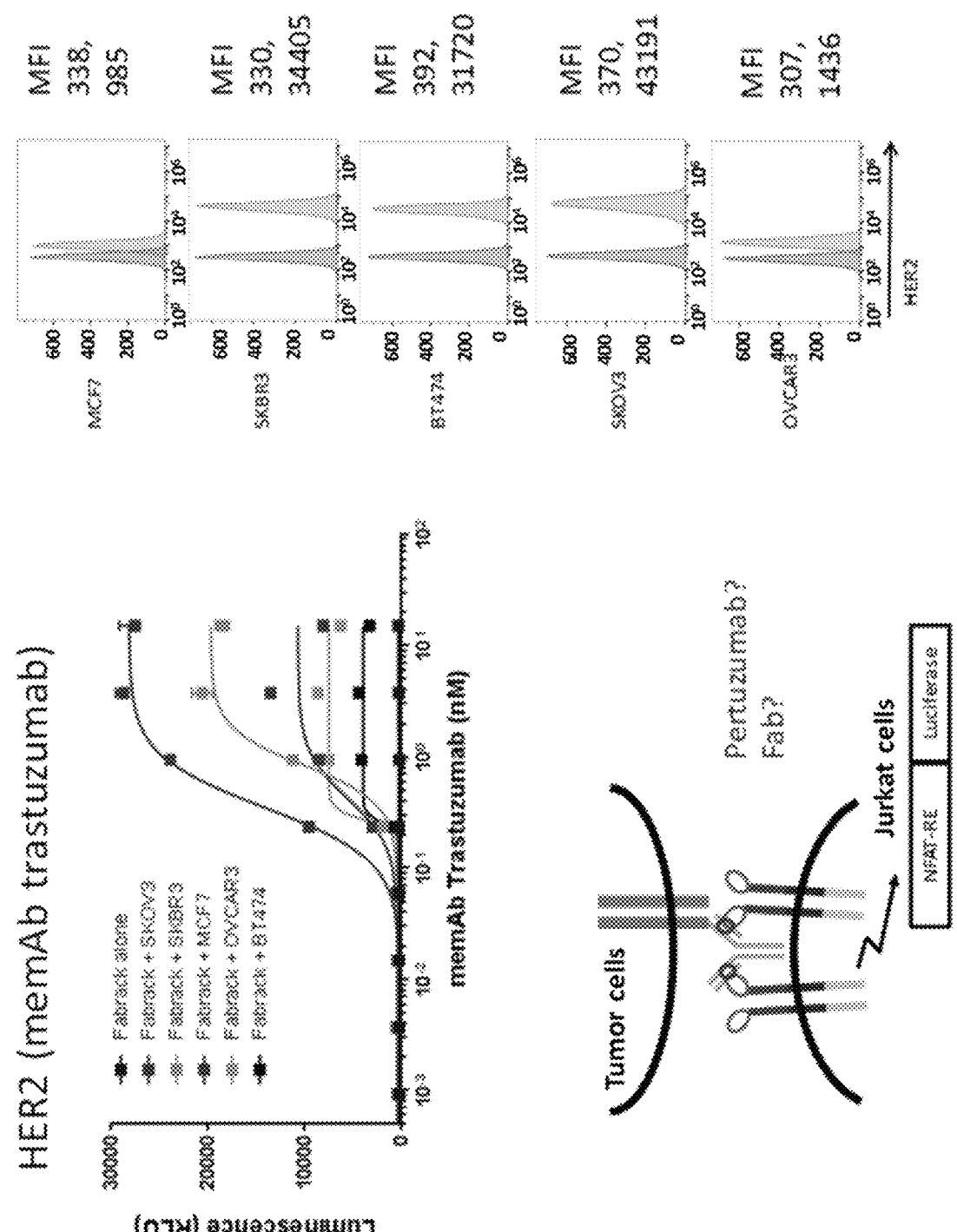

FIG. 16. Left: Cancer cells, Jurkat-NFAT-Luc meditope-CAR cells and memAb trastuzumab were co-incubated in white-wall 96-well plates. The highest concentration in the figure is 15 nM and followed by 4-fold serial dilution. After 6 h incubation, luciferase substrate was added in each well and luminescence was immediately measured using a plate reader. In the presence of memAb trastuzmab, Jurkat cell activation increased dose-dependently in spite of hook effect setting in at 15 nM. The EC50 for each cell line is 0.35 nM (SKOV3), 0.83 nM (SKBR3), 0.42 nM (MCF7), 0.27 nM (OVCAR3) and 0.26 nM (BT474). The level of Jurkat cell activation is positively associated with HER2 expression on cancer cells except BT474 cell line. Although BT474 has high HER2 expression, it does not activate Jurkat cell to the same level as other high HER2 expressing cells (SKOV3 and SKBR3). Right: $5 \times 10^5$ cells were treated with 100 nM memAb trastuzumab in 1% FBS in PBS for 30 min. After washed three times, cells were labeled with secondary anti-kappa-647 antibody for 30 min. Fluorophore intensity of cells was analyzed by BD Accuri C6 flow cytometer. Red peak are cells treated with secondary anti-kappa-647 antibody alone. Green peak are cells treated with memAb trastuzumab and secondary anti-kappa-647 antibody. The flow cytometry was used to analyze HER2 expression level by comparing cells stained with secondary antibody alone or with memAb trastuzumab and secondary antibodies. The median fluorescence intensity (MFI) are 338 and 985 for MCF7 cells; 330 and 34405 for SKBR3 cells; 392 and 31720 for BT474 cells; 370 and 43191 for SKOV3 cells; 307 and 1436 for OVCAR3 cells. Cells with HER2 expression from high to low are SKOV3, SKBR3, BT474, OVCAR3 and MCF7.

Figure 17:
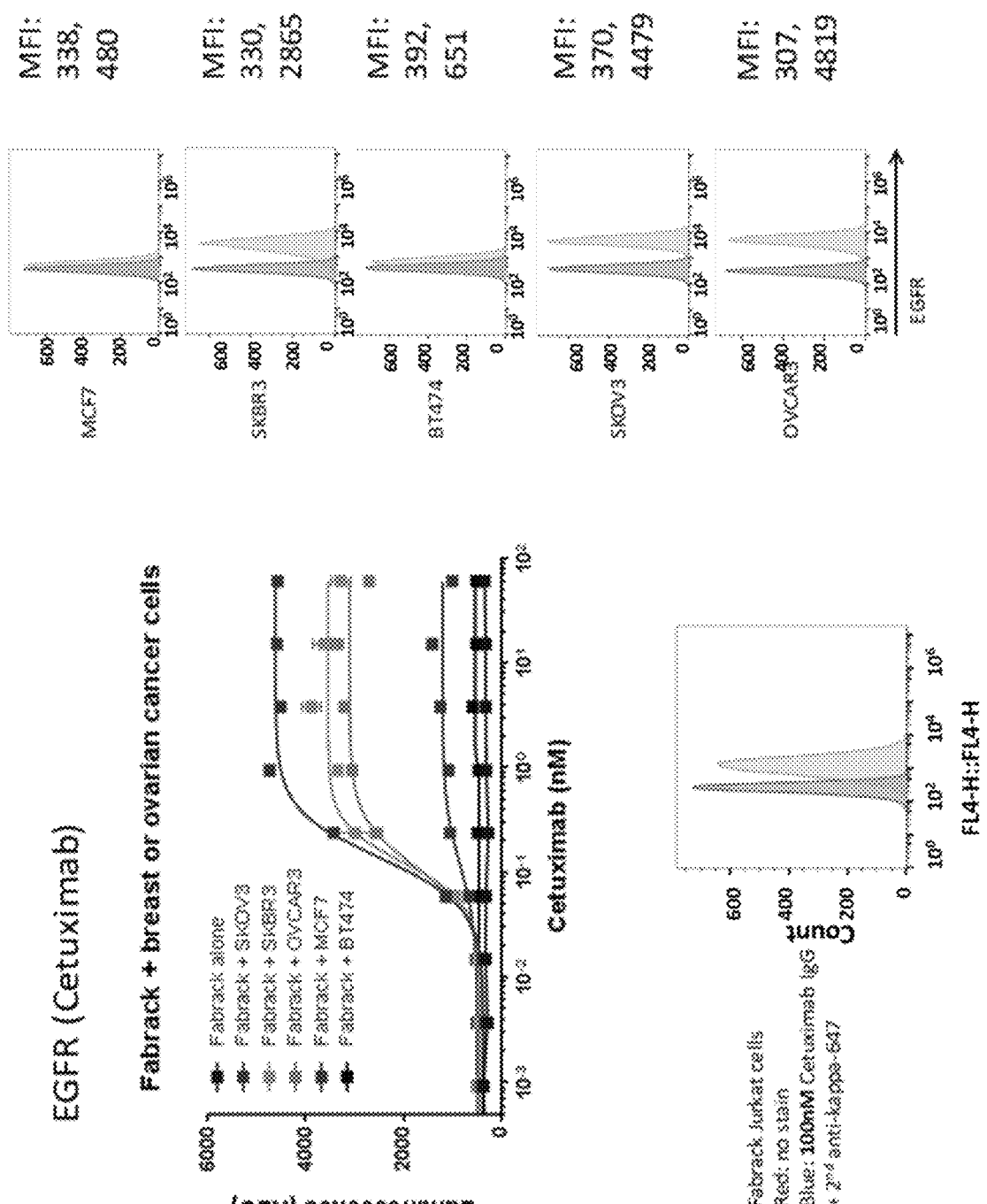

FIG. 17. Left: Cancer cells, FabRack Jurkat-NFAT-Luc cells and Cetuximab were co-incubated in white-wall 96-well plates. The highest concentration in figure is 60 nM and followed by 4-fold serial dilution. After 6 h incubation, luciferase substrate was added in each well and luminescence was immediately measured using a plate reader. The EC50 for each cell line is 0.14 nM (SKOV3), 0.12 nM (SKBR3), 0.12 nM (MCF7), 0.11 nM (OVCAR3) and 1.1 nM (BT474). Right: $5*10^5$ cells were treated with 100 nM Cetuximab in 1% FBS PBS for 30 min. After washed three times, cells were labeled with secondary anti-kappa-647 antibody for 30 min. Fluorophore intensity of cell was analyzed by BD Accuri C6 flow cytometer. Red peak are cells treated with secondary anti-kappa-647 antibody alone. Green peak are cells treated with Cetuximab and secondary anti-kappa-647 antibody. Median fluorescence intensity showed that cells with EGFR expression from high to low are OVCAR3 (4819), SKOV3 (4479), SKBR3 (2865), BT474 (651) and MCF7 (480).

Figure 18:
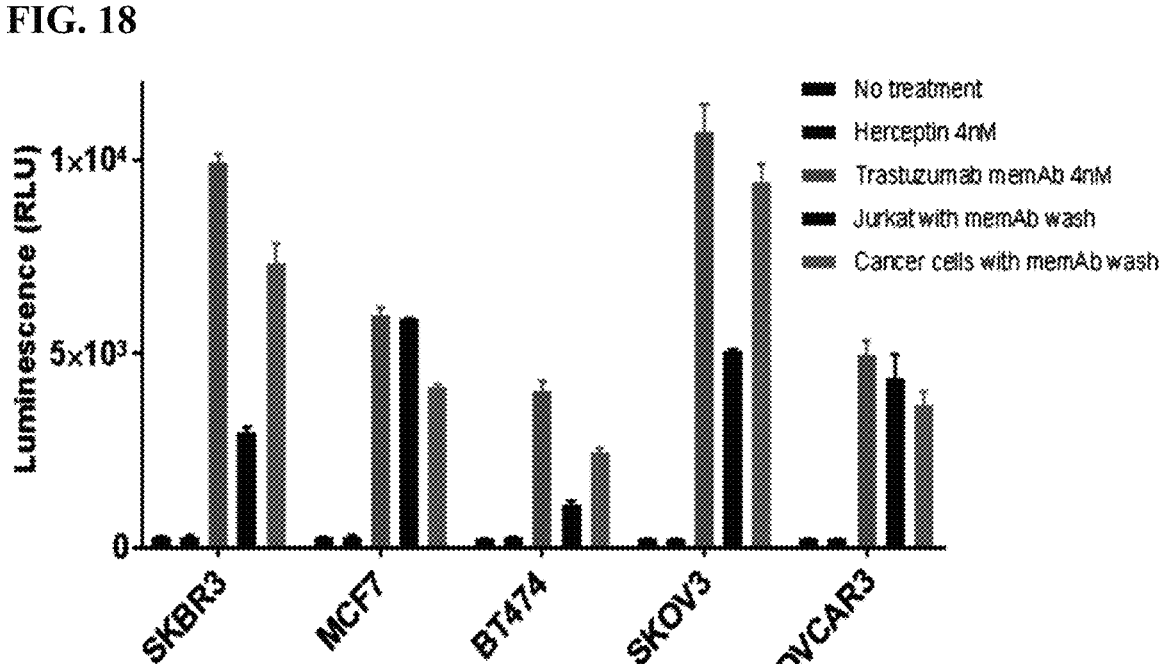

FIG. 18. The figure shows Jurkat or cancer cells with memAb trastuzumab pre-mix and wash. Jurkat or cancer cells with memAb trastuzumab pre-binding followed by a wash. Cancer cells ($2.5 \times 10^4$/100 ul) were seeded in 96-well white-wall plate. After cell attachment for overnight, media in the plate was removed and Jurkat-NFAT-Luc meditope-CAR cells ($1 \times 10^5$/60 ul) were added to each well. memAb Trastuzumab was continuously present or pre-bound to Jurkat-NFAT-Luc medi-CAR or cancer cells with wash. (Bars in the graph represent, from left to right: no treatment; Herceptin (4 nM) continuously present; memAb trastuzumab (4 nM) continuously present; FabRack Jurkat- NFAT-Luc cells with memAb trastuzumab (100 nM) pre-bound followed by a wash; cancer cells with memAb trastuzumab (100 nM) pre-bound followed by a wash.) Cells were incubated at 37° C. for 6 hr followed by addition of 50 ul luciferase substrate (Invivogen #rep-qlc2) to each well. The luminescence was immediately measured using Biotek's Synergy 4 multi-detection microplate reader.

Figure 19:
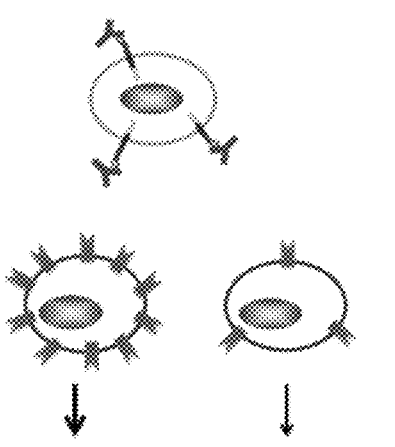
Figure 19:
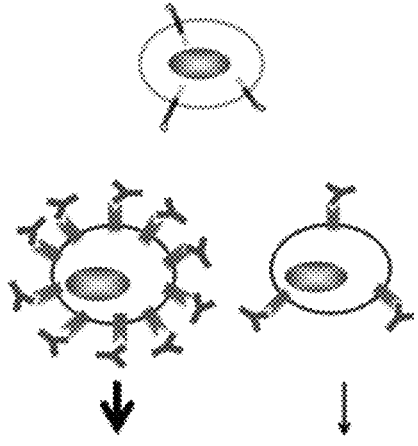

FIG. 19. The figure shows T cells with memAb pre-binding (Left) and cancer cells with memAb pre-binding (Right).

Figure 20:
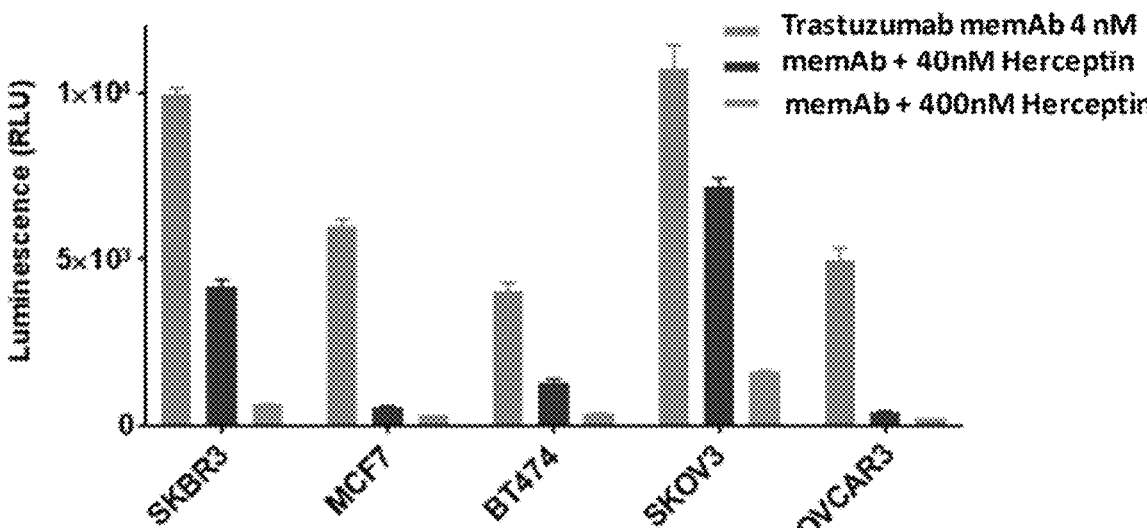

FIG. 20. The figure shows that Herceptin blocks I83E mediated Jurkat-NFAT-Luc activation. memAb trastuzumab and Herceptin were continuously present. Cancer cells (2.5× $10^4$/100 ul) were seeded in 96-well white-wall plate. After cell attachment for overnight, media in the plate was removed and Jukat-NFAT-Luc me-CAR cells (1×$10^5$/60 ul) were added to each well. memAb trastuzumab was continuously present or pre-bound to Jurkat or cancer cells with wash. (Bars in the graph represent, from left to right: memAb trastuzumab (4 nM) continuously present; memAb trastuzumab (4 nM) and Herceptin (40 nM) continuously present; memAb trastuzumab (4 nM) and Herceptin (400 nM) continuously present.) Cells were incubated at 37° C. for 6 hr followed by addition of 50 ul luciferase substrate (Invivogen #rep-qlc2) to each well. The luminescence was immediately read by Biotek's Synergy 4 multi-detection microplate reader. In the continuous presence of 4 nM memAb trastuzumab, Jurkat-NFAT-Luc medi-CAR cells were activated due to binding to cancer cells by memAb trastuzumab. Continuous presence of Herceptin during incubation can block Jurkat cell activation, because Herceptin has the same epitope as our memAb trastuzumab and can compete the same binding site on HER2. Herceptin (400 nM) with 100 fold concentration of memAb trastuzumab (4 nM) almost completely block Jurkat cell activation, which demonstrated that Jurkat cell activation was caused by memAb trastuzumab binding to the same HER2 epitope recognized by Herceptin.

Figure 21:
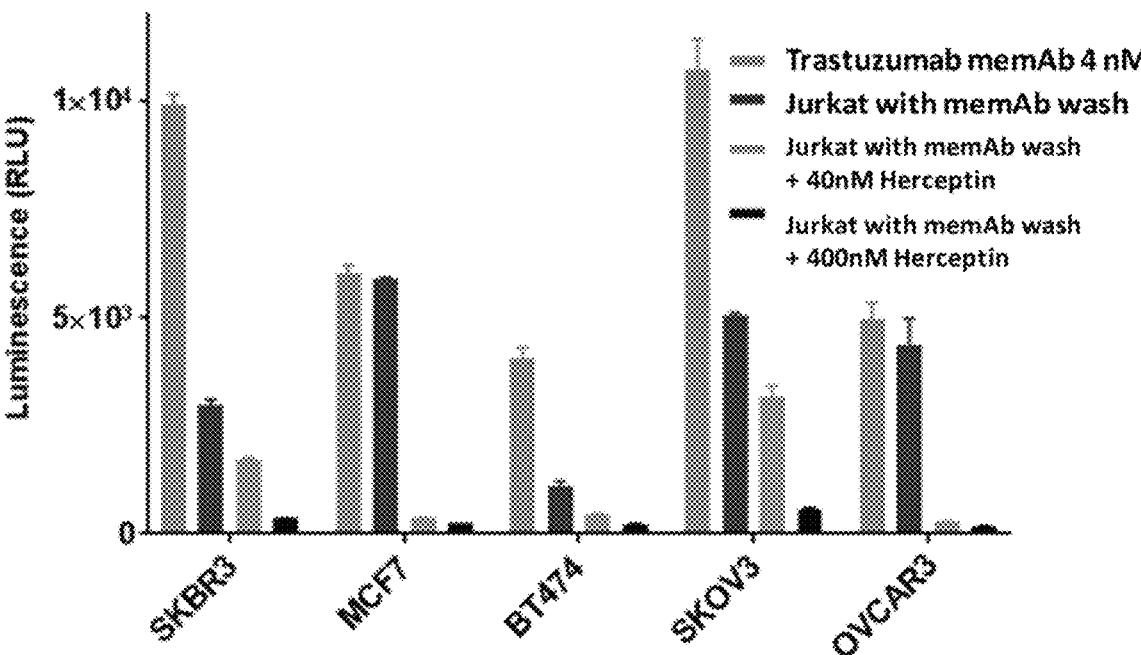

FIG. 21. The figure shows that Herceptin blocks memAb mediated Jurkat-NFAT-Luc activation after Jurkat cells with memAb trastuzumab pre-mix and wash. memAb trastuzumab pre-bound to Jurkat cells first and wash. Herceptin was continuously present. Cancer cells (2.5×$10^4$/100 ul) were seeded in 96-well white-wall plate. After cell attachment for overnight, media in the plate was removed and Jukat-NFAT-Luc me-CAR cells (1×$10^5$/60 ul) were added to each well. memAb trastuzumab was continuously present or pre-bound to Jurkat-NFAT-Luc medi-CAR cells with wash. (Bars in the graph represent, from left to right: memAb trastuzumab (4 nM) continuously present; Jurkat-NFAT-Luc medi-CAR cells with memAb trastuzumab (100 nM) pre-bound followed by a wash; Jurkat-NFAT-Luc medi-CAR cells with memAb trastuzumab (100 nM) pre-bound followed by a wash+Herceptin (40 nM) continuously present; Jurkat-NFAT-Luc medi-CAR cells with memAb trastuzumab (100 nM) pre-bound followed by a wash+Herceptin (400 nM) continuously present.) Cells were incubated at 37° C. for 6 hr followed by addition of 50 ul luciferase substrate (Invivogen #rep-qlc2) to each well. The luminescence was immediately measured using Biotek's Synergy 4 multi-detection microplate reader. Jurkat-NFAT-Luc medi-CAR cells with memAb trastuzumab pre-binding followed by a wash significantly decreased luminescence activity when co-incubated with high HER2 expressing cells (SKBR3, BT474 and SKOV3) but not in low HER2 expressing cells (MCF7 and OVCAR3) compared to cells with memAb continuous presence. Continuous presence of Herceptin during incubation can block Jurkat cell activation. The number of medi-CAR on each Jurkat cell or target molecule on each cancer cell may determine how much activation show in each T cell or how many T cells are activated.

Figure 22:
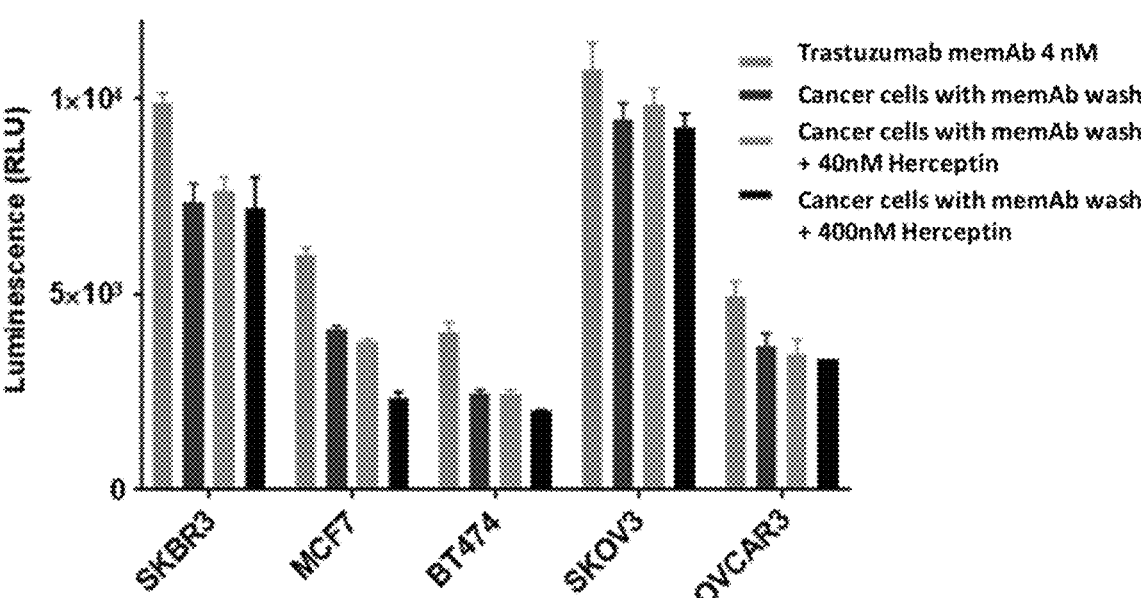

FIG. 22. The figure shows that Herceptin hardly blocked memAb trastuzumab mediated Jurkat-NFAT-Luc activation after cancer cells with memAb pre-mix and wash. memAb trastuzumab pre-bound to cancer cells first and wash. Herceptin was continuously present. Cancer cells with memAb trastuzumab pre-binding followed by a wash did not dramatically decreased luminescence activity compared to cells with memAb continuous presence. Continuous presence of Herceptin during incubation had no or some blocking effect on Jurkat cell activation. This data demonstrated that once memAb treastuzumab was bound to HER2 on cancer cells, it was hard to be competed by trastuzumab without medi-tope-binding site. Cancer cells (2.5×$10^4$/100 ul) were seeded in 96-well white-wall plate. After cell attachment for overnight, media in the plate was removed and Jukat-NFAT-Luc me-CAR cells (1×$10^5$) were added to each well. memAb Trastuzumab was continuously present or pre-bound to cancer cells with wash. (Bars in the graph represent, from left to right: memAb trastuzumab (4 nM) continuously present; cancer cells with memAb trastuzumab (100 nM) pre-bound followed by a wash; cancer cells with memAb trastuzumab (100 nM) pre-bound followed by a wash+Herceptin (40 nM) continuously present; cancer cells with memAb trastuzumab (100 nM) pre-bound followed by a wash+Herceptin (400 nM) continuously present.) Cells were incubated at 37° C. for 6 hr followed by addition of 50 ul luciferase substrate (Invivogen #rep-qlc2) to each well. The luminescence was immediately measured using Biotek's Synergy 4 multi-detection microplate reader.

Figure 23:
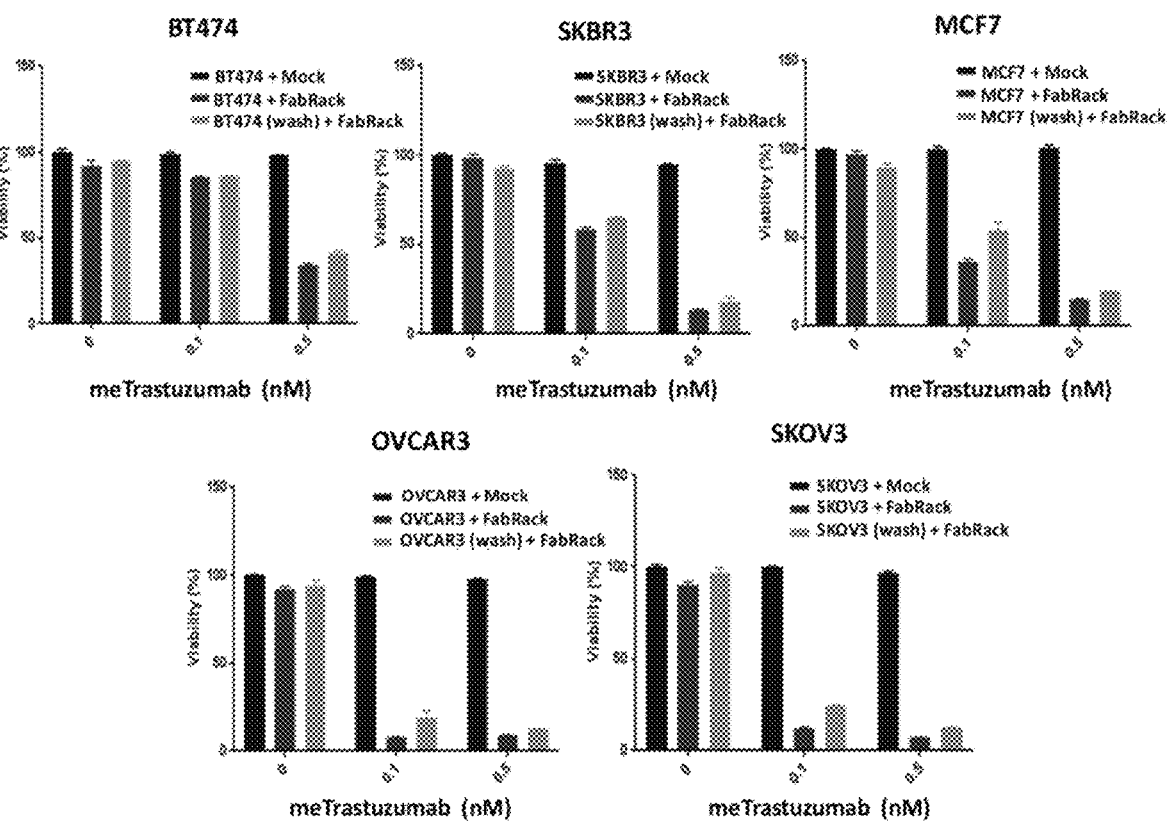

FIG. 23. The figure shows that T cells kill cancer cells with memAb Trastuzumab pre-mix and wash. Viability (%)=[Luc$_{(cancer\ cells+\ T\ cells+antibody)}$−Luc$_{(T\ cells+antibody)}$]/[Luc$_{(cancer\ cells+Tmock\ cells)}$−Luc$_{(Tmock\ cells)}$]. In the continuous presence of 0.1 nM or 0.5 nM mem antibody, the viability of cancer cell with FabRack T cell co-incubation decreased compared to that with mock T cell co-incubation. Cell viability decreased dose-dependently at 0.1 and 0.5 nM in breast cancer cell, while ovarian cancer cells show similar viability at these two concentrations. Cancer cells with antibody pre-binding and washout can still be killed by human FabRack T cells in spite of reversal of viability by 5-18% compared with cancer cells with continuous antibody treatment. For tumor killing assay, cancer cells (2.5×$10^4$/100 ul) and human T cells (6,250/100 ul) were seeded in 96-well round-bottom plate in the presence or absence of antibody. After 72 h incubation, cells were centrifuged at 250×g for 5 min and 100 ul of media in each well was removed. To test cell viability, 100 ul of reagent from Promega CellTiter kit was added in each well. After two-minute incubation, 100 ul of mixture was moved to a white-wall 96-well plate and measured using Biotek's Synergy 4 multi-detection microplate reader.

Figure 24:
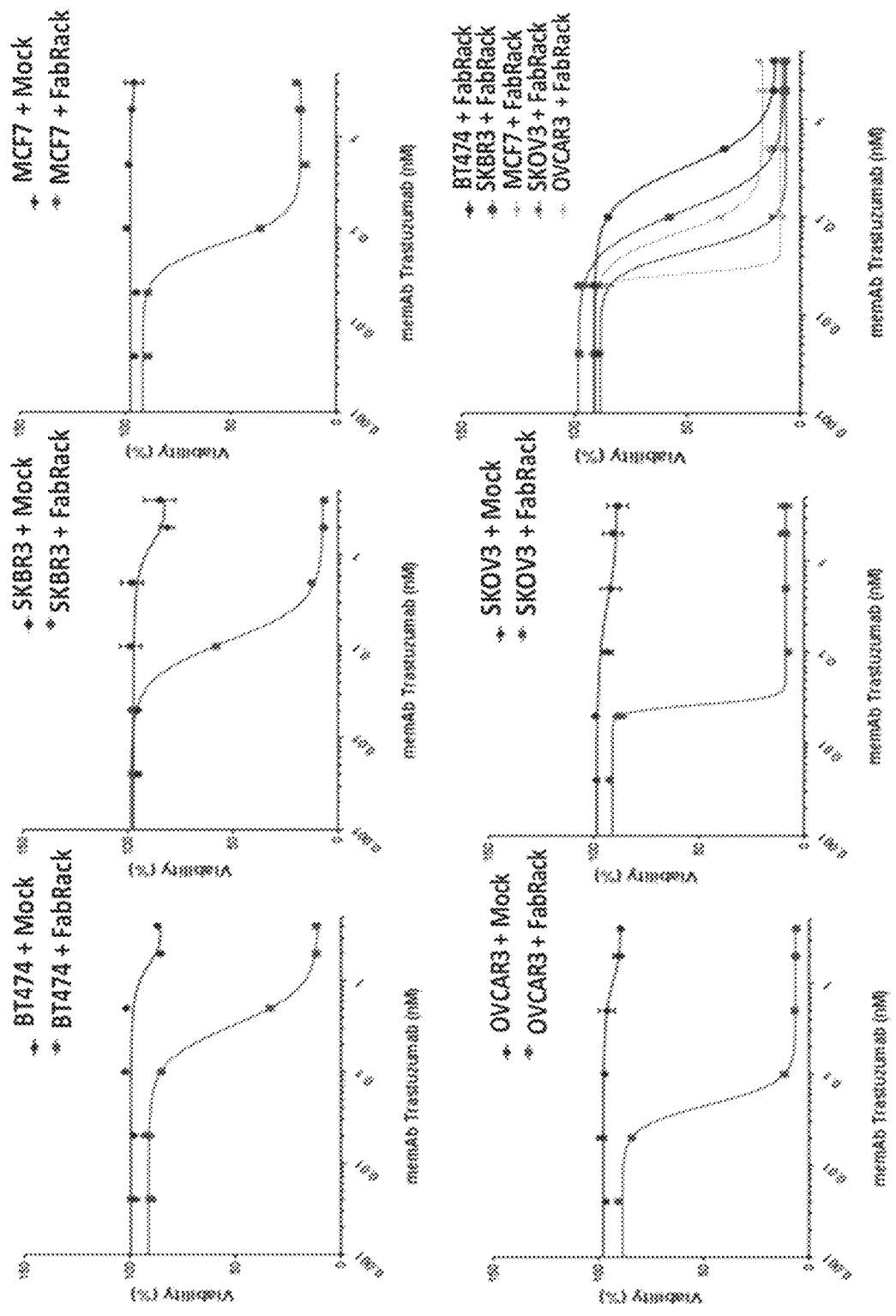

FIG. 24. The figure shows that FabRack T cells kill cancer cells effectively at lower dose of memAb trastuzumab. Cancer cells were incubated with mock T cells or FabRack T cells in the presence of memAb trastuzumab for 3 days. This data showed that FabRack T cells killed HER2 positive cancer cells effectively since they bind cancer cells through memAb trastuzumab. IC50 of cancer cells co-incubated with memAb trastuzumab and FabRack T cells are 0.33 nM (BT474), 0.11 nM (SKBR3), 0.069 nM (MCF7), 0.046 nM (SKOV3) and 0.027 nM (OVCAR3). The killing effect was not associated with HER2 expression level on cancer cells. For tumor killing assay, cancer cells (2.5×10$^4$/100 ul) and human T cells (6,250/100 ul) were seeded in 96-well round-bottom plate in the presence or absence of antibody. After 72 h incubation, cells were centrifuged at 250×g for 5 min and 100 ul of media in each well was removed. To test cell viability, 100 ul of reagent from Promega CellTiter kit was added in each well. After two-minute incubation, 100 ul of mixture was moved to a white-wall 96-well plate and measured using Biotek's Synergy 4 multi-detection micro-plate reader.

Figure 25:
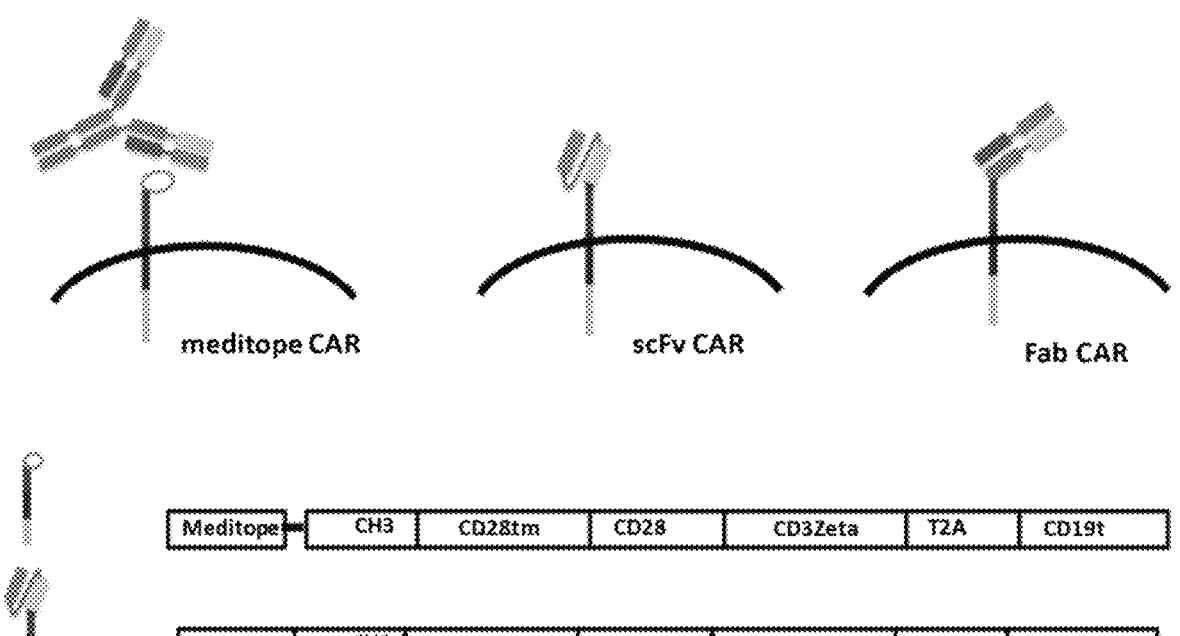

FIG. 25. The figure shows tumor killing of meditope-CAR compared to scFv CAR and Fab CAR T cells (T cells expressing the recombinant protein provided herein including embodiments thereof).

Figure 26:
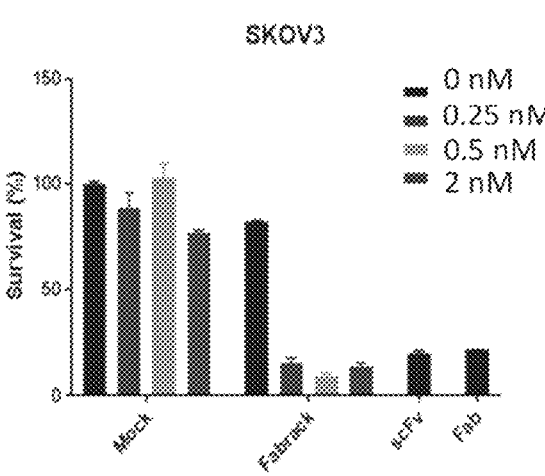
Figure 26:
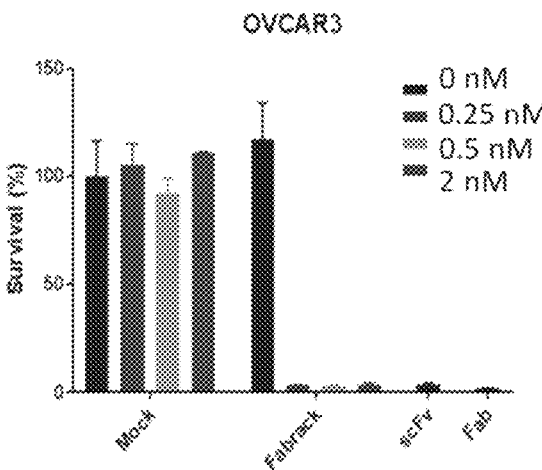

FIG. 26. The figure shows tumor killing assay in ovarian cancer (FACS). Flow cytometry were used to analyze how many cancer cells were still live after they were co-incubated with FabRack T cells and memAb trastuzumab compared with cancer cells incubated with HER2 scFv CAR or HER2 Fab CAR T cells as positive control. After incubation for 3 days, the viable cancer cells dramatically decreased when co-incubated with FabRack T cells and memAb trastuzumab. The killing effect of FabRack T cells was similar or even better than HER2 scFv CAR or HER2 Fab CAR T cells.

Figure 27:
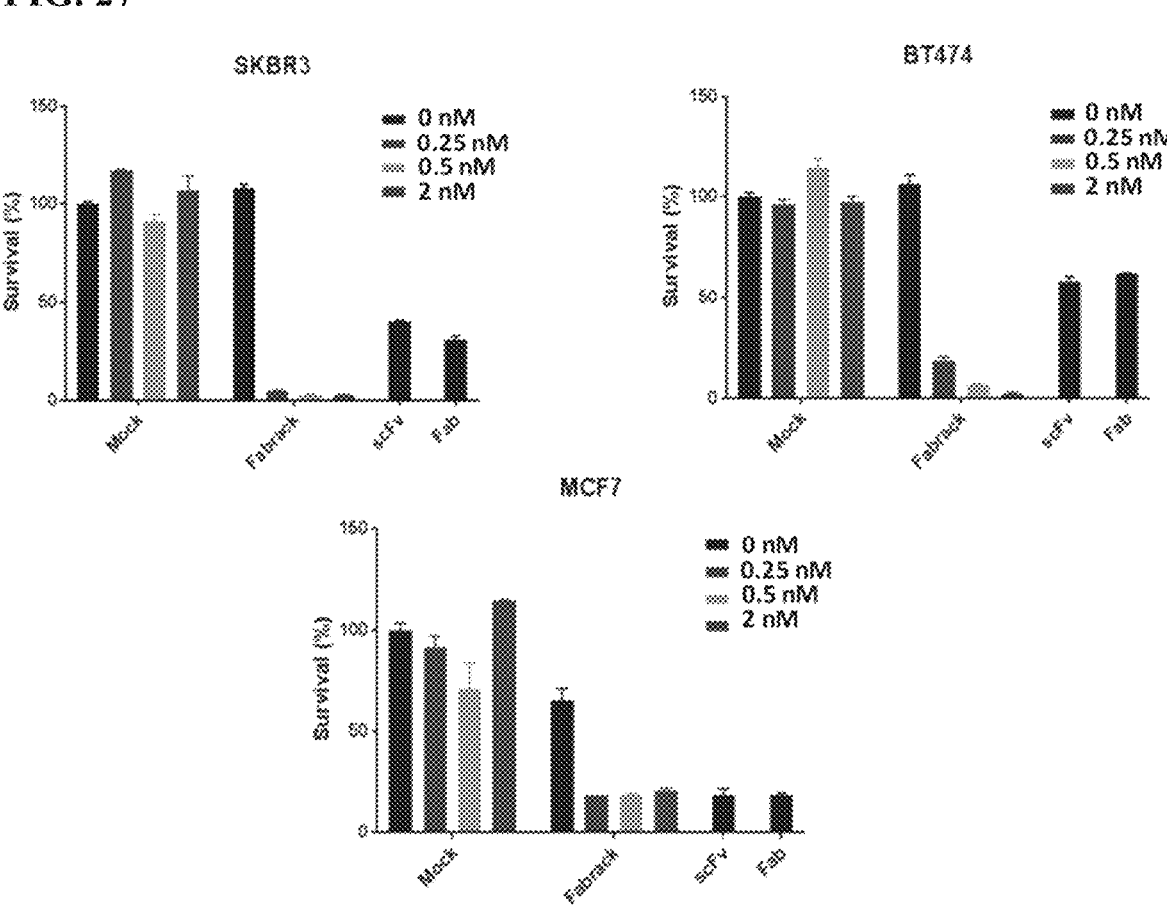

FIG. 27. The figure shows tumor killing assay in breast cancer (FACS). Flow cytometry were used to analyze how many cancer cells were still live after they were co-incubated with FabRack T cells and memAb trastuzumab compared with cancer cells incubated with HER2 scFv CAR or HER2 Fab CAR T cells as positive control. After incubation for 3 days, the viable cancer cells dramatically decreased when co-incubated with FabRack T cells and memAb trastuzumab. The killing effect of FabRack T cells was similar or even better than HER2 scFv CAR or HER2 Fab CAR T cells.

Figure 28:
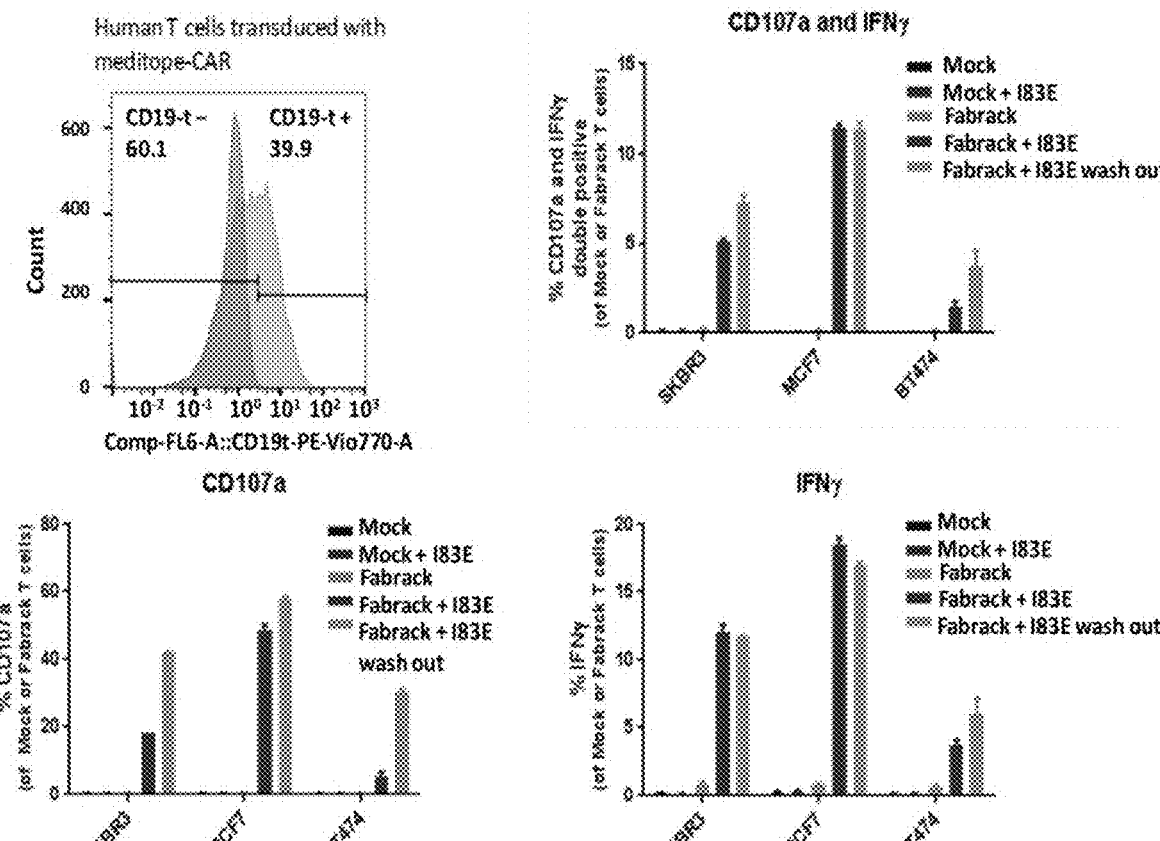

FIG. 28. The figure shows histogram of CD107a and IFN-g expression in T cells. Flow cytometry showed around 40% of human T cells were successfully transduced with meditope-CAR. FabRack T cell had increased expression of CD107a and IFNγ when cancer cells were incubated together with memAb trastuzumab pre-mix and wash or in the continuous presence of memAb trastuzumab. To analyze CD107a and IFNγ expression, Cancer cells (5×10$^4$/100 ul) were seeded in 96-well round-bottom plate and human T Morck or FabRack cells (5×10$^4$/100 ul) were added to each well with existing cancer cells. The ratio of effector to target is 1:1. CD107a-FITC (BD #555800) antibody and trans-porter inhibitor Golgistop (BD #554724) were added to each well during incubation. After 5 h incubation, cells were stained with fixable viability dye (Thermo Fisher Scientific #L34965) at 4° C. for 30 min in the dark. After washed twice, cells were stained with CD4-PerCP (BD #347324), CD8-APCCy7 (BD #348793) and CD19-PECy7 (BD #557835) at 4° C. for 30 min in the dark. After washed twice, cells were fixed and permeabilized by BD Cytofix/Cytoperm kit (BD 554714) followed by staining intracellular IFN by IFN-APC (BD #554702) at room temperature for 30 min in the dark. After washed twice, cells were resuspended at 100 ul final volume and 40 ul of samples were analyzed by flow cytometer.

Figure 29:
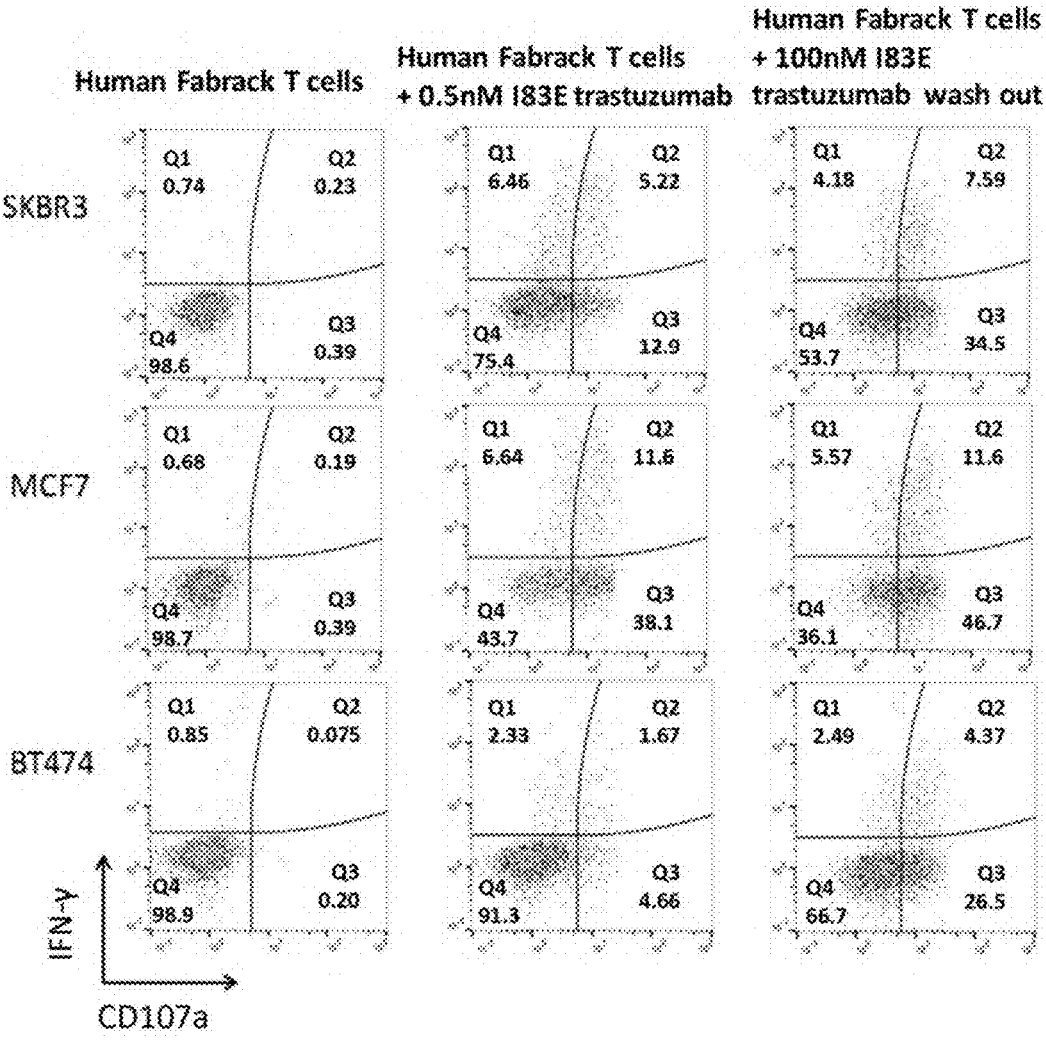

FIG. 29. The figure shows CD107a and IFN-γ.

Figure 30:
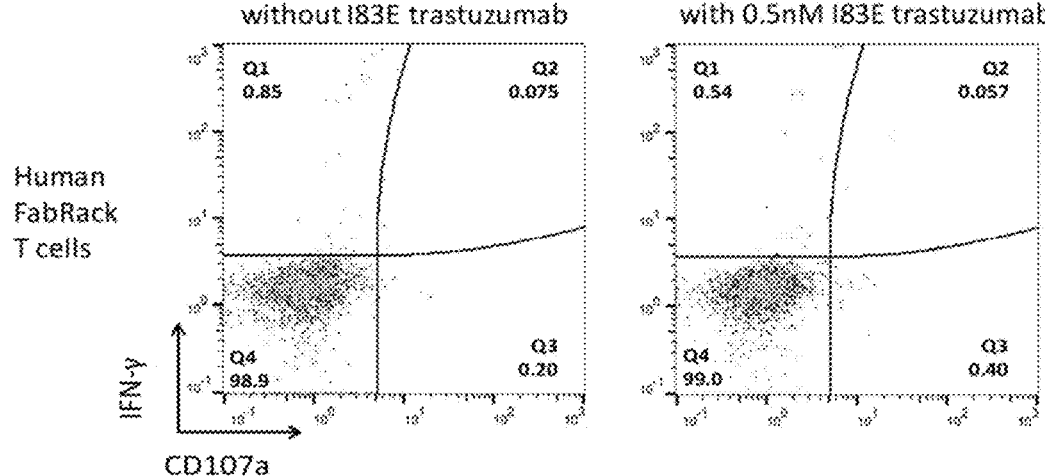

FIG. 30. The figure shows I83E trastuzumab cannot activate FabRack T cells without target cells. Activation marker available for testing: Up-regulation CD69 (short lived), CD137 (4-1BB), CD44, CD27, CD45RO, CD154;

Down-regulation CD62L, CCR7 (CD197) (CD25, CD69, CD137 (4-1BB), KLRG, CD62L, CD45RO, CD27, CD28). FabRack T cell did not show increased expression of CD107a and IFNγ when incubated with 0.5 nM memAb trastuzumab for 5 hrs.

Figure 31:
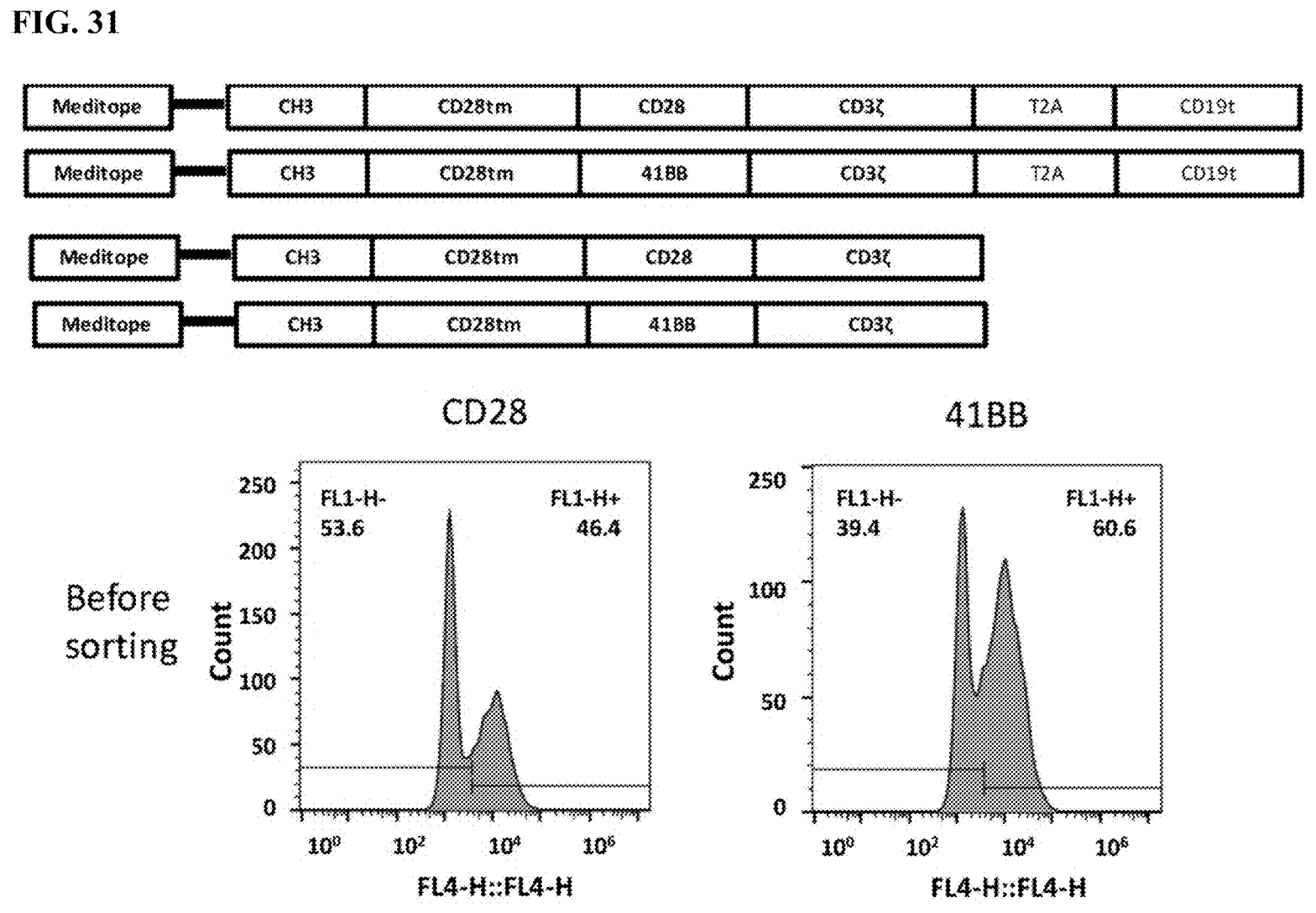

FIG. 31. Four constructs were generated. The top two schematics include a truncated CD19 gene to be used as a marker for transformed cells. These two differ by the co-stimulatory signal, C28 or 41BB. The bottom two schematics are the same minus the CD19 readout marker.

Figure 32:
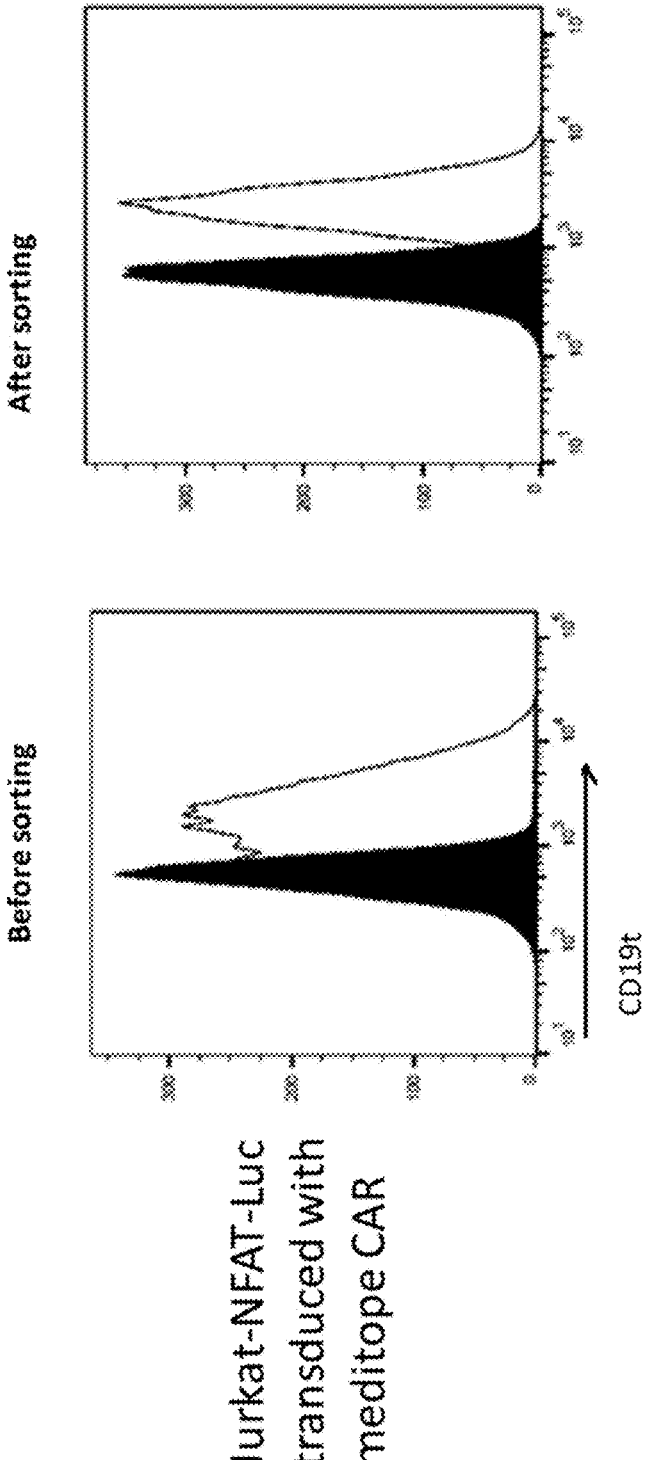

FIG. 32. Histograms of truncated CD19 (CD19t) expression in Jurkat-NFAT-Luc cells before and after sorting. Cells were stained with CD19-PE-Cy7 and CD19t positive were sorted out by BD Aria SORP flow cytometer. A homogeneous population of transformed cells isolated by cell sorting using the truncated CD19 marker.

Figure 33A:
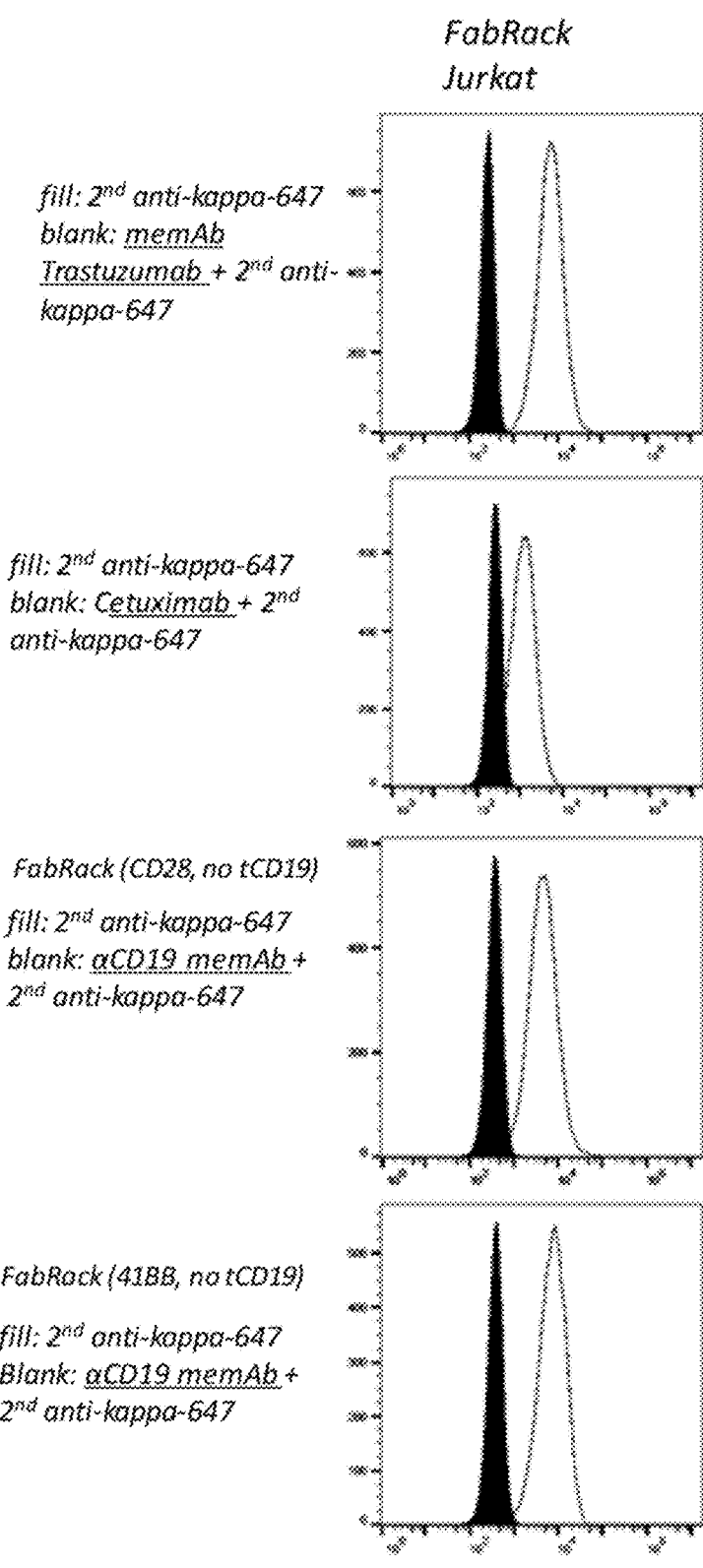
Figure 33B:
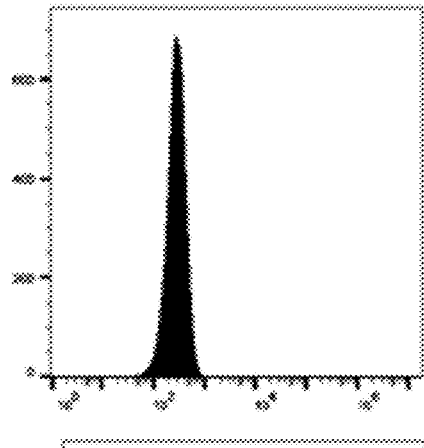
Figure 33B:
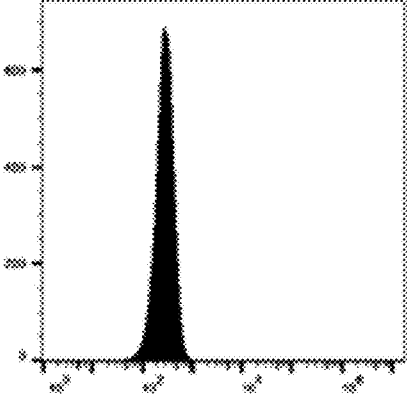
Figure 33C:
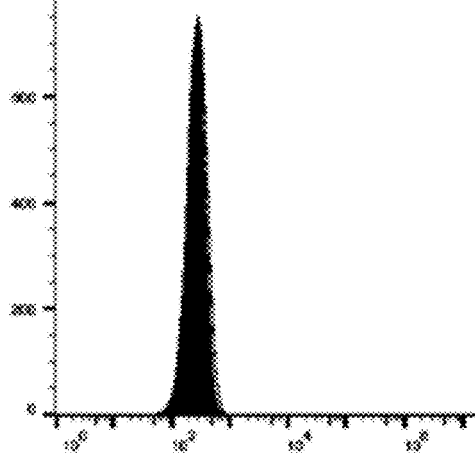

FIGS. 33A-33C. Take home: FIG. 33A) Meditope-enabled IgG only binds to one of the four variants (with or without CD19t and either CD28 or 41BB co-stimulatory signals). FIG. 33B) Non-transformed Jurkat cells do not bind to the IgG. FIG. 33C) Likewise, parental antibodies (e.g., NOT meditope-enabled) do not bind to the FabRack Jurkat cells. In other words, different memAbs can be combined with different Fabrack variants.

Figure 34:
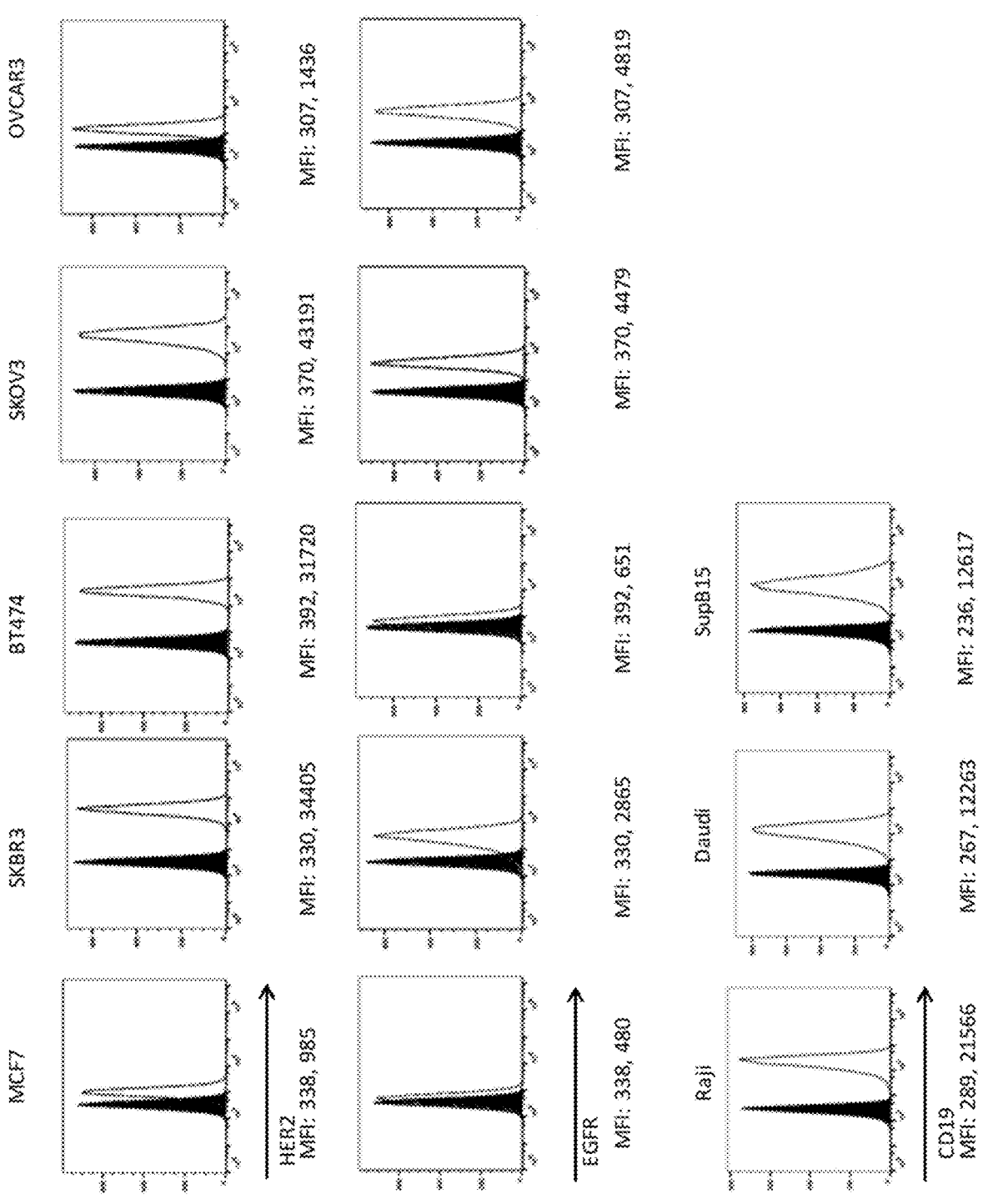

FIG. 34. Breast (MCF7, SKBR3 and BT474) or ovarian (SKOV3 and OVCAR3) cancer cell lines were shown memAb binding to HER2 or EGFR. Median fluorescence intensity (MFI) of cells with or without memAb binding is shown under respective graphs. Her2, EGFR and CD20 antigen density was independently quantified over a series of cell lines using analytical cytometry that we use subsequently to broadly test the ability to switch the antigen specificity and efficacy of the Fabrack.

Figure 35:
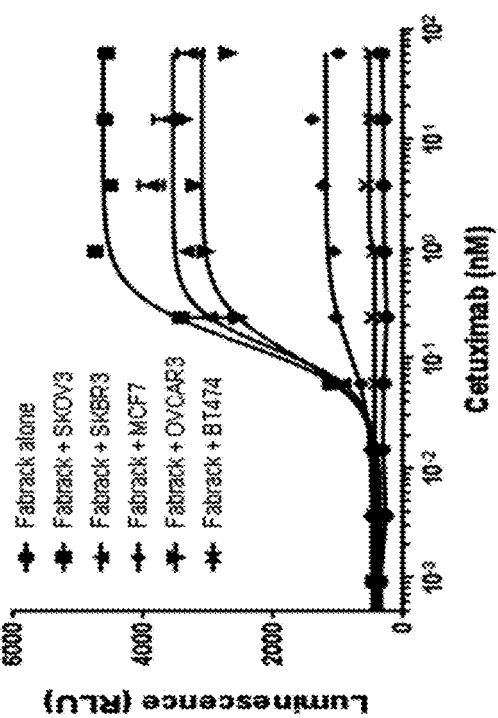
Figure 35:
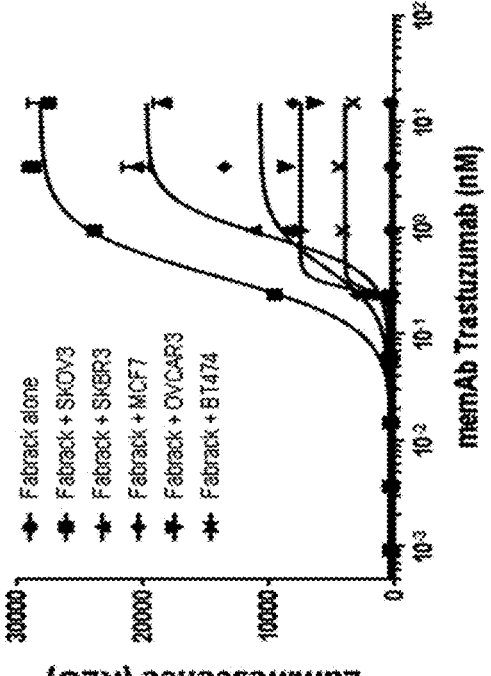

FIG. 35. Breast or ovarian cancer cells (2.5 E4) were seeded in 96-well white-wall plate. After cell attachment for overnight, media in the plate was removed and Jukat-NFAT-Luc Fabrack cells (CD28 version, 1E5) with various doses of memAb (anti-HER2 or anti-EGFR) were added to each well. Cells were incubated at 37° C. for 6 hr followed by addition of luciferase substrate (Invivogen #rep-qlc2) to each well. The luminescence was immediately measured using Biotek's Synergy 4 multi-detection microplate reader. The 'EC50' is less than 1 nM for all cells, however, the plateau differs greatly. The increase correlates with antigen expression except for BT474 cells. This exception requires further study (Her3 or other molecules interfering?). A similar trend is observed for EGFR in the right panel. Using cetuximab, the MFI is 651 for BT474; 480 for MCF7; 4819 for OVCAR3; 2865 for SKBR3; and 4479 for SKOV3. While BT474 express slightly more EGFR than MCF7, the trend in the plateau tends to follow antigen density. Some of the properties of the BT474 cell line can be found at website ncbi.nlm.nih.gov/pmc/articles/PMC3236329/.

Figure 36:
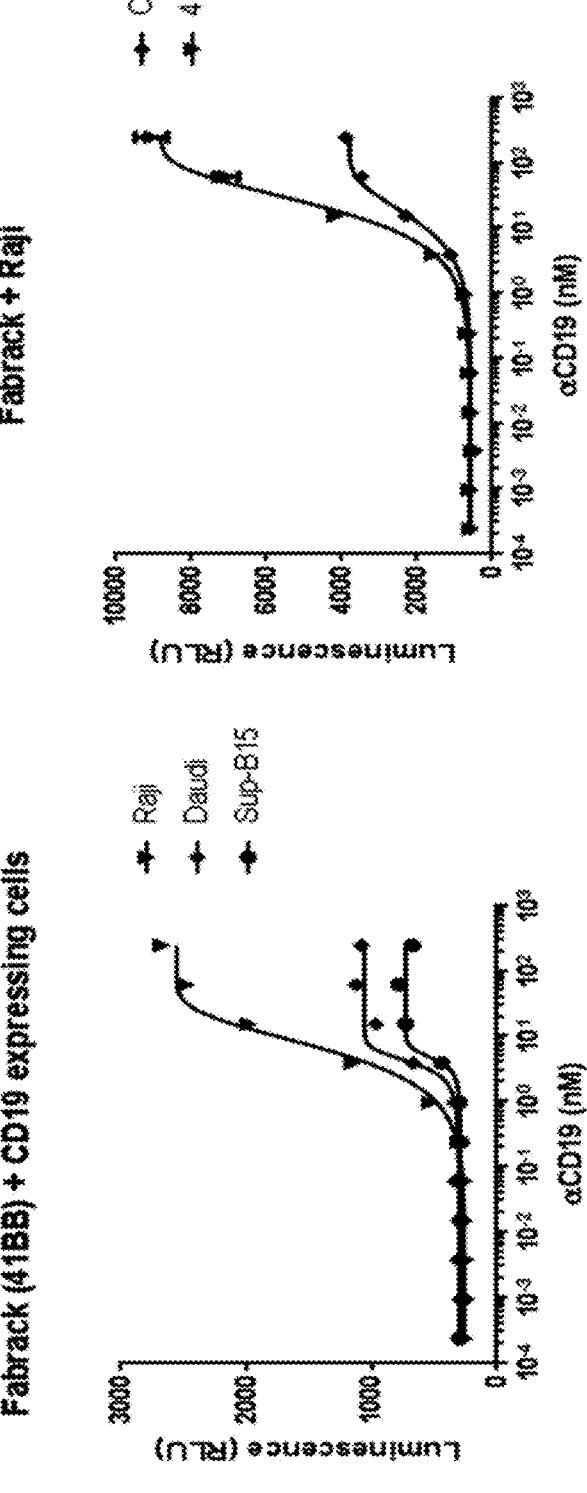

FIG. 36. CD19 expressing cancer cells (5 E4) were seeded in 96-well white-wall plate and in coculture with Jukat-NFAT-Luc Fabrack cells (41BB or CD28 version, 1E5) with various doses of CD19 memAb. Cells were incubated at 37° C. for 6 hr followed by addition of luciferase substrate (Invivogen #rep-qlc2) to each well. The luminescence was immediately measured using Biotek's Synergy 4 multi-detection microplate reader. Left panel shows different CD19 expressing cells can be targeted. The plateau varies with antigen density. The MFI for Raji is 21566; for Daudi it is 12263; for Sup-B15 it is 12617. The right panel indicates that the CD28 activation signal is stronger than the 41BB.

9

Figure 1A:
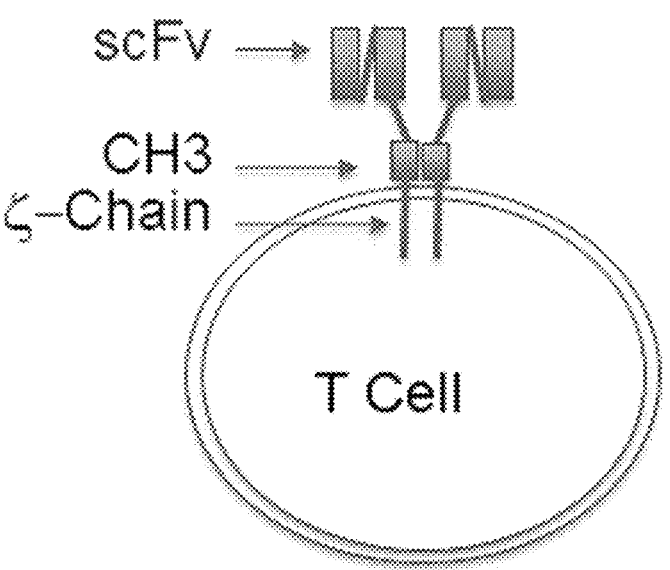
FIG. 1A-1C.
Figure 1B:
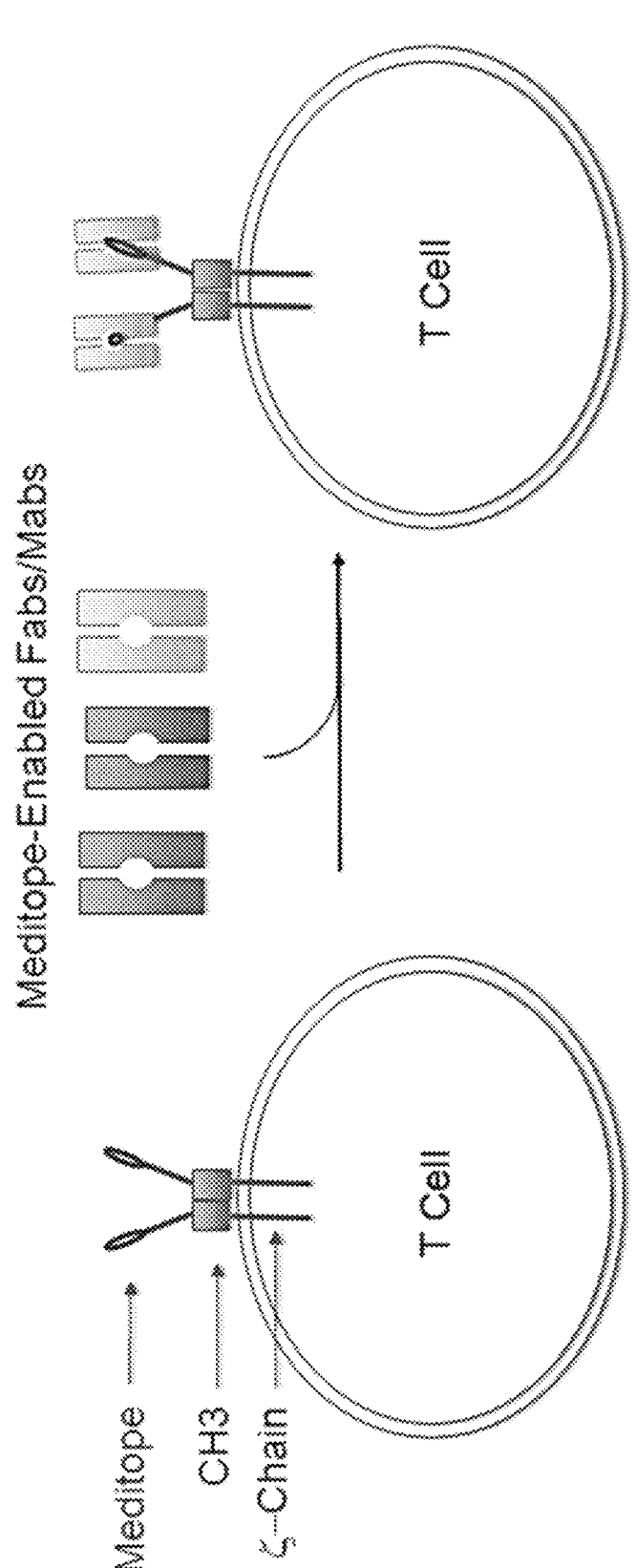
Figure 1C:
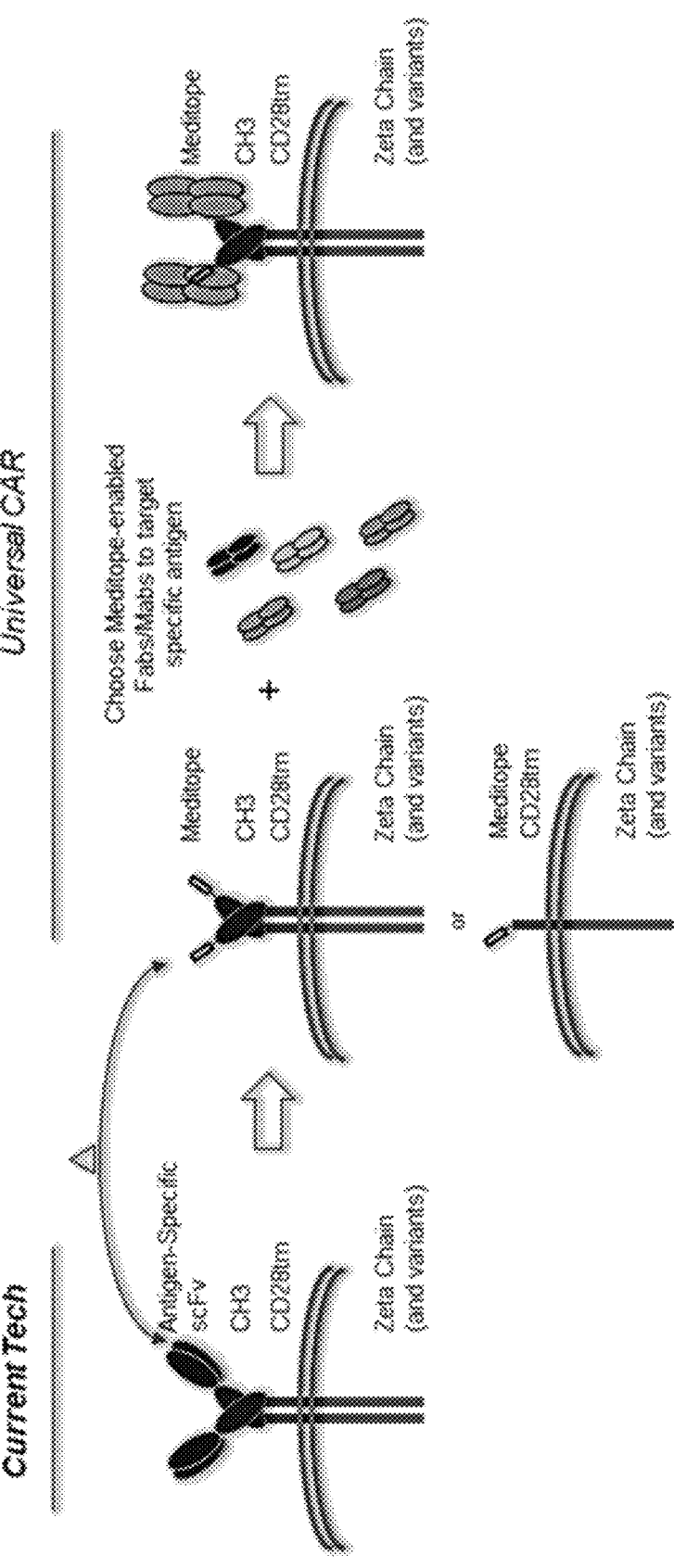
Figure 3A:
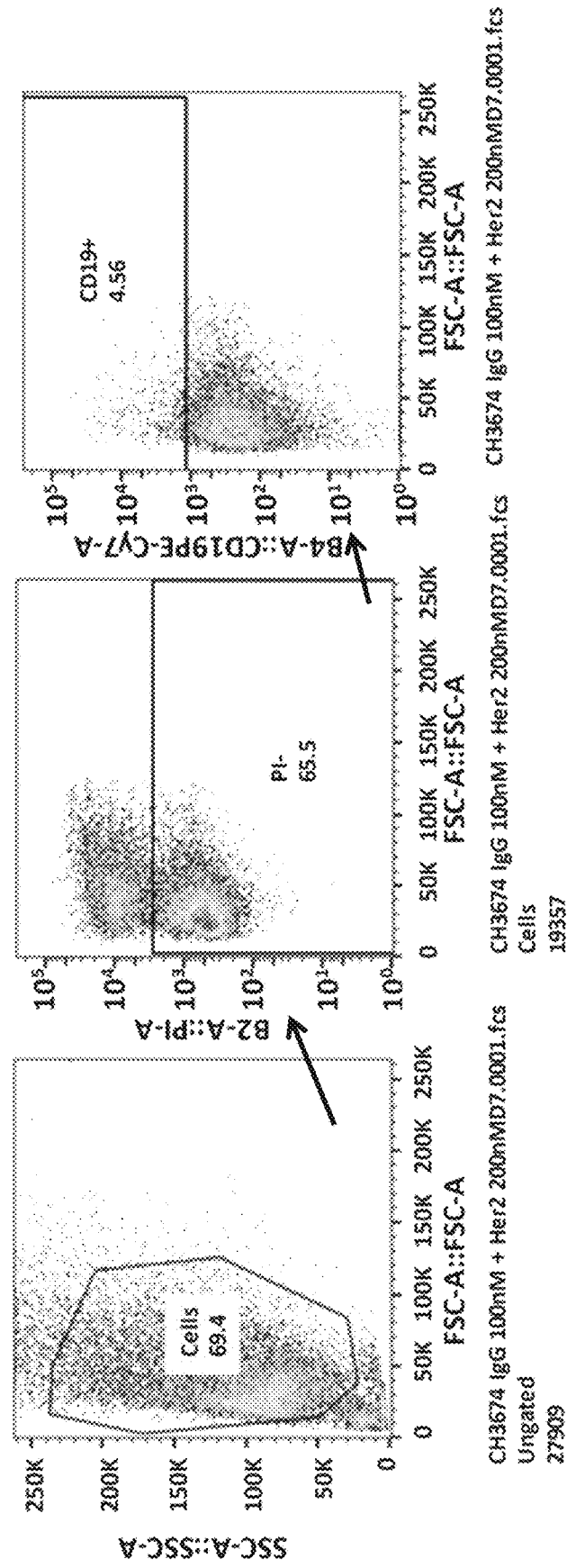
FIG. 3A-3B. Gating strategy for flow cytometry analysis.
Figure 3B:
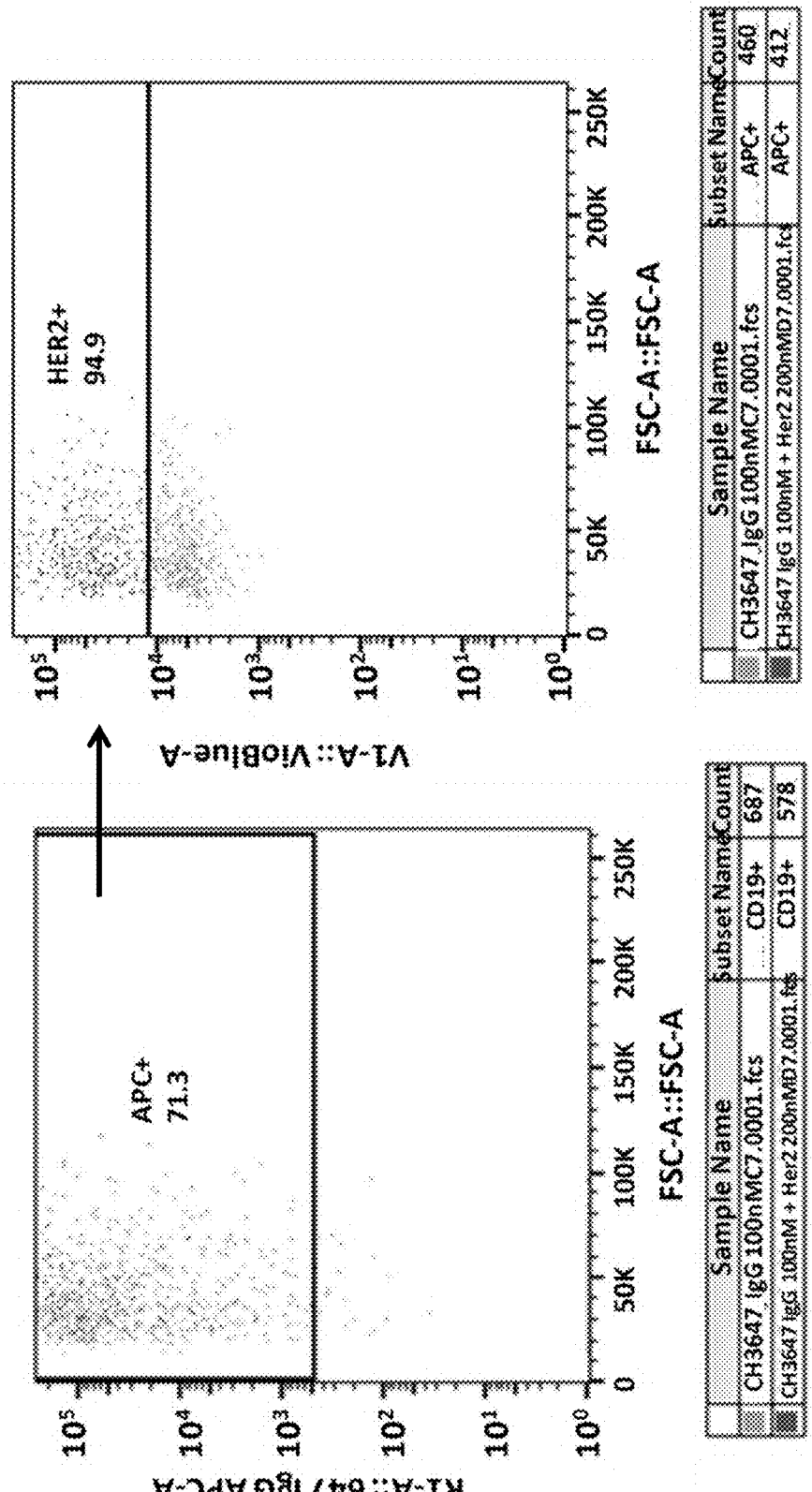
Figure 4A:
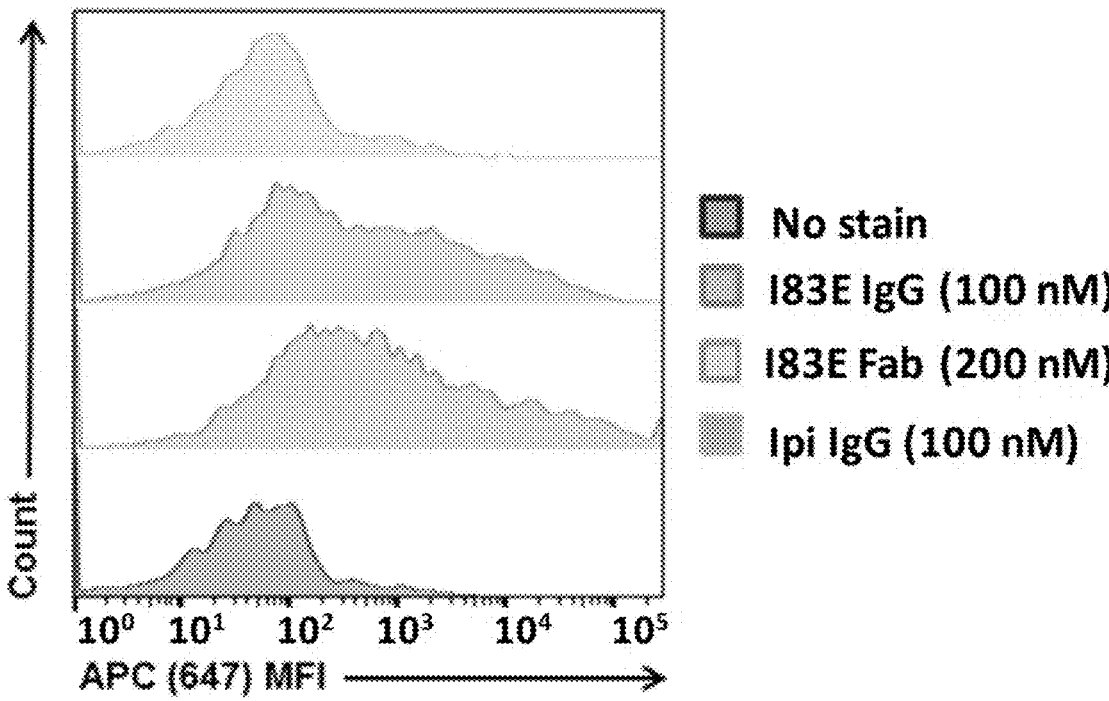
FIG. 4A-4C. Meditope-enabled IgG and Fab binds Meditope-CH3 CAR.
Figure 4B:
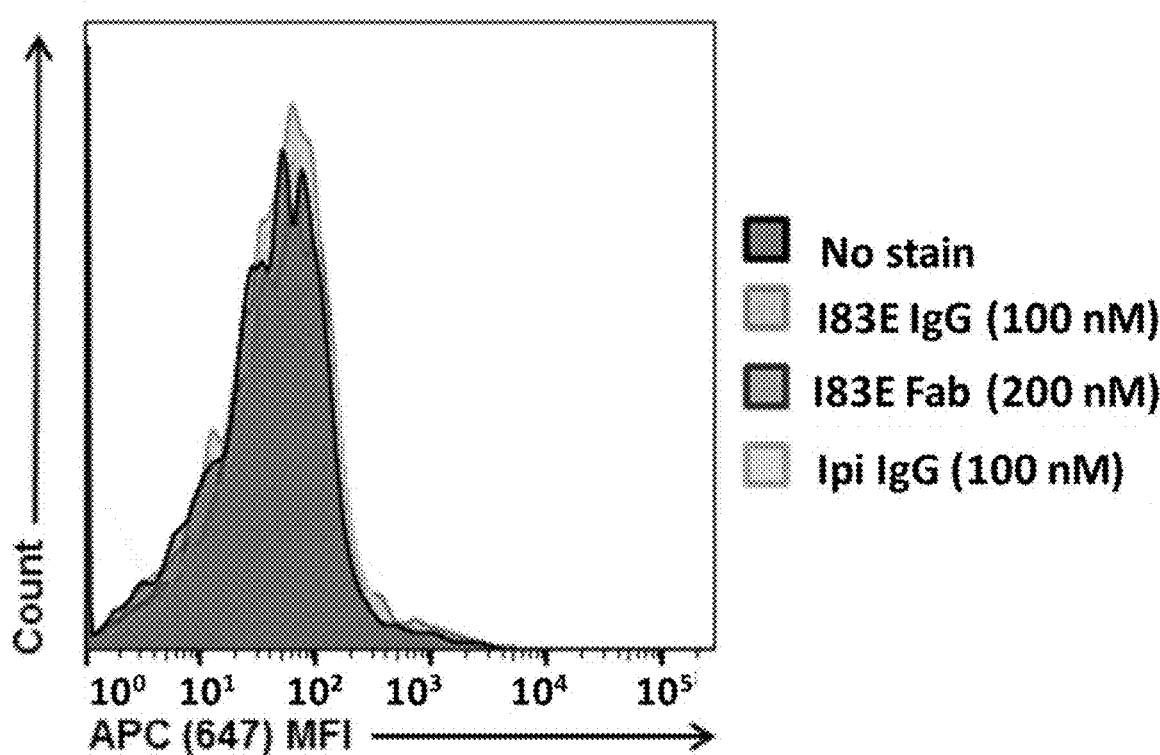
Figure 4C:
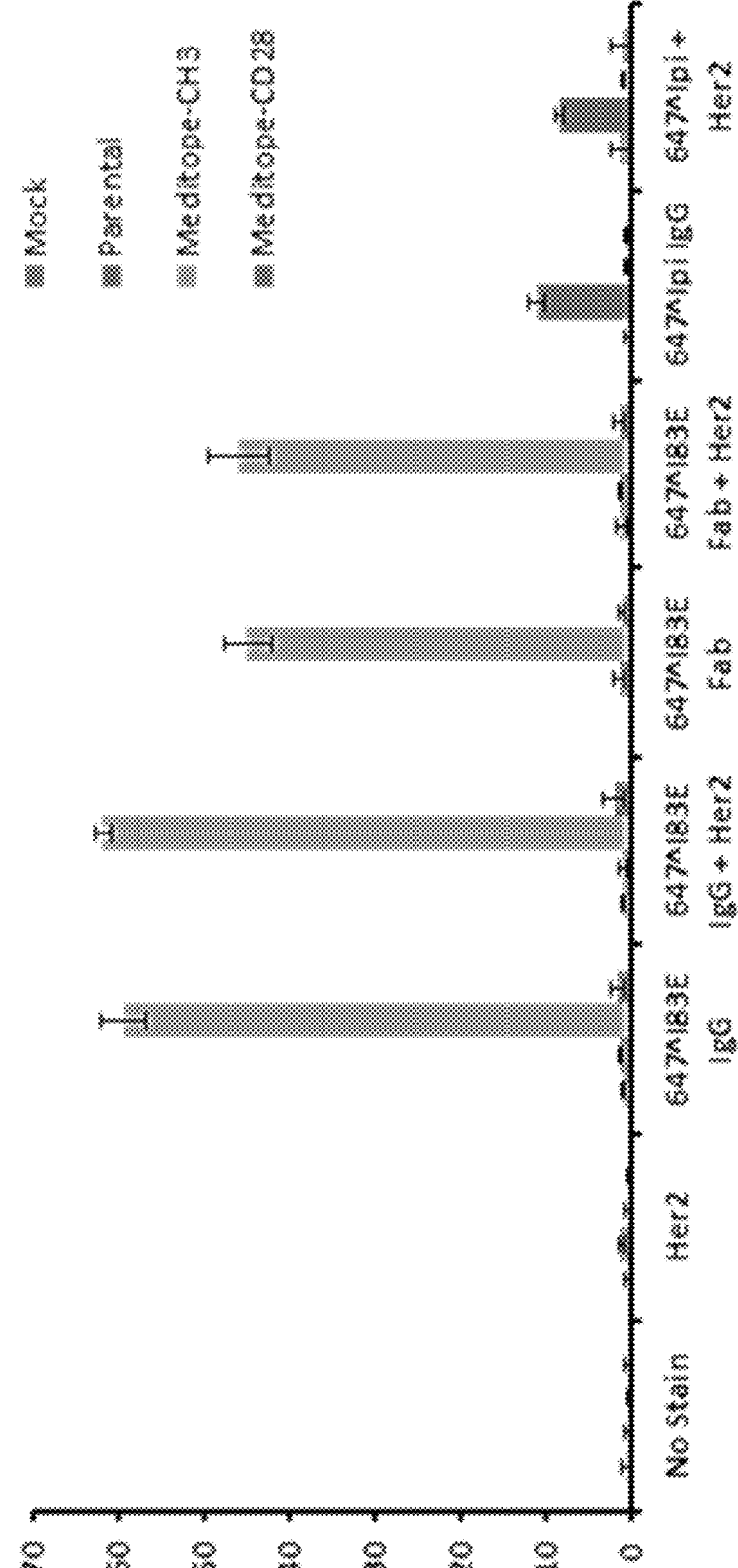
Figure 5A:
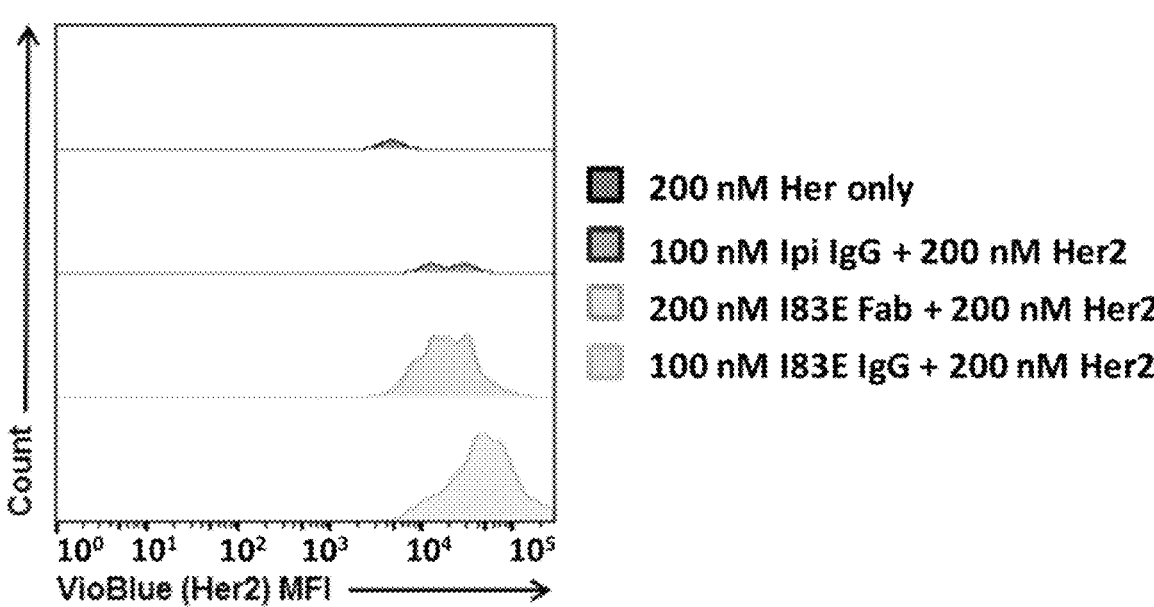
FIG. 5A-5B. Meditope-CH3 expressing cells bind meditope-enabled antibody, which can subsequently bind antigen.
Figure 5B:
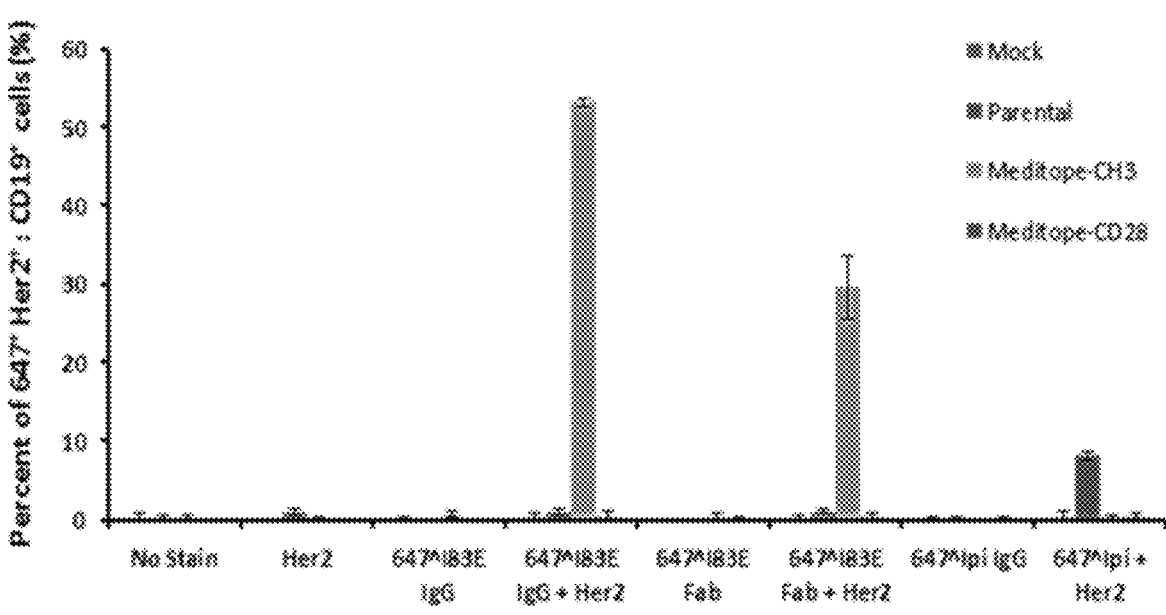
Figure 6A:
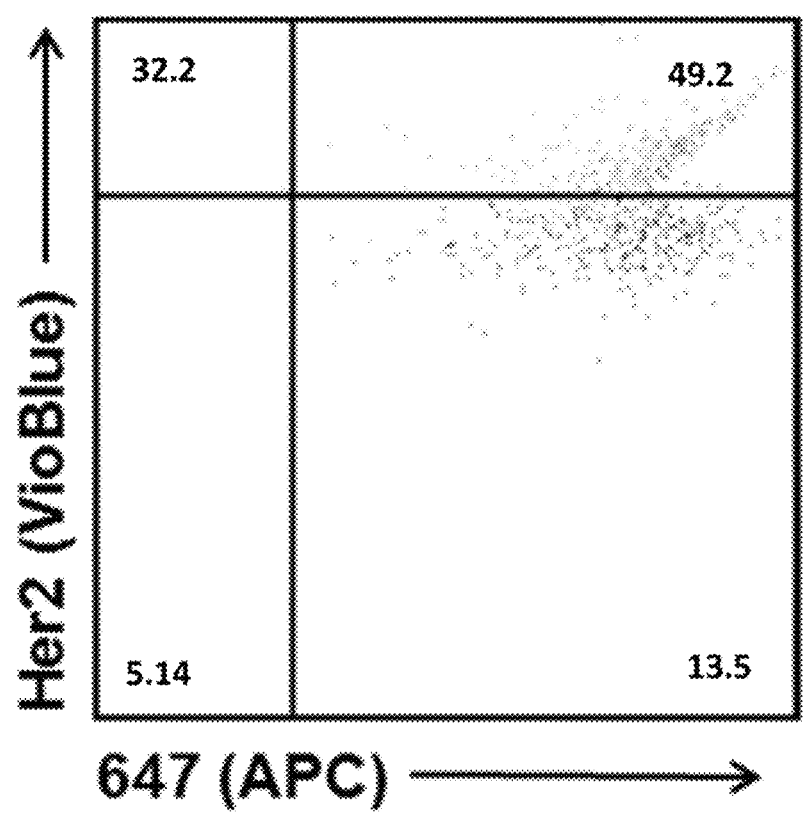
FIG. 6A-6C. Identification of 647$^+$ Her2$^+$ double-positive cells. Live transfected cells were identified using FSC/SSC→PI$^-$→CD19$^+$ gating (See FIG. 3A). Cells were then analyzed for 647 (x-axis) and Her2 levels (VioBlue). Of note, many 647$^-$ cells are on the y-axis.
Figure 6B:
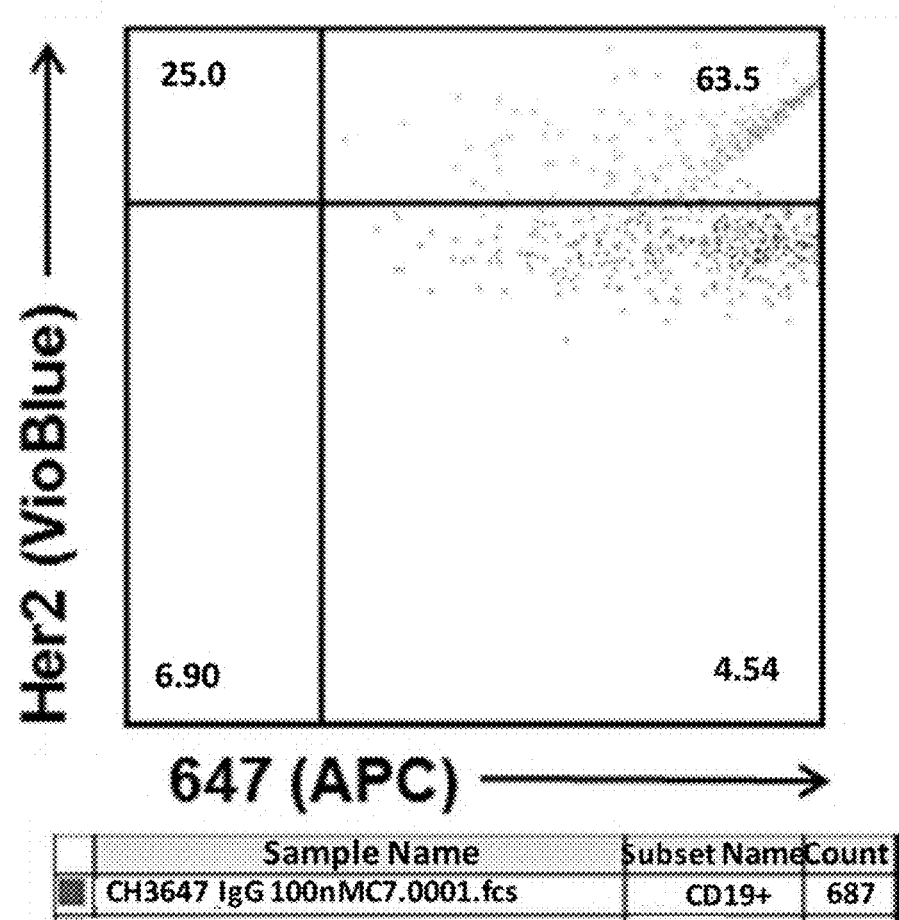
Figure 6C:
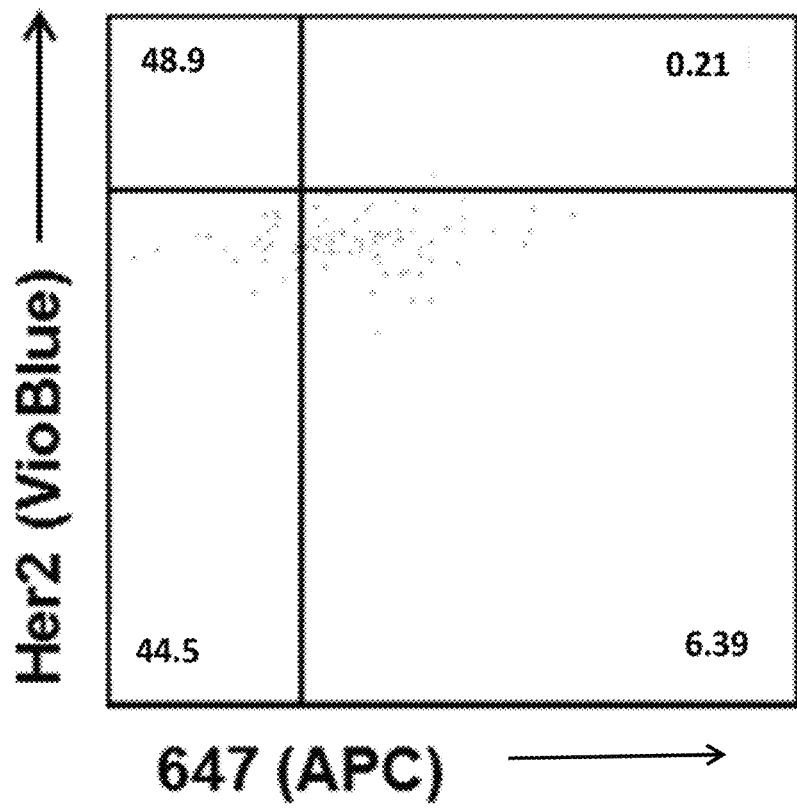
Figure 7:
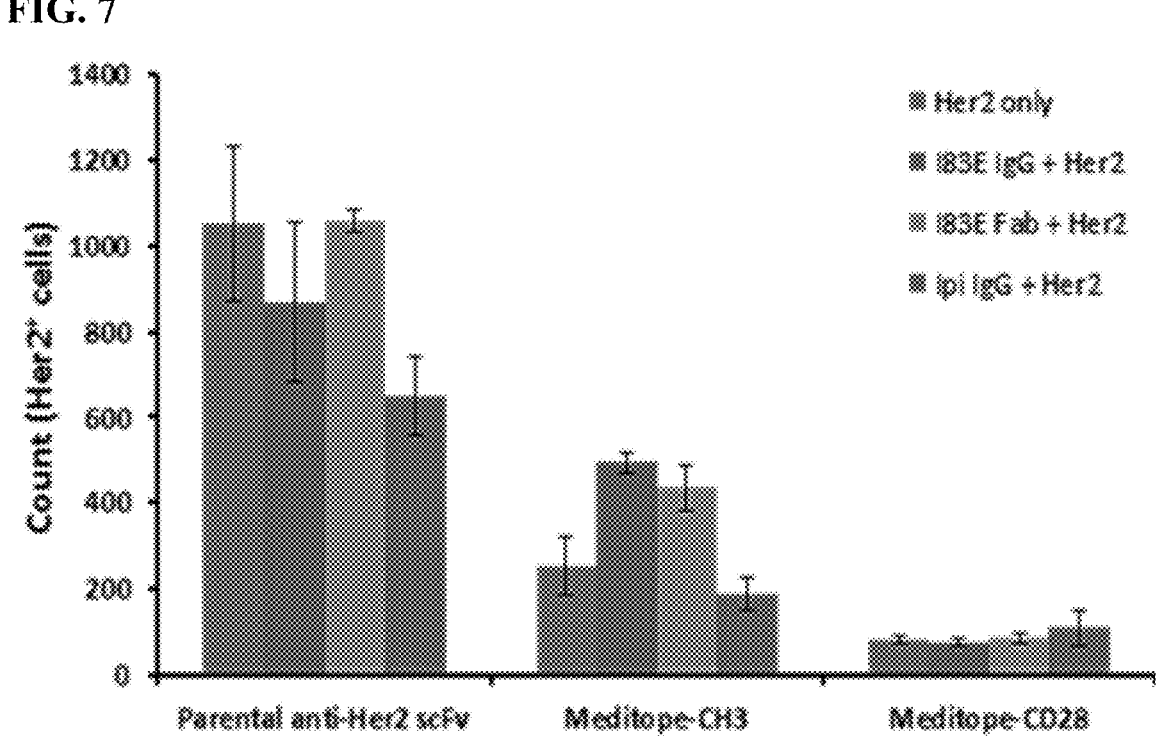
FIG. 7. Identification of Her2$^+$ cells. Live transfected cells were identified using FSC/SSC→PI$^-$→CD19$^+$ gating. Next gate was drawn using analyses from samples without PacBlue^Her2 to identify Her2$^+$ cells. Cells were then analyzed for Her2 (VioBlue) levels.
Figures 8A, 8B:
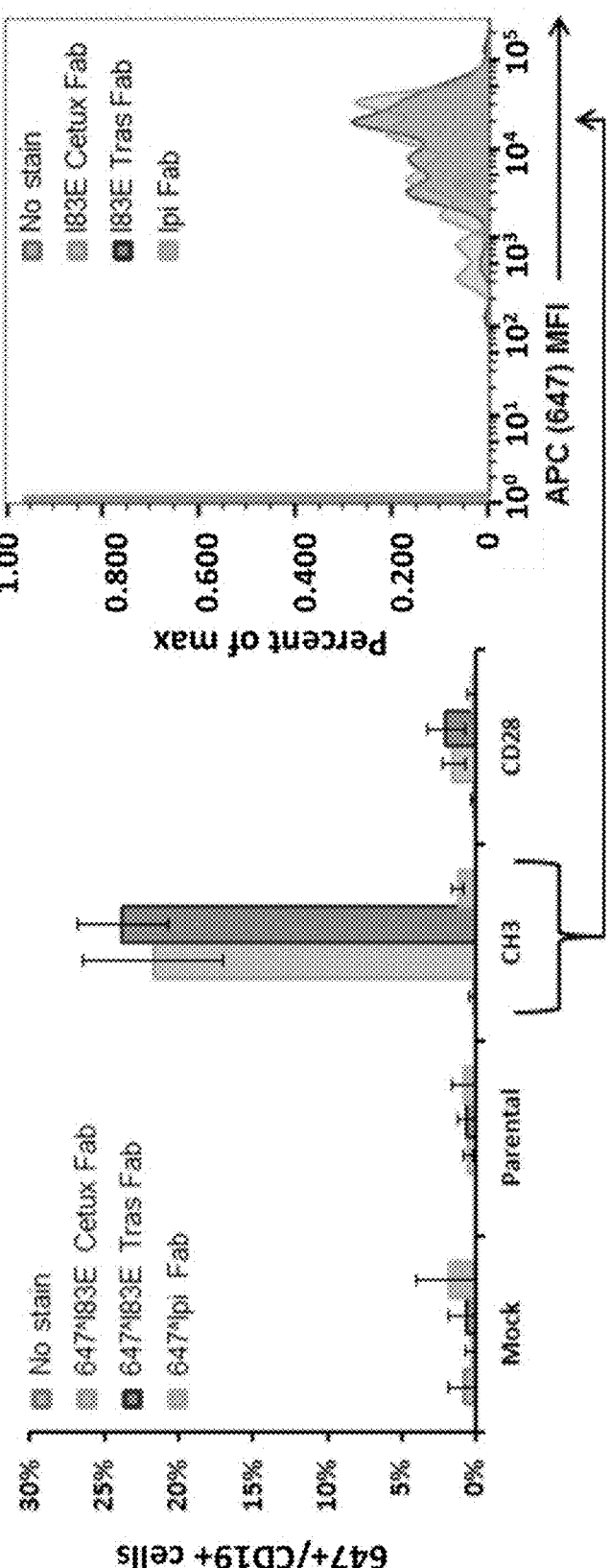
FIG. 8A-8B. Meditope-enabled cetuximab and trastuzumab Fabs bind Meditope-CH3 CAR.
Figure 9A:
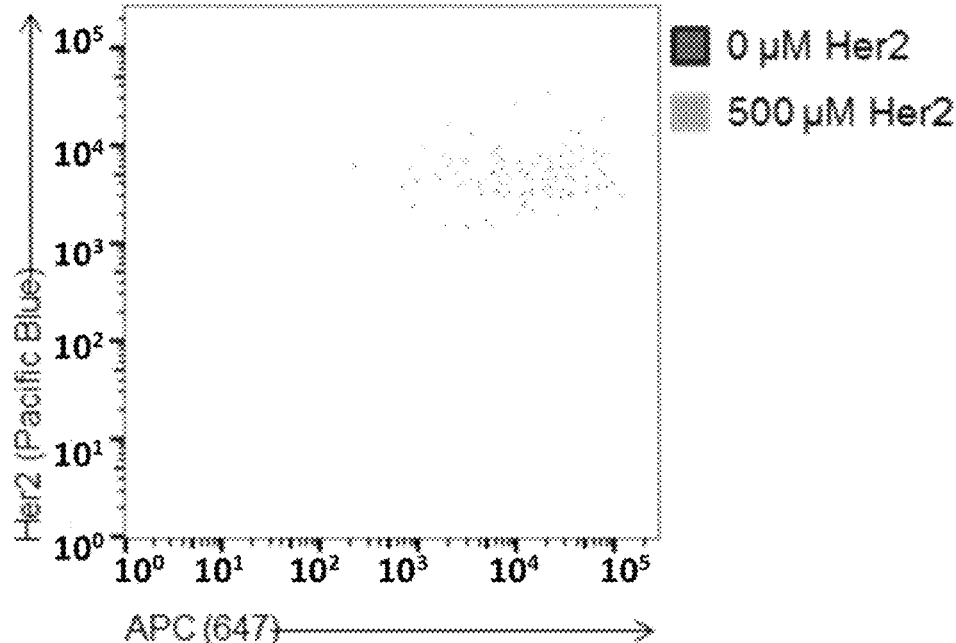
FIG. 9A-9B. Identification of 647$^+$ Her2$^+$ double-positive cells. Live transfected cells were identified using FSC/SSC→PI$^-$→CD19$^+$ gating. Cells were then analyzed for 647 (x-axis) and Her2 levels (Pacific Blue).
Figure 9B:
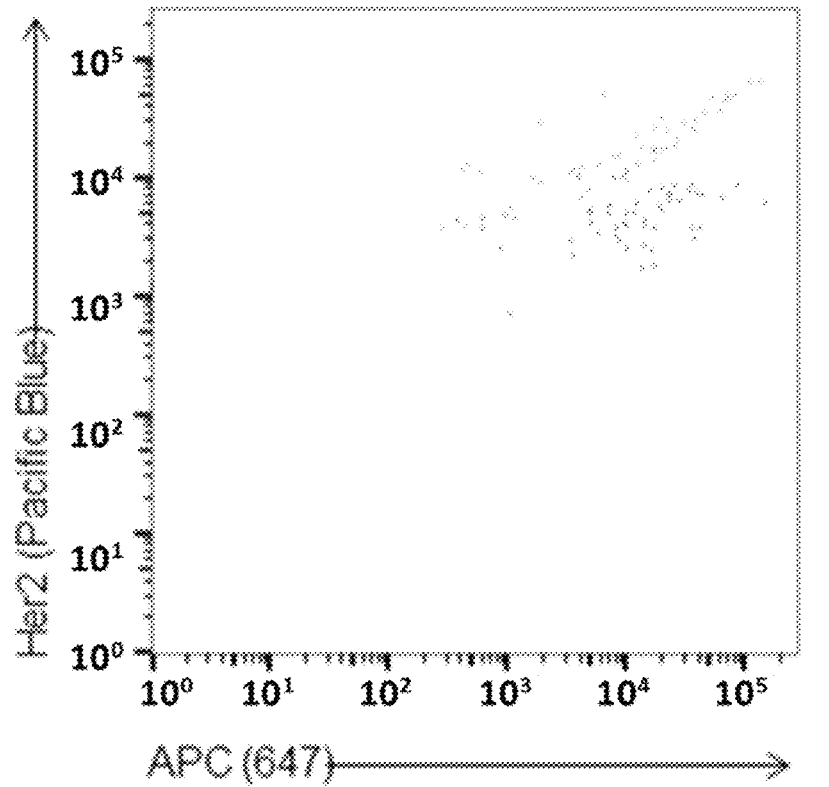
Figure 10:
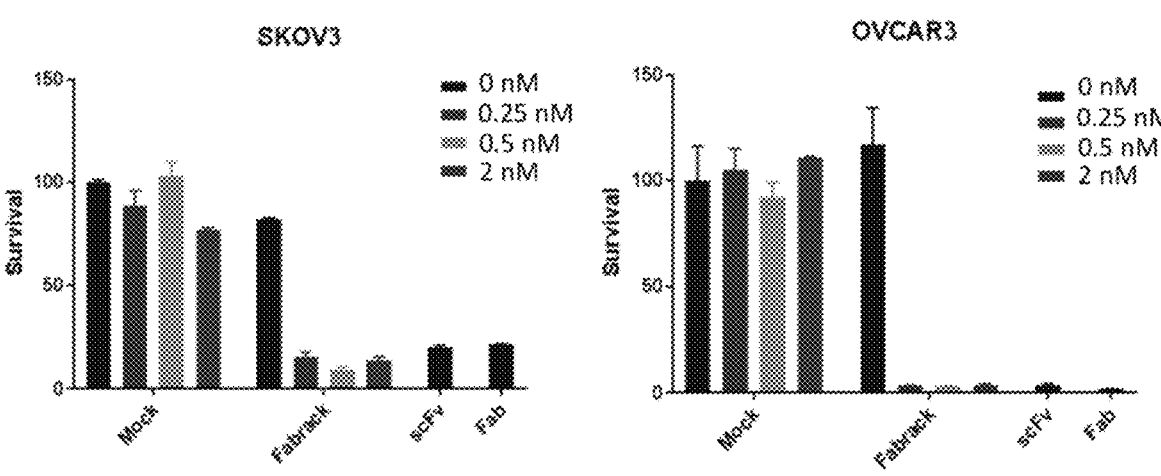
FIG. 10. The figure shows tumor killing assay in ovarian cancer cell lines using different concentrations of meditope-enabled Her2.
Figure 11:
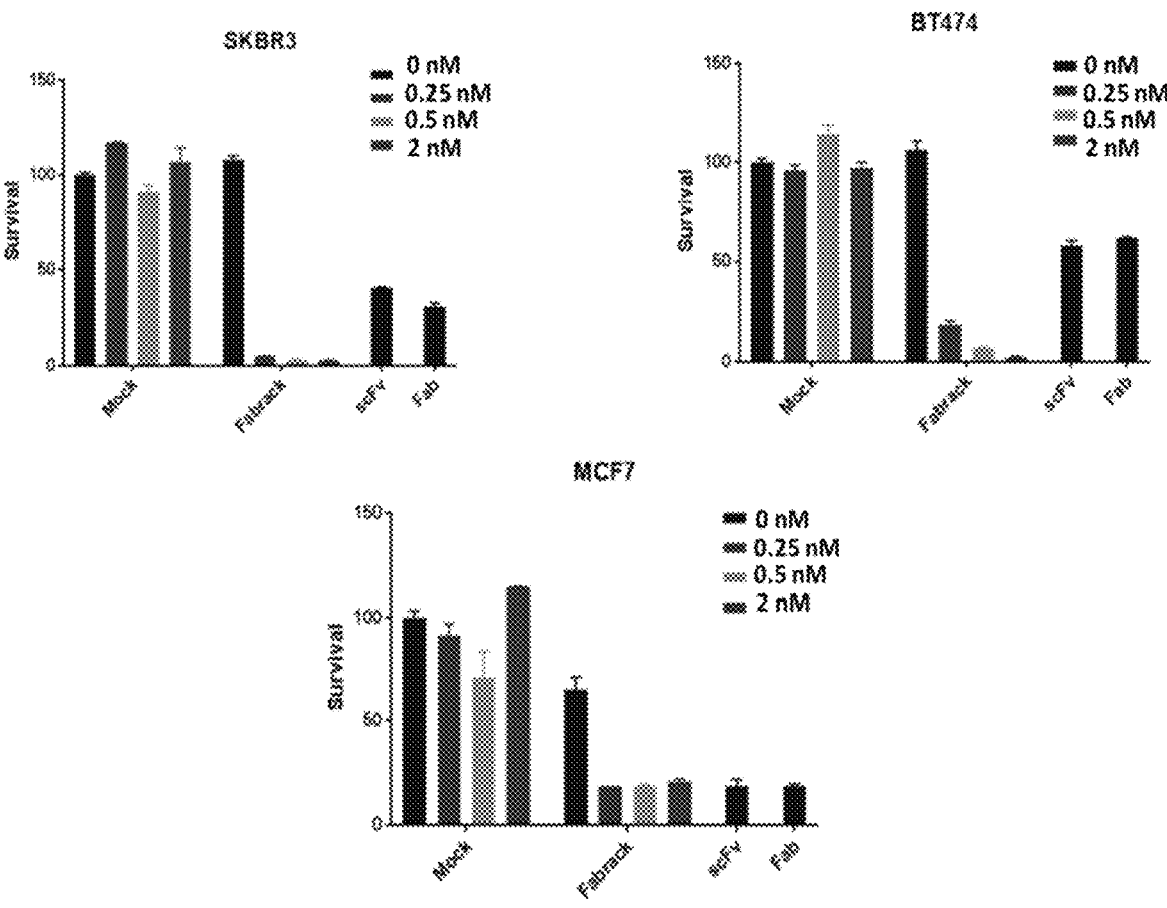
FIG. 11. The figure shows tumor killing assay in breast cancer cell lines using different concentrations of meditope-enabled Her2.
Figure 12:
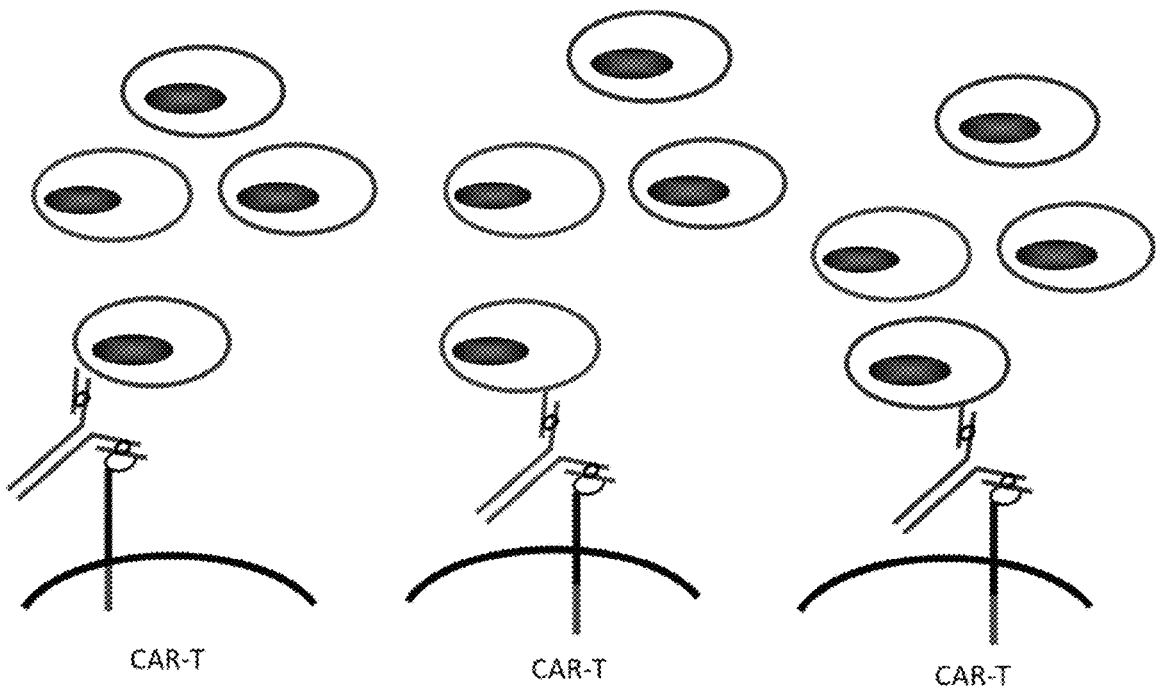
FIG. 12. The figure shows FabRack T cells.
Figure 13:
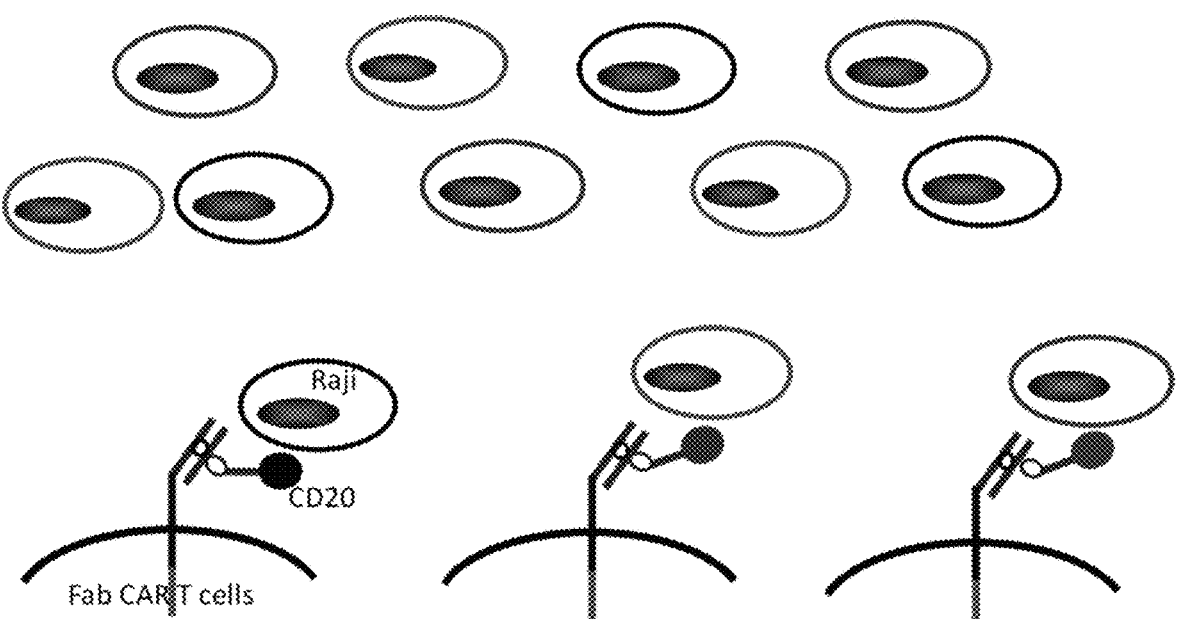
FIG. 13. The figure shows switchable Fab CAR-T cells.
Figure 14:
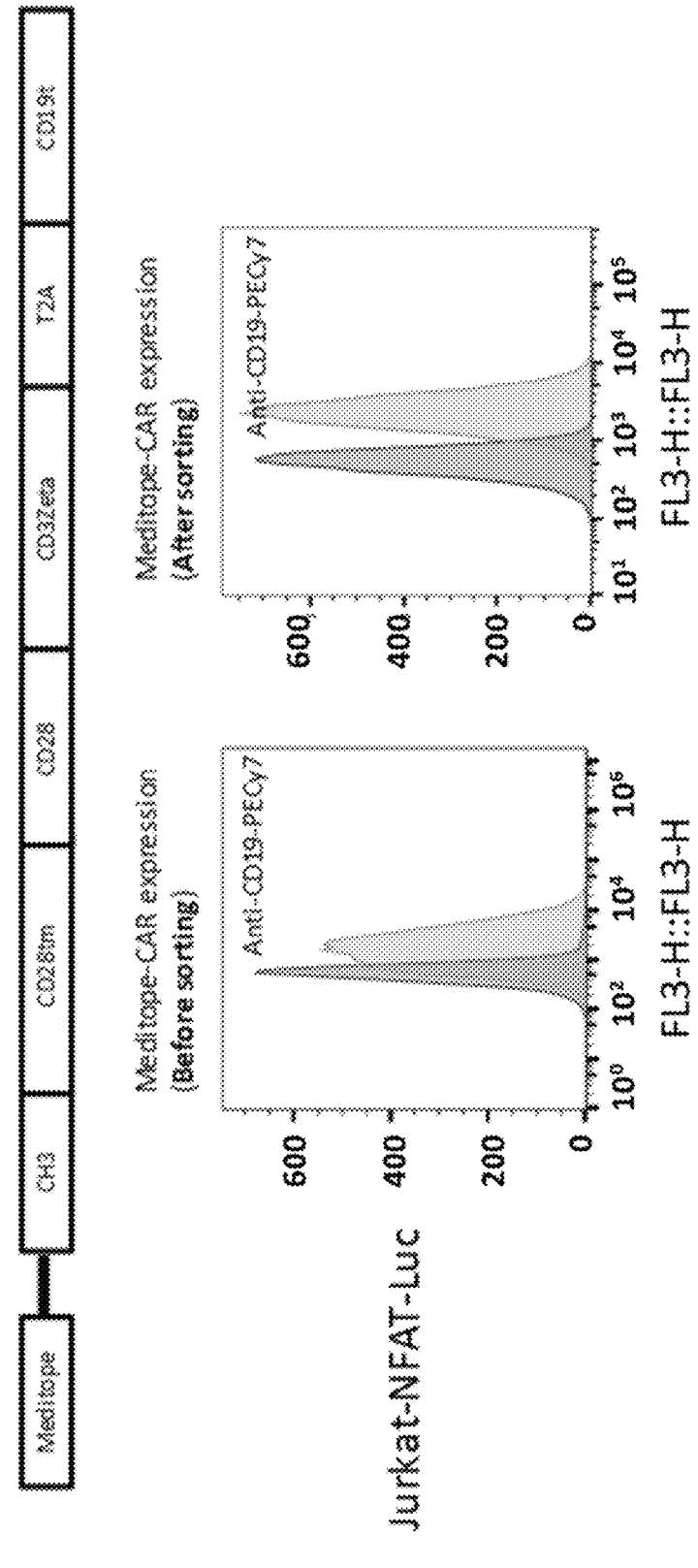
FIG. 14. Jurkat cells were transduced with meditope-CAR and truncated CD19 was co-expressed as a marker. After transduction, cells with CD19 positive were sorted out and expanded for the following experiment.
Figure 15:
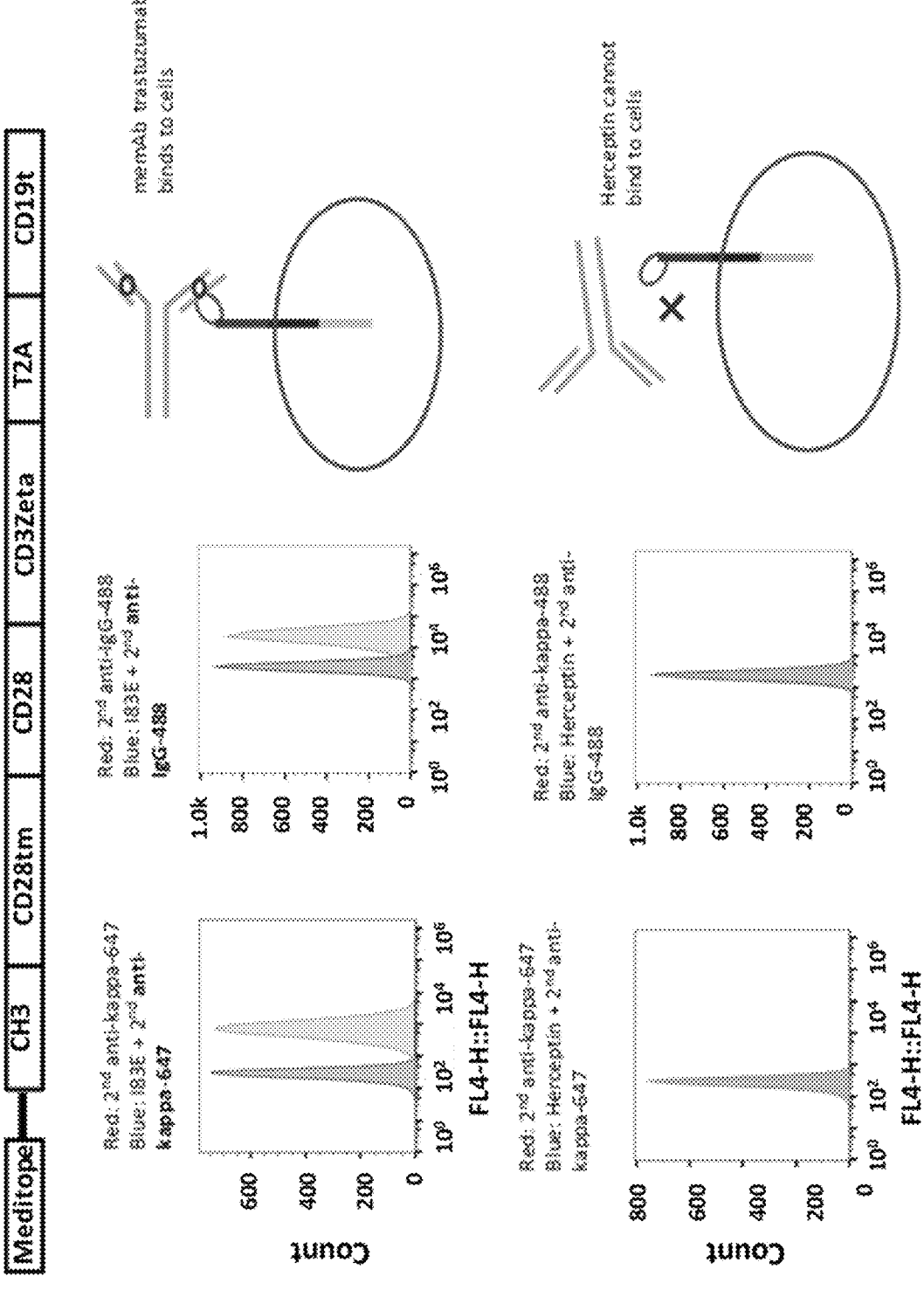
FIG. 15. Meditope-CAR expressing Jurkat cells were incubated with trastuzumab with or without meditope site and then stained with secondary anti-kappa-647 (Abcam
Figure 37:
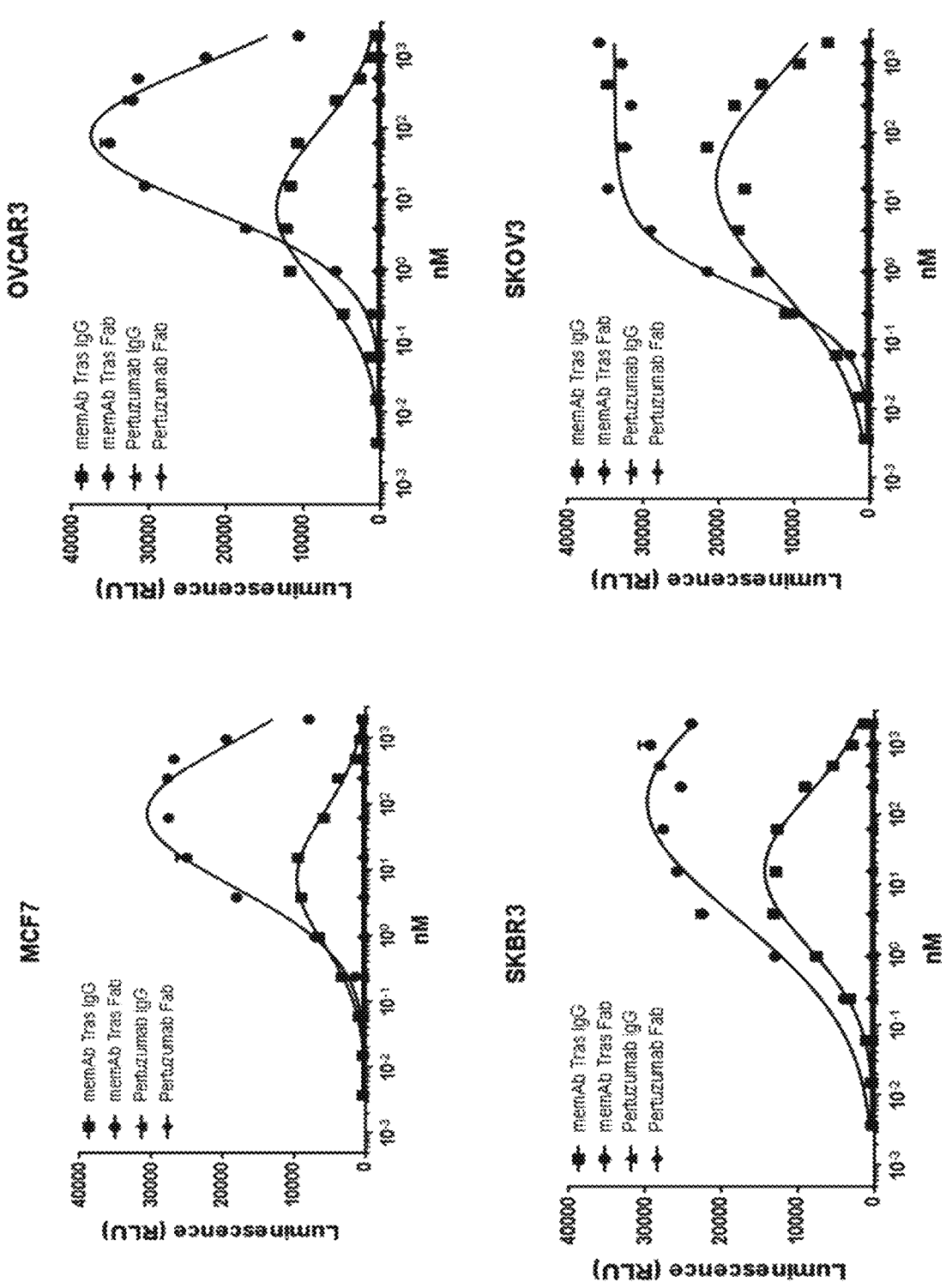

FIG. 37. Activation of FabRack Jurkat cells in the presence of memAb and target cells. Different doses of memAb trastuzumab IgG of Fab are present in the well containing FabRack Jurkat cells and target cells for 6 hr. At the end of incubation, luciferase substrate was added in each well and luminescence was immediately read by plate reader. Breast or ovarian cancer cells (2.5 E4) were seeded in 96-well white-wall plate. After cell attachment for overnight, media in the plate was removed and Jukat-NFAT-Luc Fabrack cells (CD28 version, 1E5) with various doses of memAb trastuzumab or non-memAb pertuzumab were added to each well. Cells were incubated at 37° C. for 6 hr followed by addition of luciferase substrate (Invivogen #rep-qlc2) to each well. The luminescence was immediately measured using Biotek's Synergy 4 multi-detection microplate reader. Based on our FACS data, MCF7 expresses lowest amount of Her2 (MFI=985). OvCAR3 express slightly more (MFI=1435). SKBR3 (MFI=34405) and SKOV3 (MFI=43191) express considerable more than MCF7 and OvCAR3. Pertuzumab which also binds to Her2 is not meditope enabled but does contain an Fc. The fact that it does not indicates that the meditope-enabled Fab/Mab is required (as predicted). Hook effect is active in all cell lines using the IgG format. This effect sets in early for cells with 'lower' antigen density (peak of 'fit' is less than 10 nm for MCF7 and OvCAR3 and greater than 10 nM for SKBR3 and SKOV3). This finding is consistent with cell derived antigen being saturated at lower concentrations. Valency has a strong affect (e.g., the hook effect sets in at lower concentrations using the IgG {bivalent}compared to the Fab {monovalent}). Interestingly, the 'plateau' is much higher using the Fab. The fact that we see differences indicates that we can tune the properties of the memAb to optimize the affect. It also suggests that we can use the hook effect as a safety mechanism. N.b., in FIG. 8 and FIG. 9 the hook effect was not obvious. This is due in part to a lower range of concentrations used in those studies (the antibody concentration only went to 10 nM, here it is going to 1 uM). Information on Hook Effect can be found at website en.wikipedia.org/wiki/Hook_effect.

Figures 38, 39:
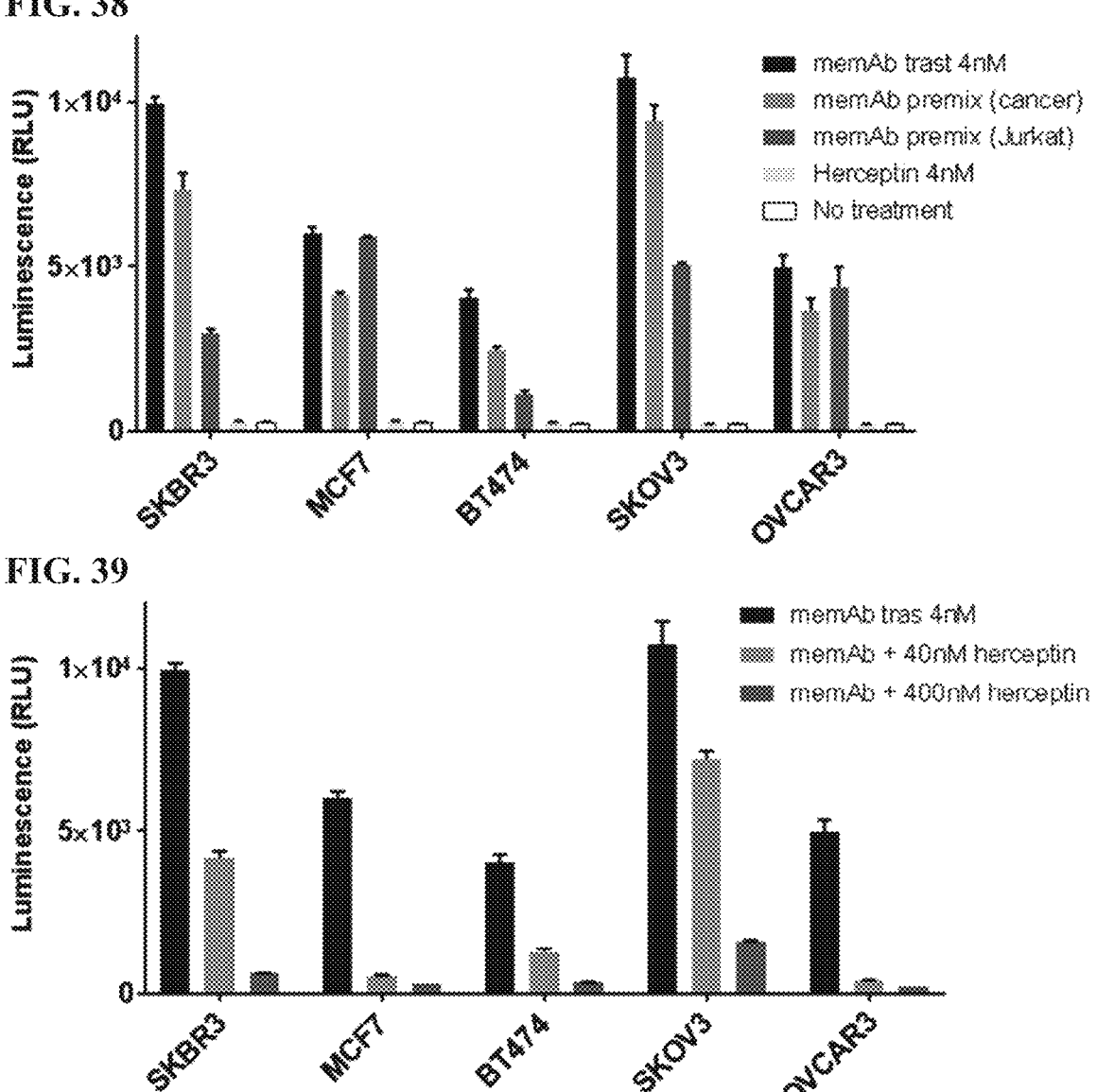

FIG. 38. Activation of FabRack Jurkat cells in coculture with cancer cells in the presence of 4 nM memAb trastuzumab, memAb trastuzumab pre-binding to target cells or memAb trastuzumab pre-binding to FabRack Jurkat cells. Cancer cells or FabRack Jurkat cells with 100 nM memAb trastuzumab pre-binding was followed by a washout. Activation level of FabRack Jurkat cells with 4 nM herceptin treatment is similar to no treatment. Method: Cancer cells (2.5×10⁴/100 ul) were seeded in 96-well white-wall plate. After cell attachment for overnight, media in the plate was removed and Jurkat-NFAT-Luc meditope-CAR cells (1×10⁵/ 60 ul) were added to each well. memAb Trastuzumab was continuously present or pre-bound to Jurkat-NFAT-Luc medi-CAR or cancer cells with wash. Bars in graph, from left to right, represent: memAb trastuzumab (4 nM) continuously present, FabRack Jurkat-NFAT-Luc cells with memAb trastuzumab (100 nM) pre-binding followed by a wash, cancer cells with memAb trastuzumab (100 nM) pre-binding followed by a wash, Herceptin (4 nM) continuously present, and no treatment. Cells were incubated at 37° C. for 6 hr followed by addition of 50 ul luciferase substrate (Invivogen #rep-qlc2) to each well. The luminescence was immediately measured using Biotek's Synergy 4 multi-detection microplate reader. In all cases, adding 4 nM of memAb trastuzumab to the tumor cells mixed with Jurkat-NFAT-Luc, 'meditope CAR' produced the largest signal. The other two samples were pre-incubated, washed then added to the third component. In one case, memAB trastuzumab was added to the tumor cells, washed, then exposed to the Jurkat-NFAT-Luc, 'meditope CAR'. In the other case, memAB trastuzumab was added to the to the Jurkat-NFAT-Luc, 'meditope CAR', washed, then added to tumor cells. For cells with high antigen expression, pretreatment of the tumor cells led to higher activation. For cells with low antigen expression (MCF7 and OVCAR3), preincubation of the Jurkat-NFAT-Luc, 'meditope CAR' cells led to a higher level of activation. It is important to note that concentration of memAb after 'washing' cells is not known, but certainly less than 4 nM. This different treatment likely accounts for the higher signal in the 4 nM treatment.

FIG. 39. Herceptin blocked activation of FabRack Jurkat cells co-incubated with cancer cells and 4 nM memAb trastuzumab. Herceptin and memAb trastuzumab were continuously present in whole duration of treatment. Method: Cancer cells (2.5×10⁴/100 ul) were seeded in 96-well white-wall plate. After cell attachment for overnight, media in the plate was removed and Jukat-NFAT-Luc me-CAR cells (1×105/60 ul) were added to each well. Bars in the graph represent, from left to right: memAb trastuzumab (4 nM) continuously present, memAb trastuzumab (4 nM) and Herceptin (40 nM) continuously present, and memAb trastuzumab (4 nM) and Herceptin (400 nM) continuously present. Cells were incubated at 37° C. for 6 hr followed by addition of 50 ul luciferase substrate (Invivogen #rep-qlc2) to each well. The luminescence was immediately read by Biotek's Synergy 4 multi-detection microplate reader. Result: In the continuous presence of 4 nM memAb trastuzumab, Jurkat-NFAT-Luc medi-CAR cells were activated due to binding to cancer cells by memAb trastuzumab. Continuous presence of Herceptin during incubation can block Jurkat cell activation, because Herceptin has the same epitope as our memAb trastuzumab and can compete the same binding site on HER2. Herceptin (400 nM) with 100 fold concentration of memAb trastuzumab (4 nM) almost completely block Jurkat cell activation, which demonstrated that Jurkat cell activation was caused by memAb trastuzumab binding to the same HER2 epitope recognized by Herceptin. The activation of the fabrack T cells require the meditope interaction, providing further evidence of the proposed mechanism of action.

Figures 40, 41:
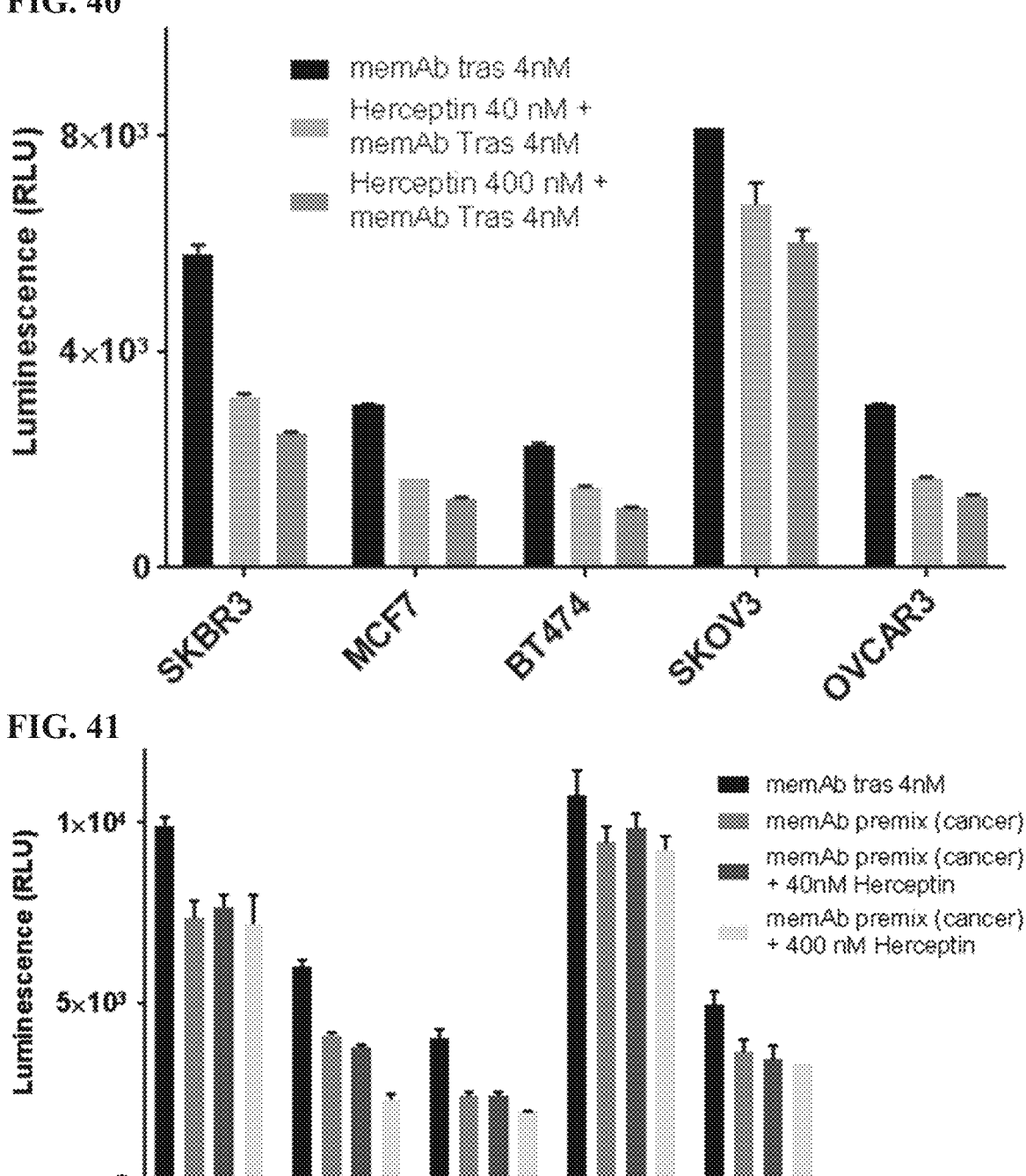

FIG. 40. Herceptin pre-binding to cancer cells blocked activation of FabRack Jurkat cells co-incubated with cancer cells and 4 nM memAb trastuzumab. Cancer cells with 40 nM or 400 nM herceptin pre-binding were followed by a washout. The only difference between Herceptin and memAb trastuzumab is the later has been meditope enabled. By pre-treating the cells with herceptin, access to the antigen is blocked. Washing the Herceptin treated cells before the memAb trastuzumab/Fabrack Jurkat treatment removes the unbound Herceptin. However, bound Herceptin will dissociate from the cells over time. Thus, the reduction in activation is not as dramatic in this experiment (compared to FIG. 41).

FIG. 41. Herceptin marginally blocks activation of FabRack Jurkat cells in coculture with cancer cells with memAb pre-binding. Cancer cells with 100 nM memAb trastuzumab pre-binding were followed by a washout. Cancer cells with memAb trastuzumab pre-binding followed by a wash did not dramatically decreased luminescence activity. Continuous presence of Herceptin during incubation had minor blocking effect on Jurkat cell activation. This data demonstrated that once memAb treastuzumab bound to HER2 on cancer cells, the binding was marginally blocked by clinical trastuzumab. Method: Cancer cells (2.5×10⁴/100 ul) were seeded in 11
12

96-well white-wall plate. After cell attachment for overnight, media in the plate was removed and Jukat-NFAT-Luc me-CAR cells ($1 \times 10^5$) were added to each well. memAb Trastuzumab was continuously present or pre-bound to cancer cells with wash. (Bars in the graph represent, from left to right: memAb trastuzumab (4 nM) continuously present; cancer cells with memAb trastuzumab (100 nM) pre-bound followed by a wash; cancer cells with memAb trastuzumab (100 nM) pre-bound followed by a wash+ Herceptin (40 nM) continuously present; cancer cells with memAb trastuzumab (100 nM) pre-bound followed by a wash+Herceptin (400 nM) continuously present.) Cells were incubated at 37° C. for 6 hr followed by addition of 50 ul luciferase substrate (Invivogen #rep-qlc2) to each well. The luminescence was immediately measured using Biotek's Synergy 4 multi-detection microplate reader. Once the memAb Trastuzumab is bound to the cells, it blocks Herceptin from binding cell derived antigen.

Figure 42:
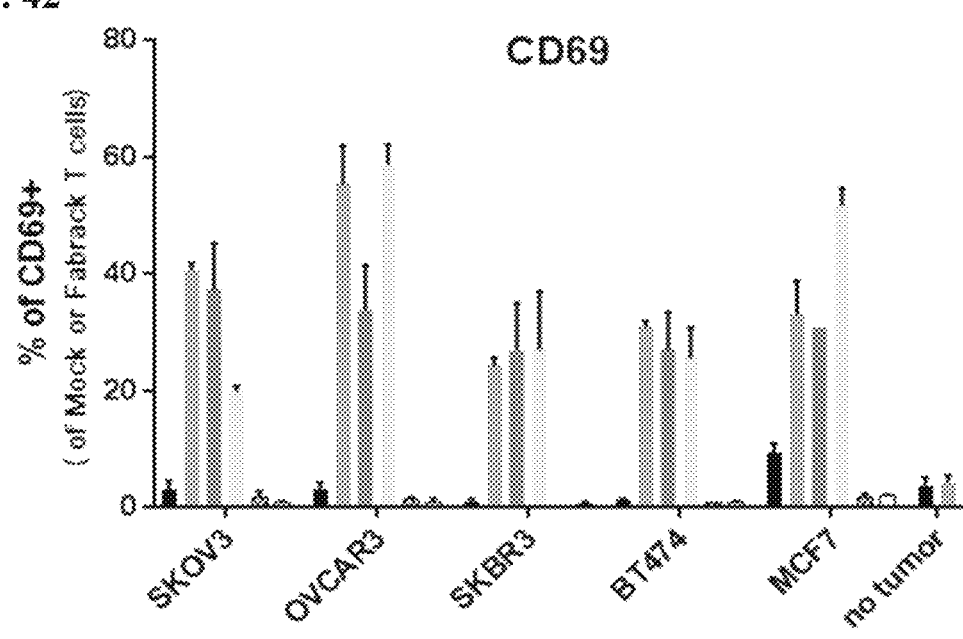
Figure 42:
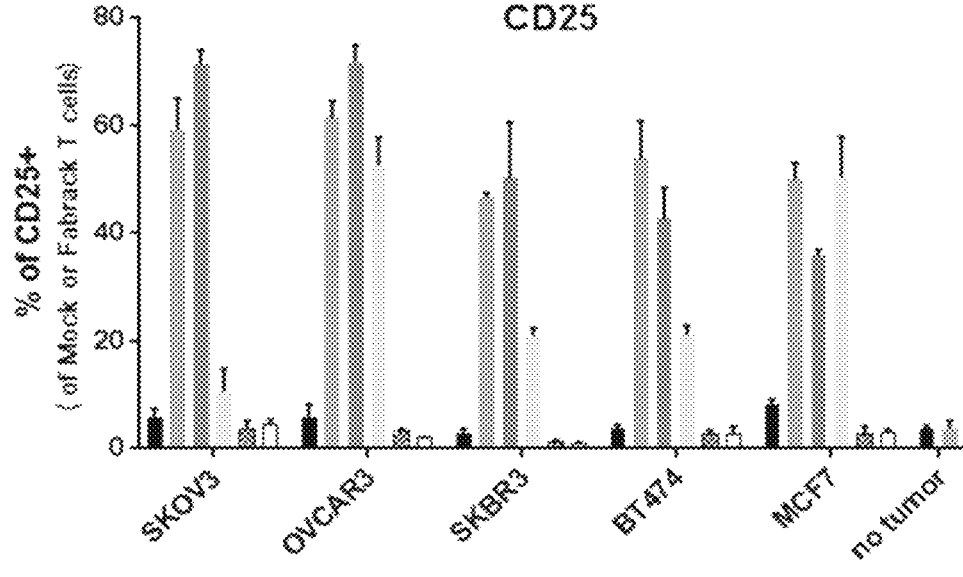

FIG. 42. Expression of activation markers and cytokines of FabRack T cells. FabRack T cells were co-cultured with ovarian cancer cells, SKOV3 and OVCAR3, or breast cancer cells, SKBR3, BT474 and MCF7, in the presence of 0.5 nM memAb trastuzumab for 5 hr. The ratio of effector to target cells is 1:1. HER2 scFv and Fab CAR were used as positive controls. After 5 h incubation, activation markers were analyzed by flow cytometry. Numerous controls were used in these experiments. The CDR loops of the scFv CAR and Fab CAR used here are the same as memAb used for the Fabrack. Mock are non-transformed T cells. Cytometry was used to measure the levels of CD69 and CD25 are markers for T cell activation. No activation of any variant was observed in the absence of tumor cells. Also, little to no activation is observe for Fabrack T cells (no memAb), mock or mock and I83E memAb trastuzumab in the presence of antigen bearing, tumor cells. Finally, a significant increase in T cell activation was observed for the Fabrack Tcells+I83E memAb trastuzumab and the scFV CAR T cells. The Fab-CAR T cells were also activated but demonstrated more variability.

Figure 43:
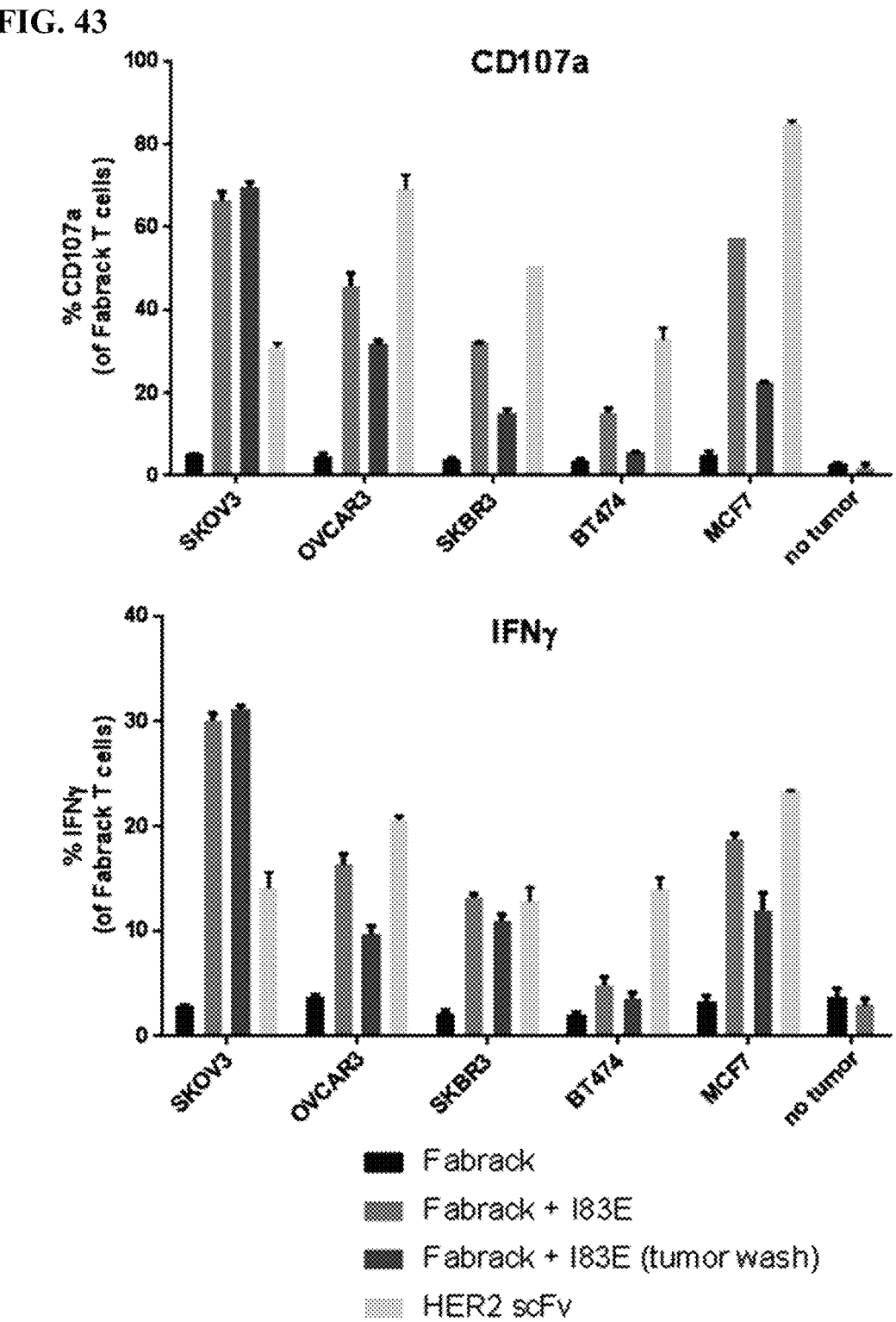

FIG. 43. FabRack T cells were co-cultured with ovarian cancer cells, SKOV3 and OVCAR3, or breast cancer cells, SKBR3, BT474 and MCF7, in the presence of 0.5 nM memAb trastuzumab for 5 hr. The ratio of effector to target cells is 1:1. HER2 scFv CAR was used as positive control. After 5 h incubation, degranulation marker CD107a and IFNγ were analyzed by flow cytometry. Fab T cells behave in a similar manner as the traditional CAR T cells.

Figure 44:
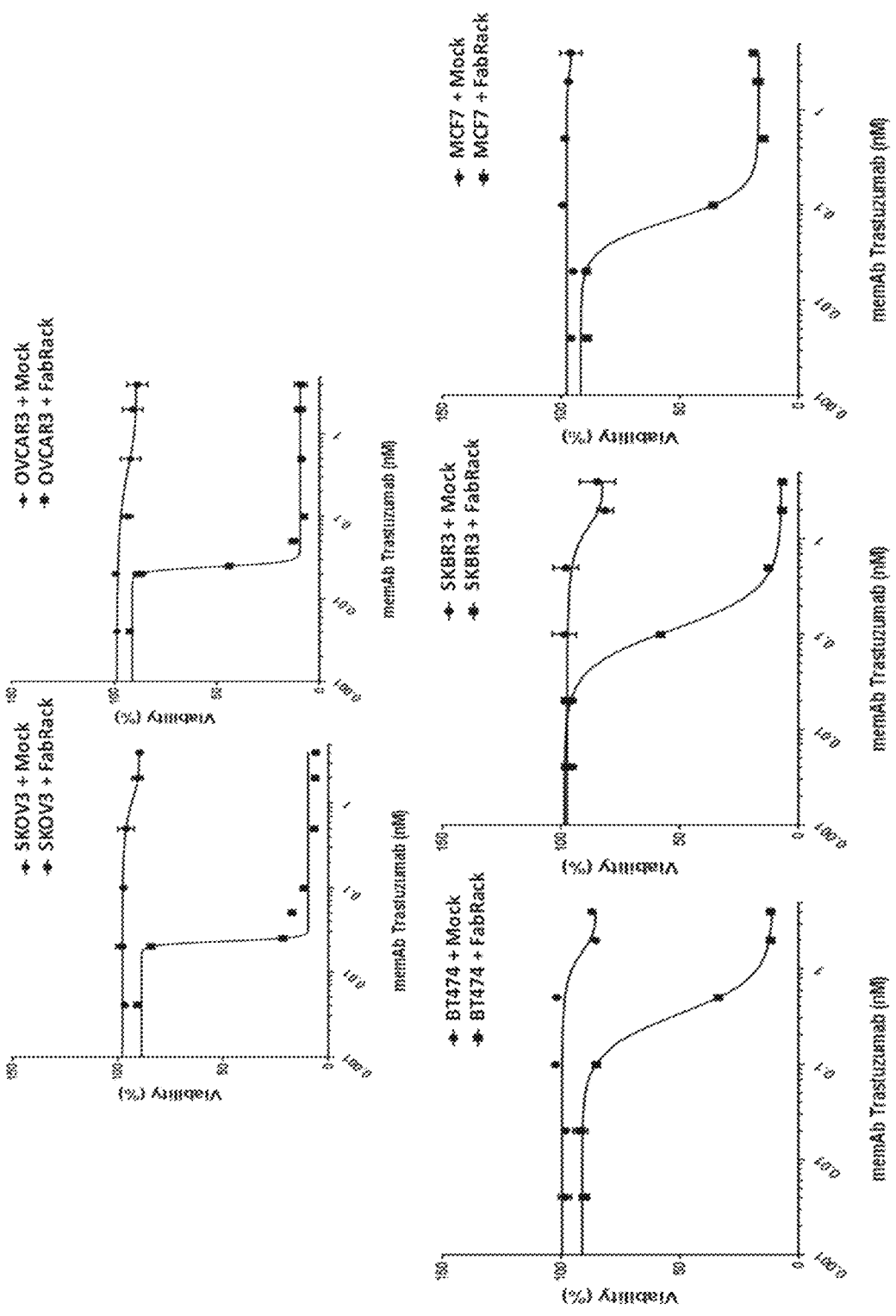

FIG. 44. Cancer cells were incubated with mock T cells or FabRack T cells in the presence of various doses of memAb trastuzumab for 3 day. The ratio of effector to target cells is 1:4. At the end of incubation, cell viability was measured based on instruction of Promega CellTiter kit. Result: Cancer cells were incubated with mock T cells or FabRack T cells in the presence of memAb trastuzumab for 3 days. This data shows that FabRack T cells killed HER2 positive cancer cells effectively since they bind cancer cells through memAb trastuzumab. IC50 of cancer cells co-incubated with memAb trastuzumab and FabRack T cells are 0.33 nM (BT474), 0.11 nM (SKBR3), 0.069 nM (MCF7), 0.046 nM (SKOV3) and 0.027 nM (OVCAR3). The killing effect was not associated with HER2 expression level on cancer cells. Method: For tumor killing assay, cancer cells ($2.5 \times 10^4$/100 ul) and human T cells (6,250/100 ul) were seeded in 96-well round-bottom plate in the presence or absence of antibody. After 72 h incubation, cells were centrifuged at 250×g for 5 min and 100 ul of media in each well was removed. To test cell viability, 100 ul of reagent from Promega CellTiter kit was added in each well. After two-minute incubation, 100 ul of mixture was moved to a white-wall 96-well plate and measured using Biotek's Synergy 4 multi-detection microplate reader.

Figure 45:
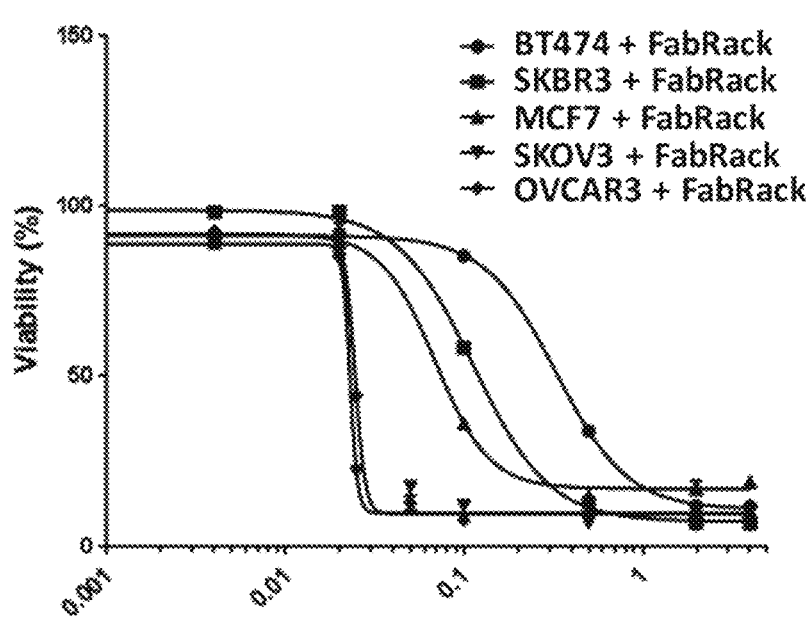

FIG. 45. IC50 of cancer cells co-incubated with memAb trastuzumab and FabRack T cells are 0.33 nM (BT474), 0.11 nM (SKBR3), 0.069 nM (MCF7), 0.046 nM (SKOV3) and 0.027 nM (OVCAR3).

Figure 46:
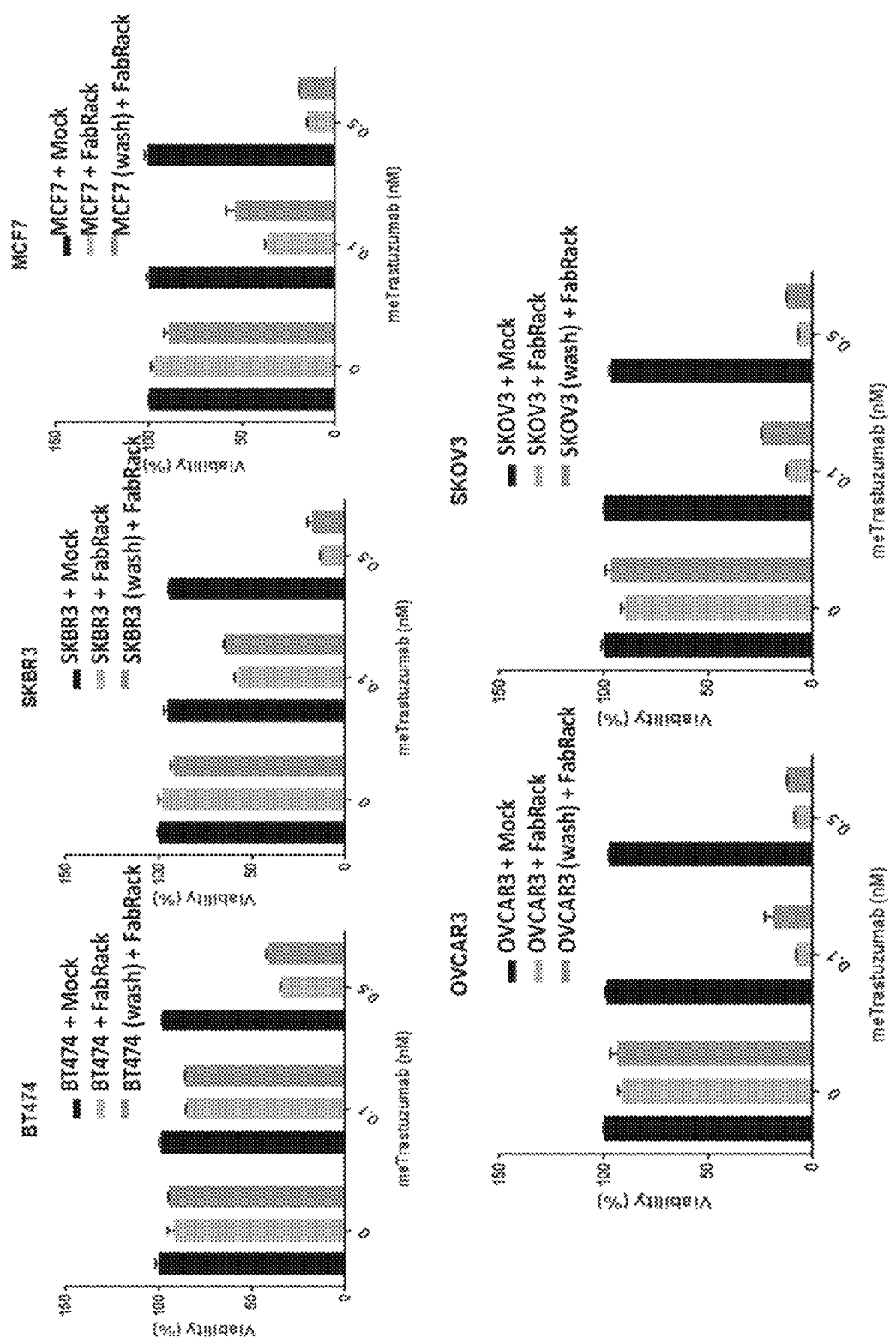

FIG. 46. Result: In the continuous presence of 0.1 nM or 0.5 nM memAb antibody, the viability of cancer cell with FabRack T cell co-incubation (center bar) decreased compared to that with mock T cell co-incubation (left bar). Cell viability decreased dose-dependently at 0.1 and 0.5 nM in breast cancer cell, while ovarian cancer cells show similar viability at these two concentrations. Cancer cells with antibody pre-binding and washout (right bar) can still be killed by human FabRack T cells in spite of reversal of viability by 5-18% compared with cancer cells with continuous antibody treatment. Method: For tumor killing assay, cancer cells ($2.5 \times 10^4$/100 ul) and human T cells (6,250/100 ul) were seeded in 96-well round-bottom plate in the presence or absence of memAb antibody. After 72 h incubation, cells were centrifuged at 250×g for 5 min and 100 ul of media in each well was removed. To test cell viability, 100 ul of reagent from Promega CellTiter kit was added in each well. After two-minute incubation, 100 ul of mixture was moved to a white-wall 96-well plate and measured using Biotek's Synergy 4 multi-detection microplate reader.

Figure 47:
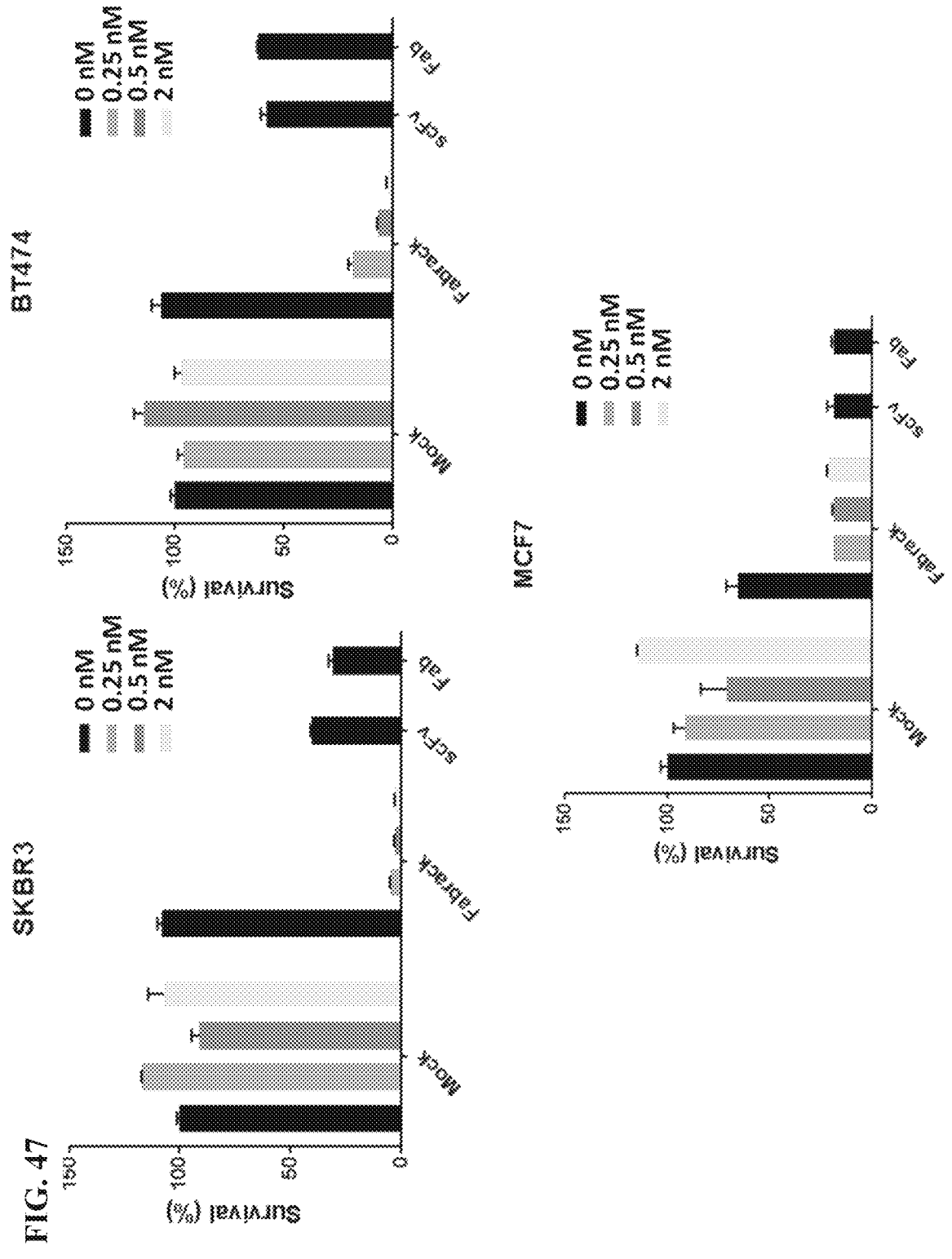

FIG. 47. Flow cytometry was used to analyzed the survival of cancer cells after DAPI staining. HER2 scFv CAR and HER2 Fab CAR were used as positive controls. Result: Flow cytometry were used to analyze how many cancer cells were still live after they were co-incubated with FabRack T cells and memAb trastuzumab compared with cancer cells incubated with HER2 scFv CAR or HER2 Fab CAR T cells as positive control. After incubation for 3 days, the viable cancer cells dramatically decreased when co-incubated with FabRack T cells and memAb trastuzumab. The killing effect of FabRack T cells was similar or even better than HER2 scFv CAR or HER2 Fab CAR T cells. Using an alternative method to read out cell viability produces similar results.

Figure 48:
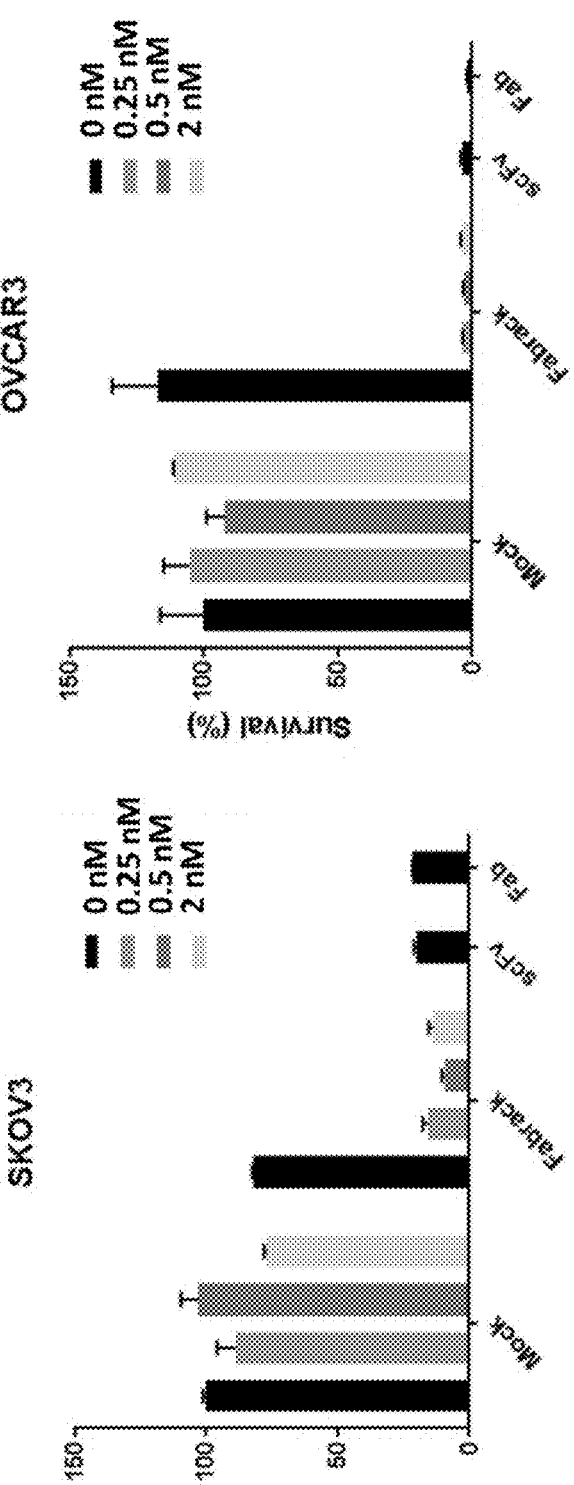

FIG. 48. Flow cytometry was used to analyzed the survival of cancer cells after DAPI staining. HER2 scFv CAR and HER2 Fab CAR were used as positive controls. Result: Flow cytometry were used to analyze how many cancer cells were still live after they were co-incubated with FabRack T cells and memAb trastuzumab compared with cancer cells incubated with HER2 scFv CAR or HER2 Fab CAR T cells as positive control. After incubation for 3 days, the viable cancer cells dramatically decreased when co-incubated with FabRack T cells and memAb trastuzumab. The killing effect of FabRack T cells was similar or even better than HER2 scFv CAR or HER2 Fab CAR T cells.

Figure 49:
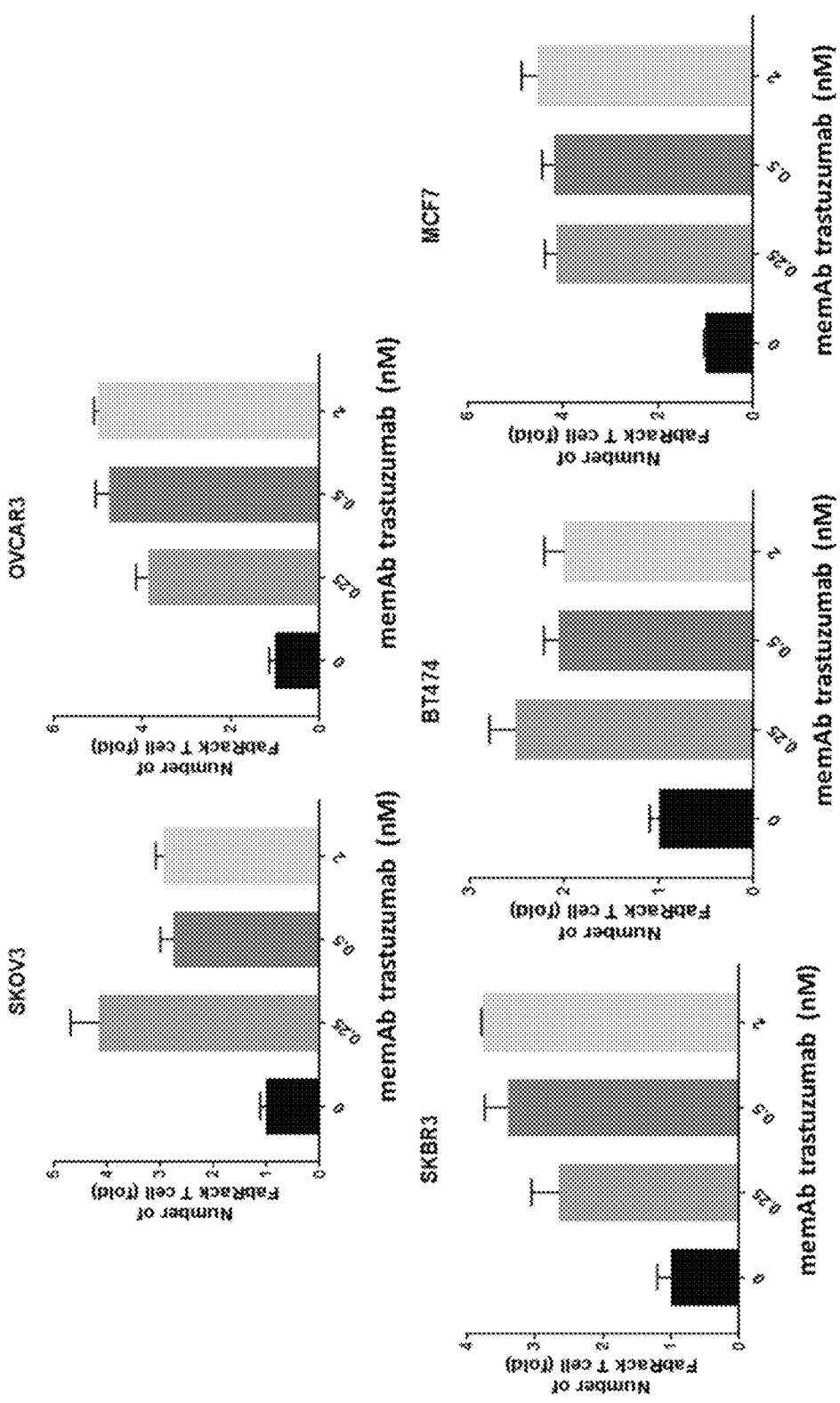

FIG. 49. Fold change of T cell number in co-culture with target cells and different concentrations of memAb trastuzumab. The ratio of effector to target cells is 1:4 during incubation. These experiments indicate activation of T cells, leading to cell proliferation dependent on the presence of the memAb.

Figure 50:
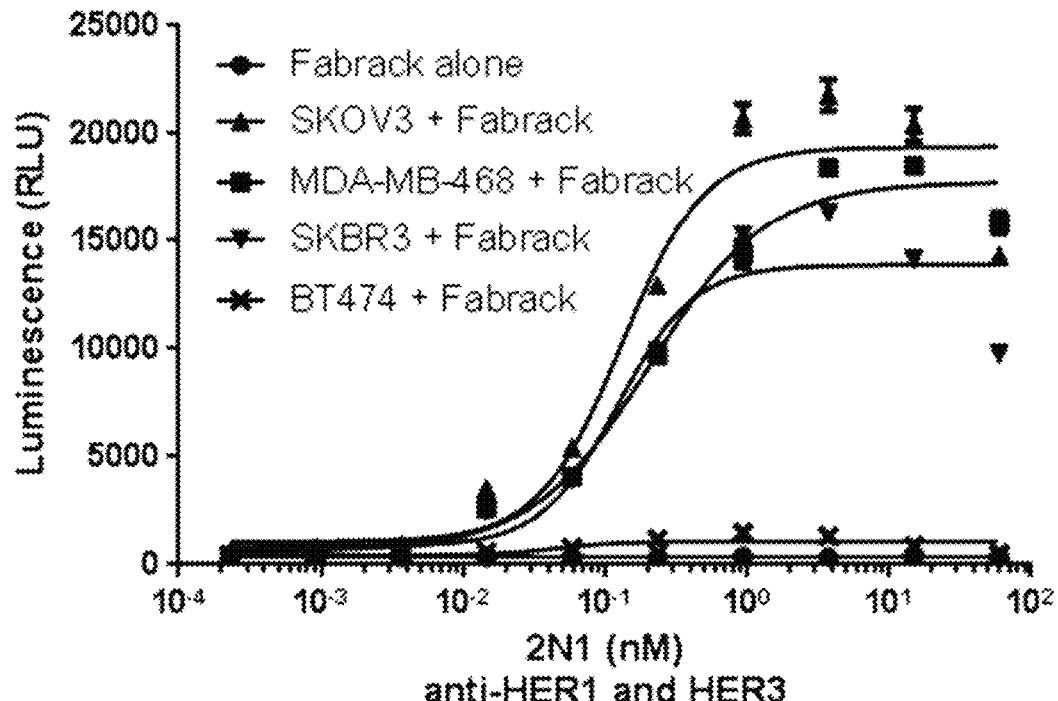

FIG. 50. Breast cancer cells ($2.5 \times 10^4$) were seeded in 96-well white-wall plate. After cell attachment for overnight, media in the plate was removed and Jukat-NFAT-Luc Fabrack cells (41BB version, $1 \times 10^5$) with various doses of 2N1 memAb were added to each well. Cells were incubated at 37° C. for 6 hr followed by addition of luciferase substrate to each well. The luminescence was immediately read by Biotek's Synergy 4 multi-detection microplate reader.

DETAILED DESCRIPTION OF THE INVENTION

Definitions

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable non-cyclic straight or branched chain, or combinations thereof, including at least one carbon atom and at least one heteroatom (e.g. O, N, P, Si or S) and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CHO—CH$_3$, —Si(CH$_3$)$_3$, —CH$_2$—CH=N—OCH$_3$, —C—H=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C1-C4) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S(O$_2$)—R', where R' is a substituted or unsubstituted alkyl group as defined above. R' may have a specified number of carbons (e.g., "C$_1$-C$_4$ alkylsulfonyl").

Each of the above terms (e.g., "alkyl," "heteroalkyl," "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R")=NR''', —S(O)R', —S(O)$_2$R', —S(O)$_2$N(R)('R"—NRSO$_2$R'), —CN, and —NO$_2$ in a number ranging from zero to (2m'+ 1), where m' is the total number of carbon atoms in such radical. R', R", R''', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R'', R''', and R'''' group when more than one of these groups is present. When R' and R'' are attached to the same nitrogen atom, they can be combined with the nitrogen atom to form a 4-, 5-, 6-, or 7-membered ring. For example, —NR'R'' includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R'', —SR', -halogen, —SiR'R''R''', —OC(O)R', —C(O)R', —CO$_2$R', —CONR'R'', —OC(O)NR'R'', —NR''C(O)R', —NR'—C (O)NR''R''', NR''C(O)$_2$R', NRC(NR'R'')=NR''', S(O)R', —S(O)$_2$R', —S(O)$_2$N(R')(R'', —NRSO$_2$R'), —CN, —NO$_2$, —R', —N$_3$, —CH(Ph)$_2$, fluoro(C$_1$-C$_4$)alkoxy, and fluoro (C$_1$-C$_4$)alkyl, in a number ranging from zero to the total number of open valences on the aromatic ring system; and where R', R'', R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R'', R''', and R'''' groups when more than one of these groups is present.

Where a moiety is substituted with an R substituent, the group may be referred to as "R-substituted." Where a moiety is R-substituted, the moiety is substituted with at least one R substituent and each R substituent is optionally different. For example, where a moiety herein is R$^{1A}$-substituted or unsubstituted alkyl, a plurality of R$^{1A}$ substituents may be attached to the alkyl moiety wherein each R$^{1A}$ substituent is optionally different. Where an R-substituted moiety is substituted with a plurality R substituents, each of the R-substituents may be differentiated herein using a prime symbol (') such as R', R'', etc. For example, where a moiety is R$^{3A}$-substituted or unsubstituted alkyl, and the moiety is substituted with a plurality of R$^{3A}$ substituents, the plurality of R$^{3A}$ substituents may be differentiated as R$^{3A'}$, R$^{3A''}$, R$^{3A'''}$, etc. In some embodiments, the plurality of R substituents is 3. In some embodiments, the plurality of R substituents is 2.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C''R'R''')$_d$—, where variables s and d are independently integers of from 0 to 3, and X' is —O—, —NR'—, —S—, —S(O)—, —S(O)$_2$—, or —S(O)$_2$NR'—. The substituents R, R', R'', and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)— OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)— OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo,
halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

As used herein, the term "conjugate" refers to the association between atoms or molecules. The association can be direct or indirect. For example, a conjugate between a nucleic acid and a protein can be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the microparticle is non-covalently attached to solid support through a non-covalent chemical reaction between a component of the microparticle and a component of solid support. In other embodiments, the microparticle includes one or more reactive moieties, e.g., a covalent reactive moiety, as described herein (e.g., an amine reactive moiety). In other embodiments, the microparticle includes a linker with one or more reactive moieties, e.g., a covalent reactive moiety, as described herein (e.g., an amine reactive moiety).

Useful reactive moieties or functional groups used for conjugate chemistries (including "click chemistries" as known in the art) herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold;

(h) amine or sulfhydryl groups, which can be, for example, acylated, alkylated or oxidized;

(i) alkenes, which can undergo, for example, cycloadditions, acylation, Michael addition, etc.;

(j) epoxides, which can react with, for example, amines and hydroxyl compounds;

(k) phosphoramidites and other standard functional groups useful in nucleic acid synthesis;

(l) metal silicon oxide bonding;

(m) metal bonding to reactive phosphorus groups (e.g. phosphines) to form, for example, phosphate diester bonds; and (n) sulfones, for example, vinyl sulfone.

Chemical synthesis of compositions by joining small modular units using conjugate ("click") chemistry is well known in the art and described, for example, in H. C. Kolb, M. G. Finn and K. B. Sharpless ((2001). "Click Chemistry: Diverse Chemical Function from a Few Good Reactions". Angewandte Chemie International Edition 40 (11): 2004-2021); R. A. Evans ((2007). "The Rise of Azide-Alkyne 1,3-Dipolar 'Click' Cycloaddition and its Application to Polymer Science and Surface Modification". Australian Journal of Chemistry 60 (6): 384-395; W. C. Guida et al. Med. Res. Rev. p 3 1996; Spiteri, Christian and Moses, John E. ((2010). "Copper-Catalyzed Azide-Alkyne Cycloaddition: Regioselective Synthesis of 1,4,5-Trisubstituted 1,2,3-Triazoles". Angewandte Chemie International Edition 49 (1): 31-33); Hoyle, Charles E. and Bowman, Christopher N. ((2010). "Thiol-Ene Click Chemistry". Angewandte Chemie International Edition 49 (9): 1540-1573); Blackman, Melissa L. and Royzen, Maksim and Fox, Joseph M. ((2008). "Tetrazine Ligation: Fast Bioconjugation Based on Inverse-Electron-Demand Diels-Alder Reactivity". Journal of the American Chemical Society 130 (41): 13518-13519); Devaraj, Neal K. and Weissleder, Ralph and Hilderbrand, Scott A. ((2008). "Tetrazine Based Cycloadditions: Application to Pretargeted Live Cell Labeling". Bioconjugate Chemistry 19 (12): 2297-2299); Stöckmann, Henning;

Neves, Andre; Stairs, Shaun; Brindle, Kevin; Leeper, Finian ((2011). "Exploring isonitrile-based click chemistry for ligation with biomolecules". Organic & Biomolecular Chemistry), all of which are hereby incorporated by reference in their entirety and for all purposes.

The reactive functional groups can be chosen such that they do not participate in, or interfere with, the chemical stability of the proteins or nucleic acids described herein. By way of example, the nucleic acids can include a vinyl sulfone or other reactive moiety (e.g., maleimide). Optionally, the nucleic acids can include a reactive moiety having the formula —S—S—R. R can be, for example, a protecting group. Optionally, R is hexanol. As used herein, the term hexanol includes compounds with the formula $C_6H_{13}OH$ and includes, 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 2,2-dimethyl-1-butanol, 2,3-dimethyl-1-butanol, 3,3-dimethyl-1-butanol, 2,3-dimethyl-2-butanol, 3,3-dimethyl-2-butanol, and 2-ethyl-1-butanol. Optionally, R is 1-hexanol.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this invention. The following definitions are provided to facilitate understanding of certain terms used frequently herein and are not meant to limit the scope of the present disclosure.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "cell" as used herein, refers to a cell carrying out metabolic or other functions sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

The terms "peptidyl" and "peptidyl moiety" refer to a peptide attached to the remainder of the molecule (e.g., the recombinant protein provided herein or the peptide domain forming part of the recombinant protein provided herein). A peptidyl moiety may be substituted with a chemical linker that serves to attach the peptidyl moiety to the remainder of the recombinant protein (e.g., the transmembrane domain, the spacer region or the peptidyl linker). The peptidyl moiety may also be substituted with additional chemical moieties (e.g., additional R substituents). In embodiments, the non-CDR Fab binding peptide domain includes a peptidyl moiety. In embodiments, the non-CDR Fab binding peptide domain is a peptidyl moiety. The term "meditope" as used herein refers to a peptidyl moiety included in the peptide domain as described herein. Thus, in embodiments, the non-CDR Fab binding peptide domain is a meditope. In embodiments, the non-CDR Fab binding peptide domain includes a meditope.

The peptidyl moiety (e.g., meditope) may be a linear or a cyclic peptide moiety. Various methods for cyclization of a peptide moiety may be used, e.g., to address in vivo stability and to enable chemoselective control for subsequent conjugation chemistry. In some embodiments, the cyclization strategy is a lactam cyclization strategy, including head-to-tail (head-tail) lactam cyclization (between the terminal residues of the acyclic peptide) and/or lactam linkage between other residues. Lactam formation may also be affected by incorporating residues such as glycine, (3-Ala and/or 7-aminoheptanoic acid, and the like, into the acyclic peptide cyclization precursors to produce different lactam ring sizes and modes of connectivity. Additional cyclization strategies such as "click" chemistry and olefin metathesis also can be used. Such methods of peptide and peptidomimetic cyclization are well known in the art. In embodiments, the peptidyl moiety (e.g., meditope) is a linear peptidyl moiety (e.g., linear meditope). In embodiments, the peptidyl moiety (e.g., meditope) is a cyclic peptidyl moiety (e.g., cyclic meditope).

A "label", "detectable domain" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

A "labeled protein or polypeptide" is one that is bound, either covalently, through a linker or a chemical bond, or noncovalently, through ionic, van der Waals, electrostatic, or hydrogen bonds to a label such that the presence of the labeled protein or polypeptide may be detected by detecting the presence of the label bound to the labeled protein or polypeptide. Alternatively, methods using high affinity interactions may achieve the same results where one of a pair of binding partners binds to the other, e.g., biotin, streptavidin.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that may be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence. An amino acid residue in a protein "corresponds" to a given residue when it occupies the same essential structural position within the protein as the given residue. For example, a selected residue in a selected antibody (or Fab domain) corresponds to light chain threonine at Kabat position 40, when the selected residue occupies the same essential spatial or other structural relationship as a light chain threonine at Kabat position 40. In some embodiments, where a selected protein is aligned for maximum homology with the light chain of an antibody (or Fab domain), the position in the aligned selected protein aligning with threonine 40 is said to correspond to threonine 40. Instead of a primary sequence alignment, a three dimensional structural alignment can also be used, e.g., where the structure of the selected protein is aligned for maximum correspondence with the light chain threonine at Kabat position 40, and the overall structures compared. In this case, an amino acid that occupies the same essential position as threonine 40 in the structural model is said to correspond to the threonine 40 residue.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids sequences encode any given amino acid residue. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers to nucleic acids that have the same basic chemical structure as a naturally occurring nucleic acid. Such analogues have modified sugars and/or modified ring substituents, but retain the same basic chemical structure as the naturally occurring nucleic acid. A nucleic acid mimetic refers to chemical compounds that have a structure that is different the general chemical structure of a nucleic acid, but that functions in a manner similar to a naturally occurring nucleic acid. Examples of such analogues include, without limitation, phosphorothiolates, phosphoramidates, methyl phosphonates, chiral-methyl phosphonates, 2-O-methyl ribonucleotides, and peptide-nucleic acids (PNAs).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length. The present invention includes polypeptides that are substantially identical to any of SEQ ID NOs:1-35.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross-reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 *Molecular Cloning: A Laboratory Manual,* 18.1-18.88.

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell. Expression of a transfected gene can further be accomplished by transposon-mediated insertion into to the host genome. During transposon-mediated insertion, the gene is positioned in a predictable manner between two transposon linker sequences that allow insertion into the host genome as well as subsequent excision. Stable expression of a transfected gene can further be accomplished by infecting a cell with a lentiviral vector, which after infection forms part of (integrates into) the cellular genome thereby resulting in stable expression of the gene.

The terms "plasmid", "vector" or "expression vector" refer to a nucleic acid molecule that encodes for genes and/or regulatory elements necessary for the expression of genes. Expression of a gene from a plasmid can occur in cis or in trans. If a gene is expressed in cis, the gene and the regulatory elements are encoded by the same plasmid. Expression in trans refers to the instance where the gene and the regulatory elements are encoded by separate plasmids.

The terms "transfection", "transduction", "transfecting" or "transducing" can be used interchangeably and are defined as a process of introducing a nucleic acid molecule or a protein to a cell. Nucleic acids are introduced to a cell using non-viral or viral-based methods. The nucleic acid molecules may be gene sequences encoding complete proteins or functional portions thereof. Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetofection and electroporation. In some embodiments, the nucleic acid molecules are introduced into a cell using electroporation following standard procedures well known in the art. For viral-based methods of transfection any useful viral vector may be used in the methods described herein. Examples for viral vectors include, but are not limited to retroviral, adenoviral, lentiviral and adeno-associated viral vectors. In some embodiments, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) *Gene Therapy* 8:1-4 and Prochiantz (2007) *Nat. Methods* 4:119-20.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody plays a significant role in determining the specificity and affinity of binding. In some embodiments, antibodies or fragments of antibodies may be derived from different organisms, including humans, mice, rats, hamsters, camels, etc. Antibodies of the invention may include antibodies that have been modified or mutated at one or more amino acid positions to improve or modulate a desired function of the antibody (e.g. glycosylation, expression, antigen recognition, effector functions, antigen-binding, specificity, etc.).

Antibodies are large, complex molecules (molecular weight of ~150,000 Da or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site (paratope), which docks onto the target antigen (epitope). The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

An "antibody variant" as provided herein refers to a polypeptide capable of binding to an antigen and including one or more structural domains (e.g., light chain variable domain, heavy chain variable domain) of an antibody or fragment thereof. Non-limiting examples of antibody variants include single-domain antibodies or nanobodies, mono-specific Fab$_2$, bispecific Fab$_2$, trispecific Fab$_3$, monovalent IgGs, scFv, bispecific diabodies, trispecific triabodies, scFv-Fc, minibodies, IgNAR, V-NAR, hcIgG, VhH, or peptibodies. A "peptibody" as provided herein refers to a peptide moiety attached (through a covalent or non-covalent linker) to the Fc domain of an antibody. Further non-limiting examples of antibody variants known in the art include antibodies produced by cartilaginous fish or camelids. A general description of antibodies from camelids and the variable regions thereof and methods for their production, isolation, and use may be found in references WO97/49805 and WO 97/49805 which are incorporated by reference herein in their entirety and for all purposes. Likewise, antibodies from cartilaginous fish and the variable regions thereof and methods for their production, isolation, and use may be found in WO2005/118629, which is incorporated by reference herein in its entirety and for all purposes.

The terms "CDR L1," "CDR L2" and "CDR L3" as provided herein refer to the complementarity determining regions (CDR) 1, 2, and 3 of the variable light (L) chain of an antibody. In embodiments, the variable light chain provided herein includes in N-terminal to C-terminal direction a CDR L1, a CDR L2 and a CDR L3. Likewise, the terms "CDR H1," "CDR H2" and "CDR H3" as provided herein refer to the complementarity determining regions (CDR) 1, 2, and 3 of the variable heavy (H) chain of an antibody. In embodiments, the variable heavy chain provided herein includes in N-terminal to C-terminal direction a CDR H1, a CDR H2 and a CDR H3.

The terms "FR L1," "FR L2," "FR L3" and "FR L4" as provided herein are used according to their common meaning in the art and refer to the framework regions (FR) 1, 2, 3 and 4 of the variable light (L) chain of an antibody. In embodiments, the variable light chain provided herein includes in N-terminal to C-terminal direction a FR L1, a FR L2, a FR L3 and a FR L4. Likewise, the terms "FR H1," "FR H2," "FR H3" and "FR H4" as provided herein are used according to their common meaning in the art and refer to the framework regions (FR) 1, 2, 3 and 4 of the variable heavy (H) chain of an antibody. In embodiments, the variable heavy chain provided herein includes in N-terminal to C-terminal direction a FR H1, a FR H2, a FR H3 and a FR H4.

The term "antibody" is used according to its commonly known meaning in the art. Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_{H1}$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially a Fab with part of the hinge region (see Fundamental Immunology (Paul ed., 3rd ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) or light chain variable region and variable heavy chain (VH) or heavy chain variable region refer to these light and heavy chain regions, respectively. The terms variable light chain (VL) and light chain variable region as referred to herein may be used interchangeably. The terms variable heavy chain (VH) and heavy chain variable region as referred to herein may be used interchangeably. The Fc (i.e. fragment crystallizable region) is the "base" or "tail" of an immunoglobulin and is typically composed of two heavy chains that contribute two or three constant domains depending on the class of the antibody. By binding to specific proteins the Fc region ensures that each antibody generates an appropriate immune response for a given antigen. The Fc region also binds to various cell receptors, such as Fc receptors, and other immune molecules, such as complement proteins.

The term "antigen" as provided herein refers to molecules capable of binding to the antibody binding domain provided herein. An "antigen binding domain" as provided herein is a region of an antibody that binds to an antigen (epitope). As described above, the antigen binding domain is generally composed of one constant and one variable domain of each of the heavy and the light chain (CH, CL, VH, and VL, respectively). The paratope or antigen-binding site is formed on the N-terminus of the antigen binding domain. The two variable domains of an antigen binding domain typically bind the epitope on an antigen.

Antibodies exist, for example, as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially the antigen-binding portion with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa.

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633, 425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676, 980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816, 567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen-binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

A "therapeutic antibody" as provided herein refers to any antibody or functional fragment thereof that is used to treat cancer, autoimmune diseases, transplant rejection, cardiovascular disease or other diseases or conditions such as those described herein. Non-limiting examples of therapeutic antibodies include murine antibodies, murinized or humanized chimera antibodies or human antibodies including, but not limited to, Erbitux (cetuximab), ReoPro (abciximab), Simulect (basiliximab), Remicade (infliximab); Orthoclone OKT3 (muromonab-CD3); Rituxan (rituximab), Bexxar (tositumomab), Humira (adalimumab), Campath (alemtuzumab), Simulect (basiliximab), Avastin (bevacizumab), Cimzia (certolizumab pegol), Zenapax (daclizumab), Soliris (eculizumab), Raptiva (efalizumab), Mylotarg (gemtuzumab), Zevalin (ibritumomab tiuxetan), Tysabri (natalizumab), Xolair (omalizumab), Synagis (palivizumab), Vectibix (panitumumab), Lucentis (ranibizumab), and Herceptin (trastuzumab).

Techniques for conjugating therapeutic agents to antibodies are well known (see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)). As used herein, the term "antibody-drug conjugate" or "ADC" refers to a therapeutic agent conjugated or otherwise covalently bound to to an antibody. A "therapeutic agent" as referred to herein, is a composition useful in treating or preventing a disease such as cancer.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions typically requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).
protein).

A "ligand" refers to an agent, e.g., a polypeptide or other molecule, capable of binding to a receptor.

The term "recombinant" when used with reference, for example, to a cell, a nucleic acid, a protein, or a vector, indicates that the cell, nucleic acid, protein or vector has been modified by or is the result of laboratory methods. Thus, for example, recombinant proteins include proteins produced by laboratory methods. Recombinant proteins can include amino acid residues not found within the native (non-recombinant) form of the protein or can be include amino acid residues that have been modified, e.g., labeled.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a recombinant protein as described herein and an antigen-binding domain. In embodiments contacting includes, for example, allowing a recombinant protein described herein to interact with an antigen-binding domain.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Patient" or "subject in need thereof" refers to a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

The terms "disease" or "condition" refer to a state of being or health status of a patient or subject capable of being treated with a compound, pharmaceutical composition, or method provided herein. In embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma).

The terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease. In embodiments, "treating" refers to treatment of cancer.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "therapeutically effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "Her2 protein" or "Her2" as used herein includes any of the recombinant or naturally-occurring forms of Receptor tyrosine-protein kinase erbB-2, also known as CD340 (cluster of differentiation 340), proto-oncogene Neu, Erbb2 (rodent), or ERBB2 (human), or variants or homologs thereof that maintain Her2 activity (e.g. within at least 50%, 80%, 90%, 95%, 96%, 97%, 98%, 99% or 100% activity compared to Her2). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Her2 protein. In embodiments, the Her2 protein is substantially identical to the protein identified by the UniProt reference number P04626 or a variant or homolog having substantial identity thereto.

The term "EGFR protein" or "EGFR" as used herein includes any of the recombinant or naturally-occurring forms of epidermal growth factor receptor (EGFR) also known as ErbB-1 or HER1 in humans, or variants or homologs thereof that maintain EGFR activity (e.g. within at least 50%, 80%, 90%, 95%, 96%, 97%, 98%, 99% or 100% activity compared to EGFR). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring EGFR protein. In embodiments, the EGFR protein is substantially identical to the protein identified by the UniProt reference number P00533 or a variant or homolog having substantial identity thereto.

The term "CD19 protein" or "CD19" as used herein includes any of the recombinant or naturally-occurring forms of B-lymphocyte antigen CD19, also known as CD19 molecule (Cluster of Differentiation 19), B-Lymphocyte Surface Antigen B4, T-Cell Surface Antigen Leu-12 and CVID3, or variants or homologs thereof that maintain CD19 activity (e.g. within at least 50%, 80%, 90%, 95%, 96%, 97%, 98%, 99% or 100% activity compared to CD19). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD19 protein. In embodiments, the CD19 protein is substantially identical to the protein identified by the UniProt reference number P15391 or a variant or homolog having substantial identity thereto.

The term "CD20 protein" or "CD20" as used herein includes any of the recombinant or naturally-occurring forms of B-lymphocyte antigen CD20 or Cluster of Differentiation 20 (CD20), or variants or homologs thereof that maintain CD20 activity (e.g. within at least 50%, 80%, 90%, 95%, 96%, 97%, 98%, 99% or 100% activity compared to CD20). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD20 protein. In embodiments, the CD20 protein is substantially identical to the protein identified by the UniProt reference number P11836 or a variant or homolog having substantial identity thereto.

Recombinant Protein Compositions

Provided herein are, inter alia, recombinant proteins expressed by a T cell, capable of binding to an antigen-binding domain (e.g., an antibody, variant or fragment thereof) and thereby targeting the T cell to a cell (e.g., tumor cell) expressing the antigen bound by the antigen-binding domain. Through binding of the recombinant protein expressed by the T cell to an antigen-binding domain and binding of the antigen-binding domain to an antigen expressed by a target cell, the T cell is activated, becomes cytotoxic and thereby eliminates the target cell (e.g., cancer cell). The recombinant proteins provided herein, inter alia, allow to rapidly add functionality to adoptive immuno-therapy and are useful, inter alia, for a broad variety of therapeutic and diagnostic purposes. For example, the recombinant proteins provided herein including embodiments thereof may be used as means to direct effector T-cells (e.g., autologous T cells) and therapeutic antibodies to their sites of action thereby decreasing off-target effects. The compostions provided herein allow to rapidly and efficiently alter the target specificity without creating and optimizing individual CAR T cells.

The recombinant proteins provided herein are continuous single chain polypeptides, which include for example, a non-CDR Fab binding peptide domain, an intracellular T-cell signaling domain and a transmembrane domain, which connects the non-CDR Fab binding peptide domain to the intracellular T-cell signaling domain. The recombinant proteins provided herein may include further elements, e.g., spacer region, peptide linker, intracellular co-stimulatory signaling domain, all of which form part of said continuous single chain polypeptide. A continuous single chain polypeptide as provided herein refers to a polypeptide chain including elements that are covalently attached to each other thereby forming a continuous polypeptide chain.

Thus, in one aspect, a recombinant protein is provided. The recombinant protein includes: (i) a non-CDR Fab binding peptide domain; (ii) an intracellular T-cell signaling domain; and (iii) a transmembrane domain connecting the non-CDR Fab binding peptide domain to the intracellular T-cell signaling domain. In embodiments, the intracellular T-cell signaling domain is a CD3ζ intracellular T-cell signaling domain.

A "non-CDR Fab binding peptide domain" as provided herein refers to a peptide or a peptide domain including a peptide, which is capable to bind to a non-CDR binding site of an antibody, antibody variant or fragment thereof. In embodiments, the non-CDR Fab binding peptide domain is a peptide. In embodiments, the non-CDR Fab binding peptide domain includes a peptide. In embodiments, the non-CDR Fab binding peptide domain binds the non-CDR binding site. In embodiments, the non-CDR Fab binding peptide domain is a peptidyl moiety. In embodiments, the peptidyl moiety is a moiety as described in published US application US20120301400 A1, which is hereby incorporated by reference in its entirety and for all purposes.

In embodiments, the non-CDR Fab binding peptide domain includes a peptide moiety of formula:

$$X0\text{-}X1\text{-}X2\text{-}X3\text{-}X4\text{-}X5\text{-}X6\text{-}X7\text{-}X8\text{-}X9\text{-}X10\text{-}X11\text{-}X12 \qquad (I).$$

In formula (I), X0 is Ser or null. X1 is Ser, Cys, Gly, β-alanine, diaminopropionic acid, β-azidoalanine, or null. X2 is Gln or null. X3 is Phe, Tyr, β,β'-diphenyl-Ala, His, Asp, 2-bromo-L-phenylalanine, 3-bromo-L-phenylalanine, 4-bromo-L-phenylalanine, Asn, Gln, a modified Phe, a hydratable carbonyl-containing residue, or a boronic acid-containing residue. X4 is Asp or Asn. X5 is Leu, β,β'-diphenyl-Ala, Phe, Trp, Tyr, a non-natural analog of phenylalanine, tryptophan, or tyrosine, a hydratable carbonyl-containing residue, or a boronic acid-containing residue. X6 is Cys or Ser. X7 is Cys, Thr, or Ser. X8 is protected Arg, Arg, or Ala. X9 is Cys, Arg or Ala. X10 is Leu, Gln, Glu, β,β'-diphenyl-Ala, Phe, Trp, Tyr; a non-natural analog of phenylalanine, tryptophan, or tyrosine, a hydratable carbonyl-containing residue, or a boronic acid-containing residue. X11 is Cys, Gln, Lys or Arg. X12 is Ser, Cys, Gly, 7-aminoheptanoic acid, β-alanine, diaminopropionic acid, propargylglycine, isoaspartic acid, or null. X1 and X12 are optionally joined together to form a cyclic peptidyl moiety.

In embodiments, the non-CDR Fab binding peptide domain includes a peptide moiety of formula:

$$X0\text{-}X1\text{-}X2\text{-}X3\text{-}X4\text{-}X5\text{-}X6\text{-}X7\text{-}X8\text{-}X9\text{-}X10\text{-}X11\text{-}X12 \qquad (I).$$

In formula (I), X0 is Ser or null. X1 is Ser, Cys, Gly, β-alanine, or null. X2 is Gln or null. X3 is Phe, Tyr, His, Asp, Asn, or Gln. X4 is Asp or Asn. X5 is Leu, Phe, Trp, Tyr, tryptophan, or tyrosine. X6 is Cys or Ser. X7 is Cys, Thr, or Ser. X8 is Arg, or Ala. X9 is Cys, Arg or Ala. X10 is Leu, Gln, Glu, Phe, Trp, Tyr, tryptophan, or tyrosine. X11 is Cys, Gln, Lys or Arg. X12 is Ser, Cys, Gly, or null. X1 and X12 are optionally joined together to form a cyclic peptidyl moiety.

In embodiments, the non-CDR Fab binding peptide domain includes the sequence of SEQ ID NO:32. In embodiments, the non-CDR Fab binding peptide domain has the sequence of SEQ ID NO:32. In embodiments, the recombinant protein further includes a signaling peptide having the sequence of SEQ ID NO:37. In embodiments, the signaling peptide is bound to the N-terminus of the non-CDR Fab binding peptide domain.

The term "non-CDR binding site" provided herein refers to a binding site of an antigen-binding domain (e.g., Fab domain of an antibody, antibody variant or fragment thereof) that does not include CDR residues of the heavy chains and CDR residues of the light chains of an antibody. The "non-CDR peptide binding site" is a region of an antigen-binding domain, which is capable of non-covalently binding to the non-CDR Fab binding peptide domain of the recombinant protein provided herein. In embodiments, the non-CDR binding site includes framework region amino acid residues. In embodiments, the non-CDR binding site includes FR residues of the heavy chain or the light chain. In embodiments, the non-CDR binding site includes FR residues of the heavy chain and the light chain. In embodiments, the non-CDR binding site includes a residue at a position corresponding to Kabat position 83, a residue at a position corresponding to Kabat position 30 or a residue at a position corresponding to Kabat position 52. In embodiments, the non-CDR binding site includes a residue at a position corresponding to Kabat position 40, a residue at a position corresponding to Kabat position 41, a residue at a position corresponding to Kabat position 30, a residue at a position corresponding to Kabat position 52, a residue at a position corresponding to Kabat position 83, or a residue at a position corresponding to Kabat position 85. In embodiments, the non-CDR binding site includes a residue at a position corresponding to Kabat position 40. In embodiments, the non-CDR binding site includes a residue at a position corresponding to Kabat position 41. In embodiments, the non-CDR binding site includes a residue at a position corresponding to Kabat position 30. In embodiments, the non-CDR binding site includes a residue at a position corresponding to Kabat position 52. In embodiments, the non-CDR binding site includes a residue at a position corresponding to Kabat position 83. In embodiments, the non-CDR binding site includes a residue at a position corresponding to Kabat position 85. In embodiments, the residues forming a non-CDR binding site are residues described in published US application US20120301400 A1, which is hereby incorporate by reference in its entirety and for all purposes.

The non-CDR binding site provided herein may also be referred to as a "meditope binding site." In embodiments, the recombinant protein that binds to the non-CDR binding site through the non-CDR Fab binding peptide domain does not impact (e.g. measurably impact) the binding of the antigen-binding domain to the epitope. In other words, in embodiments, occupancy of the non-CDR binding site does not affect antigen-binding. In embodiments, the non-CDR binding site interacts non-covalently with the non-CDR Fab binding peptide domain (e.g., a meditope) of the recombinant protein provided herein including embodiments thereof. The amino acid residues capable of interacting with the non-CDR Fab binding peptide domain (e.g. a meditope) may form part of an antibody, Fab, antibody variant or any fragment thereof. The non-CDR binding site may be engineered into any appropriate antibody, variant or fragment thereof thereby forming an antigen-binding domain (antigen-binding domain) with the non-CDR binding site. An antigen-binding domain including a non-CDR binding site is also referred to herein as "meditope-enabled antibody", "meditope-enabled domain" or "meditope-enabled antibody region."

An "antigen-binding domain" as provided herein is a region of an antibody, variant or fragment thereof that binds to an antigen (epitope). As described herein, the antigen-binding domain is generally composed of one constant and one variable domain of each of the heavy and the light chain (VL, VH, CL and CH1, respectively). The paratope or antigen-binding site is formed on the N-terminus of the antigen-binding domain. The two variable domains of an antigen-binding domain typically bind the epitope on an antigen. In embodiments, the antigen-binding domain forms part of an antibody. In embodiments, the antigen-binding domain forms part of a therapeutic antibody. In embodiments, the antigen-binding domain forms part of a Fab. In embodiments, the antigen-binding domain is a Fab.

In embodiments, the antigen-binding domain includes a heavy chain constant region (CH) and a light chain constant region (CL). In embodiments, the heavy chain constant region (CH) is the constant region of the heavy chain of an antibody or fragment thereof. In embodiments, the light chain constant region (CL) is the constant region of the light chain of an antibody or fragment thereof. In embodiments, the heavy chain constant region (CH) is the constant region of a Fab. In embodiments, the light chain constant region (CL) is the constant region of the light chain of a Fab. In embodiments, the heavy chain constant region (CH) is the constant region of a F(ab)'2 dimer. In embodiments, the light chain constant region (CL) is the constant region of the light chain of a F(ab)'2 dimer. In embodiments, the antigen-binding domain includes an Fc domain. In embodiments, the antigen-binding domain is a humanized antigen-binding domain. In embodiments, the antigen-binding domain is a humanized mouse antigen-binding domain.

In embodiments, the antigen-binding domain is a trastuzumab meditope-enabled domain, a pertuzumab-meditope enabled domain, a M5A meditope-enabled domain or a rituximab meditope-enabled domain. In embodiments, the antigen-binding domain is a humanized rituximab meditope-enabled domain.

In embodiments, the antigen-binding domain provided herein including embodiments thereof competes for antigen-binding with, specifically binds to the same antigen or epitope as, and/or contains one, more, or all CDRs (or CDRs comprising at least at or about 75, 80, 85, 90, 91, 92, 93, 94, 95, 96, 97, 98, or 99% identity to the CDRs), e.g., including a heavy chain CDR 1, 2, and/or 3 and/or a light chain CDR1, 2, and/or 3, of one or more known antibodies, including any commercially available antibody, such as abagovomab, abciximab, adalimumab, adecatumumab, alemtuzumab, altumomab, altumomab pentetate, anatumomab, anatumomab mafenatox, arcitumomab, atlizumab, basiliximab, bectumomab, ectumomab, belimumab, benralizumab, bevacizumab, brentuximab, canakinumab, capromab, capromab pendetide, catumaxomab, certolizumab, clivatuzumab tetraxetan, daclizumab, denosumab, eculizumab, edrecolomab, efalizumab, etaracizumab, ertumaxomab, fanolesomab, Fbta05, fontolizumab, gemtuzumab, girentuximab, golimumab, ibritumomab, igovomab, infliximab, ipilimumab, labetuzumab, mepolizumab, muromonab, muromonab-CD3, natalizumab, necitumumab, nimotuzumab, ofatumumab, omalizumab, oregovomab, palivizumab, panitumumab, ranibizumab, rituximab, satumomab, sulesomab, ibritumomab, ibritumomab tiuxetan, tocilizumab, tositumomab, trastuzumab, Trbs07, ustekinumab, visilizumab, votumumab, zalutumumab, and/or brodalumab; and/or anrukinzumab, bapineuzumab, dalotuzumab, demcizumab, ganitumab, inotuzumab, mavrilimumab, moxetumomab pasudotox, rilotumumab, sifalimumab, tanezumab, tralokinumab, tremelimumab, urelumab, the antibody produced by the hybridoma 10B5 (see Edelson & Unanue, *Curr Opin*

*Immunol,* 2000 August; 12(4):425-31), B6H12.2 (abeam) or other anti-CD47 antibody (see Chao et al., *Cell,* 142, 699-713, Sep. 3, 2010).

In embodiments, the antigen-binding domain specifically binds to an antigen selected from the group consisting of: CA-125, glycoprotein (GP) IIb/IIIa receptor, TNF-alpha, CD52, TAG-72, Carcinoembryonic antigen (CEA), interleukin-6 receptor (IL-6R), IL-2, interleukin-2 receptor a-chain (CD25), CD22, B-cell activating factor, interleukin-5 receptor (CD125), VEGF, VEGF-A, CD30, IL-1beta, prostate specific membrane antigen (PSMA), CD3, EpCAM, EGF receptor (EGFR), MUC1, human interleukin-2 receptor, Tac, RANK ligand, a complement protein, e.g., C5, EpCAM, CD11a, e.g., human CD11a, an integrin, e.g., alpha-v beta-3 integrin, vitronectin receptor alpha v beta 3 integrin, HER2, neu, CD3, CD15, CD20 (small and/or large loops), Interferon gamma, CD33, CA-IX, TNF alpha, CTLA-4, carcinoembryonic antigen, IL-5, CD3 epsilon, CAM, Alpha-4-integrin, IgE, e.g., IgE Fc region, an RSV antigen, e.g., F protein of respiratory syncytial virus (RSV), TAG-72, NCA-90 (granulocyte cell antigen), IL-6, GD2, GD3, IL-12, IL-23, IL-17, CTAA16.88, IL13, interleukin-1 beta, beta-amyloid, IGF-1 receptor (IGF-1R), delta-like ligand 4 (DLL4), alpha subunit of granulocyte macrophage colony stimulating factor receptor, hepatocyte growth factor, IFN-alpha, nerve growth factor, IL-13, CD326, Programmed cell death 1 ligand 1 (PD-L1, a.k.a. CD274, B7-H1), CD47, and CD137.

In embodiments, the antigen-binding domain is an anti-CD19 protein, anti-CD20 protein, anti-CD22 protein, anti-CD30 protein, anti-CD33 protein, anti-CD44v6/7/8 protein, anti-CD123 protein, anti-CEA protein, anti-EGP-2 protein, anti-EGP-40 protein, anti-erb-B2 protein, anti-erb-B2,3,4 protein, anti-FBP protein, anti-fetal acetylcholine receptor protein, anti-GD2 protein, anti-GD3 protein, anti-Her2/neu protein, anti-IL-13R-a2 protein, anti-KDR protein, anti k-light chain protein, anti-LeY protein, anti-L1 cell adhesion molecule protein, anti-MAGE-A1 protein, anti-mesothelin protein, anti-murine CMV infected cell protein, anti-MUC2 protein, anti-NKGD2 protein, anti, oncofetal antigen protein, anti-PCSA protein, anti-PSMA protein, anti-TAA (targeted by mAb IfE) protein, anti-EGFR protein, anti-TAG-72 protein or anti-VEGF-72 protein. In embodiments, the antigen-binding domain is not cetuximab.

In addition to non-covalently binding to the non-CDR Fab binding peptide domain the antigen-binding domain may be modified (e.g., genetically or chemically) to include a therapeutic moiety or an imaging or detectable moiety. Thus, in embodiments, the antigen-binding domain includes a therapeutic moiety or a detectable moiety.

The term "therapeutic moiety" as provided herein is used in accordance with its plain ordinary meaning and refers to a monovalent compound having a therapeutic benefit (e.g., prevention, eradication, amelioration of the underlying disorder being treated) when given to a subject in need thereof. Therapeutic moieties as provided herein may include, without limitation, peptides, proteins, nucleic acids, nucleic acid analogs, small molecules, antibodies, nanobodies, enzymes, prodrugs, cytotoxic agents (e.g. toxins) including, but not limited to ricin, doxorubicin, daunorubicin, taxol, ethidium bromide, mitomycin, etoposide, tenoposide, vincristine, vinblastine, colchicine, dihydroxy anthracin dione, actinomycin D, diphtheria toxin, *Pseudomonas* exotoxin (PE) A, PE40, abrin, and glucocorticoid. In embodiments, the therapeutic moiety is an anti-cancer agent or chemotherapeutic agent as described herein. In embodiments, the therapeutic moiety is a nucleic acid moiety, a peptide moiety or a small molecule drug moiety. In embodiments, the therapeutic moiety is a nucleic acid moiety. In embodiments, the therapeutic moiety is an antibody moiety. In embodiments, the therapeutic moiety is a peptide moiety. In embodiments, the therapeutic moiety is a small molecule drug moiety. In embodiments, the therapeutic moiety is a nuclease. In embodiments, the therapeutic moiety is an immunostimulator. In embodiments, the therapeutic moiety is a toxin. In embodiments, the therapeutic moiety is a nuclease. In embodiments, the therapeutic moiety is a cytokine (e.g., IL-2). In embodiments, the therapeutic moiety includes a non-natural amino acid. In embodiments, the therapeutic moiety includes a siRNA. In embodiments, the therapeutic moiety is a siRNA. In embodiments, the therapeutic moiety includes an antisense nucleic acid. In embodiments, the therapeutic moiety is an antisense nucleic acid.

An "imaging or detectable moiety" as provided herein is a monovalent compound detectable by spectroscopic, photochemical, biochemical, immunochemical, chemical, or other physical means. In embodiments, the imaging moiety is covalently attached to peptide compound. Exemplary imaging moieties are without limitation $^{32}$P, radionuclides, positron-emitting isotopes, fluorescent dyes, fluorophores, antibodies, bioluminescent molecules, chemiluminescent molecules, photoactive molecules, metals, electron-dense reagents, enzymes (e.g., as commonly used in an ELISA), magnetic contrast agents, quantum dots, nanoparticles, biotin, digoxigenin, haptens and proteins or other entities which can be made detectable, e.g., by incorporating a radiolabel into a peptide or antibody specifically reactive with a target peptide. Any method known in the art for conjugating an antibody to the moiety may be employed, e.g., using methods described in Hermanson, Bioconjugate Techniques 1996, Academic Press, Inc., San Diego. Exemplary fluorophores include fluorescein, rhodamine, GFP, coumarin, FITC, ALEXA fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese. In embodiments, the imaging moiety is a bioluminescent molecule. In embodiments, the imaging moiety is a photoactive molecule. In embodiments, the imaging moiety is a metal. In embodiments, the imaging moiety is a nanoparticle.

The recombinant proteins provided herein includes multiple domains (e.g., intracellular T-cell signaling domain, transmembrane domain, spacer region, intracellular co-stimulatory signaling domain), all of which form part of one continuous single chain polypeptide.

An "intracellular T-cell signaling domain" as provided herein includes amino acid sequences capable of providing primary signaling in response to binding of an antigen to the antibody region provided herein including embodiments thereof. In embodiments, the signaling of the intracellular T-cell signaling domain results in activation of the T cell expressing the same. In embodiments, the signaling of the intracellular T-cell signaling domain results in proliferation (cell division) of the T cell expressing the same. In embodiments, the signaling of the intracellular T-cell signaling domain results in expression by said T cell of proteins known in the art to be characteristic of activated T cells (e.g., CTLA-4, PD-1, CD28, CD69). In embodiments, the intracellular T-cell signaling domain includes the signaling domain of the zeta chain of the human CD3 complex. In embodiments, the intracellular T-cell signaling domain is a CD3 (intracellular T-cell signaling domain.

In embodiments, the intracellular T-cell signaling domain includes the sequence of SEQ ID NO:34. In embodiments, the intracellular T-cell signaling domain is the sequence of SEQ ID NO:34. In embodiments, the intracellular T-cell signaling domain includes the sequence of SEQ ID NO:11. In embodiments, the intracellular T-cell signaling domain is the sequence of SEQ ID NO:11.

For the recombinant proteins provided herein the transmembrane domain connects the non-CDR Fab binding peptide domain to the intracellular T-cell signaling domain. In embodiments, the transmembrane domain is between the non-CDR Fab binding peptide domain and the intracellular T-cell signaling domain. In other words, the transmembrane domain is directly or indirectly (e.g., through a spacer) connected to the C-terminus of the non-CDR Fab binding peptide domain and directly or indirectly (e.g., through a costimulatory signaling domain) connected to the N-terminus of the intracellular T-cell signaling domain.

A "transmembrane domain" as provided herein refers to a polypeptide forming part of a biological membrane. The transmembrane domain provided herein is capable of spanning a biological membrane (e.g., a cellular membrane) from one side of the membrane through to the other side of the membrane. In embodiments, the transmembrane domain spans from the intracellular side to the extracellular side of a cellular membrane. Transmembrane domains may include non-polar, hydrophobic residues, which anchor the proteins provided herein including embodiments thereof in a biological membrane (e.g., cellular membrane of a T cell). Any transmembrane domain capable of anchoring the proteins provided herein including embodiments thereof are contemplated. In embodiments, the transmembrane domain is L-selectin. The term "L-selectin" as provided herein includes any of the recombinant or naturally-occurring forms of the L-selectin protein, also known as CD62L, or variants or homologs thereof that maintain L-selectin activity (e.g. within at least 50%, 80%, 90%, 95%, 96%, 97%, 98%, 99% or 100% activity compared to L-selectin). In embodiments, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring L-selectin polypeptide. In embodiments, L-selectin is the protein as identified by the NCBI sequence reference GI:262206315, homolog or functional fragment thereof. Non-limiting examples of transmembrane domains include, the transmembrane domains of CD8a, CD4 or CD3-zeta. In embodiments, the transmembrane domain is a CD8a transmembrane domain, a CD28 transmembrane domain, a CD4 transmembrane domain or a CD3-zeta transmembrane domain. In embodiments, the transmembrane domain is a CD28 transmembrane domain.

The term "CD28 transmembrane domain" as provided herein includes any of the recombinant or naturally-occurring forms of the transmembrane domain of CD28, or variants or homologs thereof that maintain CD28 transmembrane domain activity (e.g. within at least 50%, 80%, 90%, 95%, 96%, 97%, 98%, 99% or 100% activity compared to the CD28 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD28 transmembrane domain polypeptide. In embodiments, the CD28 transmembrane domain is the protein as identified by SEQ ID NO:18 or SEQ ID NO:2, variant, homolog or functional fragment thereof. In embodiments, CD28 is the protein as identified by the NCBI sequence reference GI:340545506, homolog or functional fragment thereof.

In embodiments, the transmembrane domain is the protein domain identified by SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:18, homolog or functional fragment thereof. In embodiments, the transmembrane domain includes the protein domain identified by SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:18, homolog or functional fragment thereof.

Likewise, the term "CD8α transmembrane domain" as provided herein includes any of the recombinant or naturally-occurring forms of the transmembrane domain of CD8α, or variants or homologs thereof that maintain CD8α transmembrane domain activity (e.g. within at least 50%, 80%, 90%, 95%, 96%, 97%, 98%, 99% or 100% activity compared to the CD8α transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD8α transmembrane domain polypeptide.

The term "CD4 transmembrane domain" as provided herein includes any of the recombinant or naturally-occurring forms of the transmembrane domain of CD4, or variants or homologs thereof that maintain CD4 transmembrane domain activity (e.g. within at least 50%, 80%, 90%, 95%, 96%, 97%, 98%, 99% or 100% activity compared to the CD4 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD4 transmembrane domain polypeptide.

The term "CD3-zeta transmembrane domain" as provided herein includes any of the recombinant or naturally-occurring forms of the transmembrane domain of CD3-zeta, or variants or homologs thereof that maintain CD3-zeta transmembrane domain activity (e.g. within at least 50%, 80%, 90%, 95%, 96%, 97%, 98%, 99% or 100% activity compared to the CD3-zeta transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD3-zeta transmembrane domain polypeptide.

In embodiments, the recombinant protein includes a spacer region connecting the non-CDR Fab binding peptide domain to the transmembrane domain. In embodiments, the spacer region is between the transmembrane domain and the non-CDR Fab binding peptide domain. In other words, the spacer region is directly or indirectly (e.g., through peptide linker) connected to the C-terminus of the non-CDR Fab binding peptide domain and directly or indirectly (e.g., through another peptide linker) connected to the N-terminus of the transmembrane domain. Thus, the recombinant protein provided herein may include a first peptide linker and a second peptide linker, wherein the first peptide linker connects the C-terminus of the non-CDR Fab binding peptide domain to the N-terminus of the spacer region and the second peptide linker connects the C-terminus of the spacer region to the N-terminus of the transmembrane domain.

A "spacer region" as provided herein is a polypeptide connecting the non-CDR Fab binding peptide domain with the transmembrane domain. In embodiments, the binding affinity of the non-CDR Fab binding peptide domain to an antigen-binding domain (e.g., Fab) is increased compared to the absence of the spacer region. In embodiments, the steric hindrance between the non-CDR Fab binding peptide domain and an antigen-binding domain (e.g., Fab) is decreased in the presence of the spacer region.

In embodiments, the spacer region includes an Fc region. Examples of spacer regions contemplated for the compositions and methods provided herein include without limitation, immunoglobulin molecules or fragments thereof (e.g., IgG1, IgG2, IgG3, IgG4) and immunoglobulin molecules or fragments thereof (e.g., IgG1, IgG2, IgG3, IgG4) including mutations affecting Fc receptor binding. In embodiments, the spacer region is a fragment of an IgG (e.g., IgG4), wherein said fragment includes a deletion of the CH2 domain. In embodiments, the spacer region is a fragment of an IgG (e.g., IgG4), wherein said fragment includes the CH3 region. In embodiments, the spacer region is a CH3 region. In embodiments, the spacer region includes a CH3 region. In embodiments, the spacer region is a CH2 region. In embodiments, the spacer region includes a CH2 region. The spacer region may be a peptide linker. In embodiments, the spacer region is a serine-glycine linker. In embodiments, the spacer region has the sequence GGSG. In embodiments, the spacer region includes the sequence GGSG. In embodiments, the spacer region has the sequence GSGSGSGS (SEQ ID NO:24). In embodiments, the spacer region includes the sequence GSGSGSGS (SEQ ID NO:24). In embodiments, the spacer region is at least 4 amino acids in length. In embodiments, the spacer region is about 4 amino acids in length. In embodiments, the spacer region is between 4 and 250 amino acids in length. The spacer region may include residues capable of extending the half-life in vivo (e.g., plasma) of the proteins provided herein. In embodiments, the spacer region is 10 amino acids in length. In embodiments, the spacer region is 229 amino acids in length. In embodiments, the spacer region is GGGSSGGGSG (SEQ ID NO:31). In embodiments, the spacer region includes the sequence GGGSSGGGSG (SEQ ID NO:31). The spacer region may be "pasylated." The term "pasylated" or "pasylation" is used in its customary sense and refers to an amino acid sequences, which due to their high content in proline, alanine and serine form highly soluble biological polymers. Thus, in embodiments, the spacer region includes about 200 proline, alanine and serine residues combined. In embodiments, the spacer region includes from about 10 to about 200 proline, alanine and serine residues combined. In embodiments, the spacer region includes hydrophilic residues. In embodiments, the recombinant protein does not include a spacer region.

In embodiments, the spacer region includes the sequence of SEQ ID NO:33. In embodiments, the spacer region has the sequence of SEQ ID NO:33.

In embodiments, the recombinant protein includes a peptide linker connecting the non-CDR Fab binding peptide domain to the spacer region. In embodiments, the peptide linker is between the non-CDR Fab binding peptide domain and the spacer region. In other words, the peptide linker is directly or indirectly (e.g., through peptide linker) connected to the C-terminus of the non-CDR Fab binding peptide domain and directly or indirectly (e.g., through another peptide linker) connected to the N-terminus of the spacer region. The peptide linker (e.g., first or second peptide linker) provided herein may be 5-50 amino acids in length.

In embodiments, the peptide linker (e.g., first or second peptide linker) is 5-45 amino acids in length. In embodiments, the peptide linker (e.g., first or second peptide linker) is 5-40 amino acids in length. In embodiments, the peptide linker (e.g., first or second peptide linker) is 5-35 amino acids in length. In embodiments, the peptide linker (e.g., first or second peptide linker) is 5-30 amino acids in length. In embodiments, the peptide linker (e.g., first or second peptide linker) is 5-25 amino acids in length. In embodiments, the peptide linker (e.g., first or second peptide linker) is 5-20 amino acids in length. In embodiments, the peptide linker (e.g., first or second peptide linker) is 5-15 amino acids in length. In embodiments, the peptide linker (e.g., first or second peptide linker) is 5-10 amino acids in length. In embodiments, the peptide linker (e.g., first or second peptide linker) is 5, 6, 7, 8, 9, 10, 11, 12, 13, 14, 15, 16, 17, 18, 19, 20, 21, 22, 23, 24, 25, 26, 27, 28, 29, 30, 31, 32, 34, 35 36, 37, 38, 39, 40, 41, 42, 43, 44, 45, 46, 47, 48, 49 or 50 amino acids in length. In embodiments, the peptide linker (e.g., first or second peptide linker) is 18 amino acids in length. In embodiments, the peptide linker has the sequence of SEQ ID NO:25. In embodiments, the peptide linker includes the sequence of SEQ ID NO:25. In embodiments, the peptide linker is the sequence SAPASSASAPSAASAPAG (SEQ ID NO:26).

In embodiments, the peptide linker is a first peptide linker and the recombinant protein includes a second peptide linker, wherein the second peptide linker connects the spacer region with the transmembrane domain. Thus, in embodiments, the second peptide linker is between the spacer region and the transmembrane domain. In other words, the first peptide linker is connected to the C-terminus of the non-CDR Fab binding peptide domain and connected to the N-terminus of the spacer region; and the second peptide linker is connected to the C-terminus of the spacer region and connected to the N-terminus of the transmembrane domain.

In embodiments, the recombinant protein provided herein includes an intracellular co-stimulatory signaling domain connecting the transmembrane domain to the intracellular T-cell signaling domain. In embodiments, the intracellular co-stimulatory signaling domain is between the transmembrane domain and the intracellular T-cell signaling domain. In other words, the intracellular co-stimulatory signaling domain is directly or indirectly (e.g., through a peptide linker) connected to the C-terminus of the transmembrane domain and directly or indirectly (e.g., through another peptide linker) connected to the N-terminus of the intracellular T-cell signaling domain.

An "intracellular co-stimulatory signaling domain" as provided herein includes amino acid sequences capable of providing co-stimulatory signaling in response to binding of an antigen to the antibody region provided herein including embodiments thereof. In embodiments, the signaling of the co-stimulatory signaling domain results in production of cytokines and proliferation of the T cell expressing the same. In embodiments, the intracellular co-stimulatory signaling domain is a CD28 intracellular co-stimulatory signaling domain, a 4-1BB intracellular co-stimulatory signaling domain, a ICOS intracellular co-stimulatory signaling domain, or an OX-40 intracellular co-stimulatory signaling domain. In embodiments, the intracellular co-stimulatory signaling domain includes a CD28 intracellular co-stimulatory signaling domain. In embodiments, the intracellular co-stimulatory signaling domain is a CD28 intracellular co-stimulatory signaling domain. In embodiments, the intracellular co-stimulatory signaling domain includes a 4-1BB intracellular co-stimulatory signaling domain. In embodiments, the intracellular co-stimulatory signaling domain is a 4-1BB intracellular co-stimulatory signaling domain. In embodiments, the intracellular co-stimulatory signaling domain is a CD28 intracellular co-stimulatory signaling domain, a 4-1BB intracellular co-stimulatory signaling domain, a ICOS intracellular co-stimulatory signaling domain, an OX-40 intracellular co-stimulatory signaling domain or any combination thereof.

Exemplary intracellular co-stimulatory signaling domains including sequences and accession numbers are listed in Table 2. In embodiments, the intracellular co-stimulatory signaling domain includes the protein identified by SEQ ID NO:12, SEQ ID NO:13, SEQ ID NO:14, SEQ ID NO:15 or SEQ ID NO:16. In embodiments, the intracellular co-stimulatory signaling domain is SEQ ID NO:12, SEQ ID NO:13, SEQ ID NO:14, SEQ ID NO:15 or SEQ ID NO:16. In embodiments, the intracellular co-stimulatory signaling domain is SEQ ID NO:13. In embodiments, the intracellular co-stimulatory signaling domain is SEQ ID NO:14.

In embodiments, the recombinant protein includes a detectable domain bound to the C-terminus of the intracellular T-cell signaling domain. In embodiments, detectable domain is a truncated CD19 (CD19t) domain. The term "CD19t" refers to a truncated CD19 protein lacking intracellular signaling capabilities. As used herein, truncated CD19 is an inert molecule which functions as a detectable domain to identify T cells including the recombinant proteins provided herein. In embodiments, the detectable domain includes the sequence of SEQ ID NO:22. In embodiments, the detectable domain is the sequence of SEQ ID NO:22.

In embodiments, the recombinant protein includes a self-cleaving peptidyl sequence connecting the intracellular T-cell signaling domain to the detectable domain. In embodiments, the self-cleaving peptidyl linker sequence is a T2A sequence or a 2A sequence. In embodiments, the self-cleaving peptidyl sequence is between the intracellular T-cell signaling domain and the detectable domain. In other words, the self-cleaving peptidyl sequence is directly or indirectly (e.g., through peptide linker) connected to the C-terminus of the intracellular T-cell signaling domain and directly or indirectly (e.g., through another peptide linker) connected to the N-terminus of the detectable domain.

In embodiments, the self-cleaving peptidyl linker has the sequence PVKQLLNFDLLKLAGDVESNPGP (SEQ ID NO:27). In embodiments, the self-cleaving peptidyl linker has the sequence of an equine rhinitis A virus sequence. In embodiments, the self-cleaving peptidyl linker has the sequence QCTNYALLKLAGDVESNPGP (SEQ ID NO:28). In embodiments, the self-cleaving peptidyl has the sequence of a porcine teschovirus 1 sequence. In embodiments, the self-cleaving peptidyl has the sequence ATNFSLLKQAGDVEENPGP (SEQ ID NO:29). In embodiments, the self-cleaving peptidyl linker has the sequence of a Thosea asigna virus sequence. In embodiments, the self-cleaving peptidyl linker has the sequence EGRGSLLTCGDVESNPGP (SEQ ID NO:30). In embodiments, the self-cleaving peptidyl linker has the sequence of SEQ ID NO:21. In embodiments, the self-cleaving peptidyl linker is the sequence of SEQ ID NO:21.

In embodiments, the recombinant protein forms part of a cell. In embodiments, the recombinant protein forms part of a T cell. In embodiments, the transmembrane domain forms part of the cell membrane of the T cell.

As described above the recombinant protein provided herein may bind to an antigen-binding domain. While the elements of the recombinant protein provided herein including embodiments thereof (e.g., non-CDR Fab binding peptide domain, transmembrane domain, intracellular T-cell signaling domain, intracellular co-stimulatory signaling domain) are covalently bound to each other and thereby form a continuous single chain polypeptide, the recombinant protein binds the antigen-binding domain non-covalently. In embodiments, the non-CDR Fab binding peptide domain is bound to an antigen-binding domain. In embodiments, the non-CDR Fab binding peptide domain is non-covalently bound to an antigen-binding domain.

As described above, the antigen-binding domain may be a Fab, an IgG, or a bispecific antibody. In embodiments, the antigen-binding domain is a cetuximab meditope-enabled domain, trastuzumab meditope-enabled domain, pertuzumab meditope-enabled domain, M5A meditope-enabled domain or rituximab meditope-enabled domain. In embodiments, the antigen-binding domain is capable of binding to a cancer antigen. In embodiments, the antigen-binding domain is capable of binding to a cancer antigen. In embodiments, the antigen-binding domain is capable of non-covalently binding to a cancer antigen. In embodiments, the cancer antigen is Her2, EGFR, CD19 or CD20. In embodiments, the cancer antigen forms part of a cell. In embodiments, the cancer antigen is expressed on the surface of a cell. In embodiments, the cell is a cancer cell. In embodiments, the cancer is an ovarian cancer, renal cell carcinoma, a B-cell malignancy, leukemia, lymphoma, breast cancer, colorectal cancer, prostate cancer, neuroblastoma, melanoma, medulloblastoma, lung cancer, osteosarcoma, glioblastoma or glioma.

The compositions provided herein may include a plurality (i.e. more than one, at least two) of a recombinant protein provided herein including embodiments thereof. Where a composition includes more than one recombinant protein provided herein including embodiments thereof, the recombinant proteins are referred to herein as first, second, third, fourth etc. recombinant protein. Accordingly, the elements forming part of said first, second, third fourth etc. recombinant protein are referred to herein as first, second third or fourth non-CDR Fab binding peptide domain, first, second third or fourth intracellular T-cell signaling domain, first, second third or fourth transmembrane domain, first, second third or fourth spacer region or first, second third or fourth intracellular co-stimulatory signaling domain, respectively. Where a composition includes a plurality of recombinant proteins provided herein including embodiments thereof, the recombinant proteins may be different or the same. In other words, the recombinant proteins may include the same domains or different domains (e.g., non-CDR Fab binding peptide domain, intracellular T-cell signaling domain, transmembrane domain, spacer region, intracellular co-stimulatory signaling domain) or they may be able to bind the same or different antigen-binding domains.

Where the compositions provided herein include a plurality of recombinant proteins provided herein, the recombinant proteins may dimerize with each other through non-covalent binding of their respective spacer regions. For example, the first recombinant protein may include a first CH3 domain, which non-covalently binds to the second CH3 domain of the second recombinant protein. Thus, in embodiments, the recombinant protein is a first recombinant protein, the non-CDR Fab binding peptide domain is a first non-CDR Fab binding peptide domain, the intracellular T-cell signaling domain is a first intracellular T-cell signaling domain, the transmembrane domain is a first transmembrane domain, the spacer region is a first spacer region and the intracellular co-stimulatory signaling domain is a first intracellular co-stimulatory signaling domain.

In embodiments, the first recombinant protein is non-covalently bound to a second recombinant protein, the second recombinant protein includes: (i) a second non-CDR Fab binding peptide domain; (ii) a second intracellular T-cell signaling domain; (iii) a second transmembrane domain connecting the second non-CDR Fab binding peptide domain to the second intracellular T-cell signaling domain; and (iv) a second spacer region, wherein the second spacer region connects the second non-CDR Fab binding peptide domain to the second transmembrane domain, wherein the first spacer region is non-covalently bound to the second spacer region. In embodiments, the first spacer region and the second spacer region are a first constant heavy chain 3 (CH3) domain and a second constant heavy chain 3 (CH3) domain.

In embodiments, the first non-CDR Fab binding peptide domain and the second non-CDR Fab binding peptide domain are chemically different. In embodiments, the first non-CDR Fab binding peptide domain and the second non-CDR Fab binding peptide domain are chemically the same.

In embodiments, the first non-CDR Fab binding peptide domain is non-covalently bound to a first antigen-binding domain. In embodiments, the second non-CDR Fab binding peptide domain is non-covalently bound to a second antigen-binding domain. In embodiments, the first antigen-binding domain and the second antigen-binding domain are chemically different or the same. In embodiments, the first antigen-binding domain and the second antigen-binding domain are independently a cetuximab meditope-enabled domain, trastuzumab meditope-enabled domain, pertuzumab meditope-enabled domain, M5A meditope-enabled domain or rituximab meditope-enabled domain.

In one embodiment, the recombinant protein includes a non-CDR Fab binding peptide domain of SEQ ID NO:32, a spacer region of SEQ ID NO:33, a CD28 transmembrane domain of SEQ ID NO:18, an CD28 intracellular co-stimulatory signaling domain of SEQ ID NO:13, a CD3ζ intracellular T-cell signaling domain of SEQ ID NO:34, a self cleaving peptidyl linker sequence of SEQ ID NO:21 and a detectable domain of SEQ ID NO:22.

In one embodiment, the recombinant protein includes a non-CDR Fab binding peptide domain of SEQ ID NO:32, a spacer region of SEQ ID NO:33, a CD28 transmembrane domain of SEQ ID NO:18, a 4-1BB intracellular co-stimulatory signaling domain of SEQ ID NO:14, a CD3ζ intracellular T-cell signaling domain of SEQ ID NO:34, a self cleaving peptidyl linker sequence of SEQ ID NO:21 and a detectable domain of SEQ ID NO:22.

In one embodiment, the recombinant protein includes a non-CDR Fab binding peptide domain of SEQ ID NO:32, a spacer region of SEQ ID NO:33, a CD28 transmembrane domain of SEQ ID NO:18, an CD28 intracellular co-stimulatory signaling domain of SEQ ID NO:13, and a CD3ζ intracellular T-cell signaling domain of SEQ ID NO:34.

In one embodiment, the recombinant protein includes a non-CDR Fab binding peptide domain of SEQ ID NO:32, a spacer region of SEQ ID NO:33, a CD28 transmembrane domain of SEQ ID NO:18, a 4-1BB intracellular co-stimulatory signaling domain of SEQ ID NO:14, and a CD3ζ intracellular T-cell signaling domain of SEQ ID NO:34.

In one embodiment, the recombinant protein includes a non-CDR Fab binding peptide domain of SEQ ID NO:32, a peptide linker of SEQ ID NO:25, a spacer region of SEQ ID NO:33, a CD28 transmembrane domain of SEQ ID NO:18, an CD28 intracellular co-stimulatory signaling domain of SEQ ID NO:13, a CD3ζ intracellular T-cell signaling domain of SEQ ID NO:34, a self cleaving peptidyl linker sequence of SEQ ID NO:21 and a detectable domain of SEQ ID NO:22.

In one embodiment, the recombinant protein includes a non-CDR Fab binding peptide domain of SEQ ID NO:32, a peptide linker of SEQ ID NO:25, a spacer region of SEQ ID NO:33, a CD28 transmembrane domain of SEQ ID NO:18, a 4-1BB intracellular co-stimulatory signaling domain of SEQ ID NO:14, a CD3ζ intracellular T-cell signaling domain of SEQ ID NO:34, a self cleaving peptidyl linker sequence of SEQ ID NO:21 and a detectable domain of SEQ ID NO:22.

In embodiments, the recombinant protein includes a signal peptide of SEQ ID NO:37. In embodiments, the signal peptide is bound to the N-terminus of the non-CDR Fab binding peptide domain.

In one embodiment, the recombinant protein includes a non-CDR Fab binding peptide domain of SEQ ID NO:32, a peptide linker of SEQ ID NO:25, a spacer region of SEQ ID NO:33, a CD28 transmembrane domain of SEQ ID NO:18, an CD28 intracellular co-stimulatory signaling domain of SEQ ID NO:13, and a CD3ζ intracellular T-cell signaling domain of SEQ ID NO:34.

In one embodiment, the recombinant protein includes a non-CDR Fab binding peptide domain of SEQ ID NO:32, a peptide linker of SEQ ID NO:25, a spacer region of SEQ ID NO:33, a CD28 transmembrane domain of SEQ ID NO:18, a 4-1BB intracellular co-stimulatory signaling domain of SEQ ID NO:14, and a CD3ζ intracellular T-cell signaling domain of SEQ ID NO:34.

In one embodiment, the recombinant protein includes the sequence of SEQ ID NO:35. In one embodiment, the recombinant protein is the sequence of SEQ ID NO:35. In one embodiment, the recombinant protein includes the sequence of SEQ ID NO:36. In one embodiment, the recombinant protein is the sequence of SEQ ID NO:36.

In embodiments, the recombinant protein includes from the N-terminus to the C-terminus: a non-CDR Fab binding peptide domain, spacer region, a CD28 transmembrane domain, a CD28 intracellular co-stimulatory signaling domain, a CD3ζ intracellular T-cell signaling domain, a self cleaving peptidyl linker sequence and a detectable domain.

In embodiments, the recombinant protein includes from the N-terminus to the C-terminus: a non-CDR Fab binding peptide domain, spacer region, a CD28 transmembrane domain, a 4-1BB intracellular co-stimulatory signaling domain, a CD3ζ intracellular T-cell signaling domain, a self cleaving peptidyl linker sequence and a detectable domain.

In embodiments, the recombinant protein includes from the N-terminus to the C-terminus: a non-CDR Fab binding peptide domain, spacer region, a CD28 transmembrane domain, a CD28 intracellular co-stimulatory signaling domain and a CD3ζ intracellular T-cell signaling domain.

In embodiments, the recombinant protein includes from the N-terminus to the C-terminus: a non-CDR Fab binding peptide domain, spacer region, a CD28 transmembrane domain, a 4-1BB intracellular co-stimulatory signaling domain, and a CD3ζ intracellular T-cell signaling domain.

In embodiments, the recombinant protein includes from the N-terminus to the C-terminus: a non-CDR Fab binding peptide domain, a peptide linker, spacer region, a CD28 transmembrane domain, a CD28 intracellular co-stimulatory signaling domain, a CD3ζ intracellular T-cell signaling domain, a self cleaving peptidyl linker sequence and a detectable domain.

In embodiments, the recombinant protein includes from the N-terminus to the C-terminus: a non-CDR Fab binding peptide domain, a peptide linker, spacer region, a CD28 transmembrane domain, a 4-1BB intracellular co-stimulatory signaling domain, a CD3ζ intracellular T-cell signaling domain, a self cleaving peptidyl linker sequence and a detectable domain.

In embodiments, the recombinant protein includes from the N-terminus to the C-terminus: a non-CDR Fab binding peptide domain, a peptide linker, spacer region, a CD28 transmembrane domain, a CD28 intracellular co-stimulatory signaling domain, and a CD3ζ intracellular T-cell signaling domain.

In embodiments, the recombinant protein includes from the N-terminus to the C-terminus: a non-CDR Fab binding peptide domain, a peptide linker, spacer region, a CD28 transmembrane domain, a 4-1BB intracellular co-stimulatory signaling domain, and a CD3ζ intracellular T-cell signaling domain.

Nucleic Acid Compositions

Provided herein are nucleic acids encoding the recombinant protein provided herein including embodiments thereof. Thus, in one aspect is provided a nucleic acids encoding the recombinant protein provided herein including embodiments thereof. In another aspect is provided an expression vector including the nucleic acid provided herein including embodiments thereof. In embodiments, the expression vector is a lentivirus or onco-retrovirus. In embodiments, the expression vector is a lentivirus. In embodiments, the expression vector is a an onco-retrovirus.

Cell Compositions

The recombinant proteins and nucleic acids provided herein may form part of a cell (i.e, are included and/or expressed by a cell. Thus, in an aspect, a T lymphocyte including the expression vector provided herein including embodiments thereof is provided.

In another aspect, a T lymphocyte including the recombinant protein provided herein including embodiments thereof is provided. Parts of the recombinant protein provided herein may form part of the cell membrane of the cell it is expressed by. The transmembrane domain is capable of spanning the cellular membrane of e.g., a T cell from one side of the membrane through to the other side of the membrane. In embodiments, the transmembrane domain spans from the intracellular side to the extracellular side of a cellular membrane. Therefore, the non-CDR Fab binding peptide domain and the spacer region are located on the extracellular side of the cellular membrane, while the intracellular T-cell signaling domain are located on the intracellular side of the cell. In embodiments, the transmembrane domain is within the cell membrane of the T lymphocyte. In embodiments, the T-lymphocyte is an autologous T-lymphocyte. In embodiments, the T-lymphocyte is a heterologous T-lymphocyte.

In embodiments, then on-CDR Fab binding peptide domain is bound to an antigen-binding domain. In embodiments, the antigen-binding domain is a Fab, an IgG, or a bispecific antibody. In embodiments, the antigen-binding domain is bound to a cancer antigen.

The antigen binding domain may be an antibody including a first Fab domain and a second Fab domain and the recombinant protein may bind to the non-CDR binding site of the first Fab domain and the second Fab domain may bind the cancer antigen. In embodiments, the recombinant protein binds to the non-CDR binding site of the first Fab domain and the first Fab domain binds the cancer antigen. In embodiments, the recombinant protein binds to the non- CDR binding site of the first Fab domain, and the first Fab domain binds a first cancer antigen and the second Fab domain binds a second cancer antigen. In embodiments, the first recombinant protein binds to the non-CDR binding site of the first Fab domain, and the second recombinant protein binds to the non-CDR binding site of the second Fab domain. In a further embodiment, the first Fab domain binds a first cancer antigen and the second Fab domain binds a second cancer antigen.

In embodiments, the cancer antigen is Her2, EGFR, CD19 or CD20. In embodiments, the antigen-binding domain is a cancer antigen-binding domain. In embodiments, the antigen-binding domain is a cetuximab meditope-enabled domain, trastuzumab meditope-enabled domain, pertuzumab meditope-enabled domain, M5A meditope-enabled domain or rituximab meditope-enabled domain.

Methods of Treatment

The compositions provided herein, including embodiments thereof, are, inter alia, useful in providing effective treatments for diseases such as cancer. Thus, in an aspect, a method of treating cancer is provided. The method includes administering to a subject in need thereof an effective amount of a T lymphocyte provided herein including embodiments thereof and an effective amount of an antigen-binding domain capable of binding to the non-CDR Fab binding peptide domain, wherein the antigen-binding domain is a cancer antigen-binding domain.

In embodiments, the T-lymphocyte and the antigen-binding domain are administered simultaneously or sequentially. In embodiments, the T-lymphocyte and the antigen-binding domain are administered simultaneously.

The T-lymphocyte and the antigen-binding domain may be administered in combination either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of the T-lymphocyte and the antigen-binding domain. In embodiments, where the T-lymphocyte and the antigen-binding domain are administered sequentially, the T-lymphocyte is administered at a first time point and the antigen-binding domain is administered at a second time point, wherein the first time point precedes the second time point. The course of treatment is best determined on an individual basis depending on the particular characteristics of the subject and the type of treatment selected. The treatment, such as those disclosed herein, can be administered to the subject on a daily, twice daily, bi-weekly, monthly or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly). Thus, in embodiments, the T-lymphocyte and the antigen-binding domain are administered simultaneously or sequentially.

In embodiments, the T-lymphocyte is administered at a first time point and the antigen-binding domain is administered at a second time point, wherein the first time point precedes the second time point. In embodiments, the second time point is within less than about 120, 90, 60, 50, 40, 30, 20, 19, 18, 17, 16, 15, 14, 13, 12, 10, 11, 9, 8, 7, 6, 5, 4, 3, 2 or 1 days from the first time point. In embodiments, the second time point is within less than about 120 days from the first time point. In embodiments, the second time point is within less than about 90 days from the first time point. In embodiments, the second time point is within less than about 60 days from the first time point. In embodiments, the second time point is within less than about 50 days from the first time point. In embodiments, the second time point is within less than about 40 days from the first time point. In embodiments, the second time point is within less than about 30 days from the first time point. In embodiments, the second time point is within less than about 20 days from the first time point.

In embodiments, the antigen-binding domain is administered at a first time point and the T-lymphocyte is administered at a second time point, wherein the first time point precedes the second time point. In embodiments, the second time point is within less than about 120, 90, 60, 50, 40, 30, 20, 19, 18, 17, 16, 15, 14, 13, 12, 10, 11, 9, 8, 7, 6, 5, 4, 3, 2 or 1 days from the first time point. In embodiments, the second time point is within less than about 120 days from the first time point. In embodiments, the second time point is within less than about 90 days from the first time point. In embodiments, the second time point is within less than about 60 days from the first time point. In embodiments, the second time point is within less than about 50 days from the first time point. In embodiments, the second time point is within less than about 40 days from the first time point. In embodiments, the second time point is within less than about 30 days from the first time point. In embodiments, the second time point is within less than about 20 days from the first time point.

In embodiments, the T-lymphocyte and the antigen-binding domain are admixed prior to the administering. In embodiments, the method includes: (i) prior to the administering allowing the non-CDR Fab binding peptide domain to bind the antigen-binding domain in vitro, thereby forming a T-lymphocyte-recombinant protein complex; and (ii) administering the T-lymphocyte-recombinant protein complex to the subject, thereby treating cancer in the subject.

In embodiments, the T-lymphocyte and the antigen-binding domain are administered sequentially. In embodiments, the T-lymphocyte is administered at a first time point and said antigen-binding domain is administered at a second time point, wherein the first time point precedes the second time point. In embodiments, the antigen-binding domain is administered at a first time point and said T-lymphocyte is administered at a second time point, wherein the first time point precedes the second time point.

In embodiments, the cancer is ovarian cancer, renal cell carcinoma, a B-cell malignancy, leukemia, lymphoma, breast cancer, colorectal cancer, prostate cancer, neuroblastoma, melanoma, medulloblastoma, lung cancer, osteosarcoma, glioblastoma or glioma. In embodiments, the antigen-binding domain is a cetuximab meditope-enabled domain, trastuzumab meditope-enabled domain, pertuzumab meditope-enabled domain, M5A meditope-enabled domain or rituximab meditope-enabled domain.

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

The term "associated" or "associated with" in the context of a substance or substance activity or function associated with a disease (e.g., cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) is caused by (in whole or in part), or a symptom of the disease is caused by (in whole or in part) the substance or substance activity or function.

"Chemotherapeutic" or "chemotherapeutic agent" is used in accordance with its plain ordinary meaning and refers to a chemical composition or compound having antineoplastic properties or the ability to inhibit the growth or proliferation of cells.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by using a method as described herein), results in reduction of the disease or one or more disease symptoms.

EXAMPLES

CAR T cells have demonstrated remarkable success to treat liquid tumors and are being rapidly expanded to treat solid tumors and other diseases. The current approach is to create CAR T cells that target a single antigen. While effective at eliminating tumor cells expressing the specified antigen, tumor cells that do not express the antigen are spared and can proliferate, often becoming more aggressive. Thus, to target these cells, an entirely new CAR T cell expressing different tumor targeting scFv needs to be created. Herein, Applicants address this issue using the meditope technology. Specifically, Applicants replace the tumor targeting scFv with an ultrahigh affinity meditope (non-CDR Fab binding peptide domain). Tumor specificity is added subsequently using antigen-specific, meditope-enabled Fabs or mAbs (antigen binding domain).

Applicants use the meditope-interaction to create a universal CAR T cell. Specifically, Applicants have replaced the antigen targeting region with a meditope (non-CDR Fab binding peptide domain), demonstrated that Applicants could add meditope-enabled Fab/mAbs, and that Applicants could bind the antigen specific to the Fab. The advantage here is that Applicants can make a meditope-zeta chain T cell and swap in meditope-enabled Fabs specific to the disease or to cover multiple antigens.

The CAR T cell field is rapidly developing and as clinical results become available, there is a demonstrated need to alter the specificity of CAR T cells. Applicants present a universal CAR T cell platform wherein Applicants replace the scFv within the CAR T cell with a meditope (e.g., non-CDR Fab binding peptide domain) and use meditope-enabled mAbs/Fabs (antigen binding domains) to add antigen specificity. This platform technology allows Applicants to rapidly and efficiently alter the target specificity without creating and optimizing individual CAR T cells. Applicants show proof of concept through FACs using two different meditope-enabled mAbs. Applicants can optimize linker design and docking and will demonstrate the efficacy in animal models by altering antigen specificity of the meditope-CAR in situ.

A single T cell expressing a meditope can be mixed and matched with Fabs/Mabs targeting different antigens/epitopes within the tumor, potentially producing a superior product that can be applied to multiple forms of cancer. Fabs/mAbs are generally more stable than scFvs, generally have higher affinity for antigens than scFvs, and a panel of Fabs that bind to different epitopes on the antigen are readily produced allowing for rapid optimization (e.g., a current issue within the field is how the distance between the receptor epitope and tumor membrane affects efficacy).

Applicants can package the meditope in a lentivirus to produce FabRacks (recombinant proteins provided herein) and characterize tumor eradication in vitro and in vivo. Applicants can alter specificity in situ and characterize. Applicants can alter linker (e.g., remove CH3 domain) to create monovalent FabRacks, produce, characterize, and alter specificity.

Conventional CAR and meditope CAR: basic concept. scFv variant is used in the clinic. The 'simplest' FabRack is bound to a meditope-enabled IgG or Fab fragment. Of note, this is not limited to IgG or Fabs, we can make bi-specific IgGs or Bionics or single arm fabs. Basically, anything we can fuse to a Fab that has been meditope-enabled.

Fabrack-T cell can be bound to a tumor cell, mediated by an meditope-enabled IgG. There are multiple combinations/interactions that can lead to a productive interaction. One Fab arm binds to the Fabrack T Cell and the other arm binds to the tumor cell. The same Fab arm binds to the FABrack T Cell and the tumor antigen. Both Fab arms bind to the tumor and one or the other Fab arms binds to the Fabrack T cell. Both Fab arms bind to the Fabrack T Cell and to the tumor. Etc.

Meditope CAR constructs can be packed in a lentivirus vector. The extracellular domain include meditope (non-CDR Fab binding peptide domain), linker (peptide linker) and CH3 domain of IgG (spacer region) and is followed by CD28 transmembrane domain (CD28tm), CD28 costimulatory domain (CD28) and CD3$\zeta$ cytolytic domain (also referred to herein as intracellular T-cell signaling domain) (CD3$\zeta$). CD3$\zeta$ and CD19t are separated by a T2A sequence. memAb (meditope-enabled monoclonal antibody) can be bound to target cells and FabRack expressing Jurkat cells harboring NFAT responsive luciferase. This is a simple readout to test the concept before moving to T cells.

The memAb (meditope-enabled monoclonal antibody; antigen binding domain) may be pre-bound to FabRack cells (T cells expressing the recombinant proteins provided herein) or the memAb (antigen binding domain) may be prebound to the target cells (e.g., cancer cell). The level of antigen expression on the target cell affects the activation of the T cell. T cell activation is comparable for T cells with memAb pre-binding and cancer cells with memAb pre-binding, where the antigen expression on the cancer cell is low. Highest T cell activation can be achieved when cancer cells are pre-bound with memAb and if the antigen expression on the cancer is high. Similarly, at high antigen expression levels on the cancer, the activation of T cells is high, when the T cells a pre-bound to the memAb (meditope-enabled monoclonal antibody, antigen binding domain). See FIG. 19.

Materials and Methods

Cloning. Parental anti-Her2 scFv_IgG4op(HL-CH3)_CD28gg_op-Zeta_op-T2A-CD19t_epHIV7 vector kindly provided by Dr. C. Brown. GM-CSFr secretion signal_meditope_PASlinker17 gene cassette was synthesized by DNA2.0 and inserted into CAR vector, with or without IgG4op(HL-CH3) domain (Meditope-CH3 and Meditope-CD28, respectively) using NheI and SbfI restriction sites. Cloned plasmids were purified using MaxiPrep kit (Qiagen).

Fluorophore labeling of soluble protein. Alexa Fluor dyes (ThermoFisher) were attached to soluble protein using amine conjugation according to manufacturer's protocol. Briefly, Alexa Fluor 647 NHS Ester dye was conjugated to trastuzumab I83E IgG and Fab and ipilimumab IgG. Degree of label (DOL) was calculated, using $A_{280}$ and $A_{max}$, to be between $1 \leq DOL \leq 3$ dye per molecule. Pacific Blue NHS Ester dye was conjugated to sHer2. Protein interactions were characterized by size-exclusion chromatography (SEC) prior to FACS assay to assess binding activity.

Transfection. On Day 0, CHO-S cells (Invitrogen) at passage 9 were transfected either with no vector (Mock) or Parental CAR, Meditope-CH3, or Meditope-CD28 vectors. Cells were transfected using FreeStyle MAX transfection kit (ThermoFisher) according to manufacturer's protocol.

Flow cytometry. On Day 5, cells were harvested and counted. 3E6 cells were added to 5 mL FACS tubes (VWR) and QS'd to 1E6 cells/mL with FACS stain solution (2% FCS, 0.5% NaN$_3$ in Hanks' Balanced Salt Solution, Batch #05092016). 0.1E6 cells were added to each well of V-bottom 96-well plate (Corning Costar), 3 wells per condition. Cells were washed twice with 100 µL stain solution, spun 300 g for 3 min at 4° C., and supernatant decanted. Cells were resuspended in 100 µL primary staining solution (PE-Cy7^CD-19 diluted 1:100 and 100 nM 647^IgG, 100 nM 647^Ipi, or 200 nM 647^Fab) for 30 min at 4° C. protected from light. Cells were washed twice with 100 µL stain solution and resuspended in secondary staining solution (200 nM PacBlue^Her2) for 30 min at 4° C. protected from light. Cells were washed twice with 100 µL stain solution and resuspended in 150 µL PI solution (PI diluted 1:100 in stain solution). Cell samples were analyzed using MACSQuant instrument (#2, West side of Brown lab), using 40 µL per sample. Voltage as follows: FSC=358 V, SSC=520 V. Channels for analysis: PE (PI), PE-Cy7 (CD19), APC (647), and VioBlue (Her2). Gating strategy:

FSC/SSC→PE$^-$→PE-Cy7$^+$→APC$^+$→VioBlue$^+$

FSC/SSC→PI$^-$→CD19$^+$→647$^+$→Her2$^+$

Animal Plan. Each group has four mice.

1. Tumor only: either OVCAR3-luc or SKOV3-luc is good
2. Tumor with HER-2 CAR T cells: either Fab CAR or scFv CAR T cell is good. 1E7 positive cells each mice.
3. Tumor with mock T cells: 1E7 mock T cells each mice.
4. Tumor with meditope-CAR T cells: 1E7 positive CAR T cells each mice.
5. Tumor with mock T cells+HER2 antibody with premix: 1E7 mock T cells each mice. HER2 antibody ip 4 mg/kg one day prior to T cells injection. T cells are premixed with 100 nM antibody and washed out. Antibody is given ip 4 mg/kg twice a week for two weeks.
6. Tumor with meditope-CAR T cells+HER2 antibody with premix: 1E7 CAR T cells each mice. HER2 antibody ip 4 mg/kg one day prior to T cells injection. T cells are premixed with 100 nM antibody and washed out. Antibody is given ip 4 mg/kg twice a week for two weeks.
7. Tumor with meditope-CAR T cells+HER2 antibody without premix: 1E7 CAR T cells each mice. HER2 antibody ip 4 mg/kg one day prior to T cells injection. T cells are not premixed with antibody. Antibody is given ip 4 mg/kg twice a week

| | Medi-CAR T cells | Mock T cells | HER2-CAR T cells | Tumor cells | Antibody |
|---|---|---|---|---|---|
| cells or Ab each mouse | 10^7 | 10^7 | 10^7 | 10^7 | 0.25 mg (50 g) × 4 |
| Total cells | 120 million (12 mice) | 80 million (8 mice) | 40 million (4 mice) | 700 million (28 mice) | 1 mg × 12 |

Fabrack Animal Data

Method (OVCAR3)

Five million OVCAR3-gfp-luc cells were intraperitoneally (ip) injected into mice on day 1. In mice treated with Fabrack T cells (group 6 and 7), mice were given 4 mg/kg memAb trastuzumab every 3 days (total 5 doses) and the first dose of Ab was given on day 8. Ten million human T cells were ip injected into mice on day 9. In group 6, Fabrack T cells were premixed with memAb and washed out. The tumor burden of mice was measured by luminescence after 150l of luciferin (28.57 mg/ml) was ip injected into mice. (group1: tumor only; group2: mock T cells; group3: Fabrack T cells only; group4: mock T cells+Ab; group5: HER2 scFv CAR; group 6: Fabrack T cells (premix)+Ab; group 7: Fabrack T cells+Ab)

Result (OVCAR3)

Mice show a substantial decrease in tumor size when they are given Fabrack T cells and memAb (group 6 and 7) independent of whether the Fabrack T cells were premixed with memAb or not. However, tumor relapsed around day 14. The relapse of tumor was not due to HER2 antigen loss based on flow cytometry result showing HER2+ tumor cells in mice abdominal fluids. The relapse of tumor may be due to the non-persistence of T cells since there are only few Fabrack T cells left in mice blood and abdominal fluids. Dosing schedules to optimize tumor eradication are underway.

Method (MCF7)

Five million MCF7-gfp-luc cells were intraperitoneally (ip) injected into mice on day 1. In Fabrack group, mice were given 4 mg/kg memAb trastuzumab around every 4 days and the first dose of Ab were ip injected with T cells together. First dose of two million human T cells were ip injected into mice on day 8. Two million Fabrack T cells were further given around every 6 days. The tumor burden of mice was measured by luminescence after 150l of luciferin (28.57 mg/ml) was ip injected into mice.

Result (MCF7)

The decrease in tumor size was seen in mice given Fabrack T cells and memAb on d11 and d14. However, the relapse of tumor were seen on day 16. Analysis of mice blood on day 22 showed that Fabrack T cells existed and memAb were bound to Fabrack T cells. Analysis of mice abdominal fluids on day 45 showed no antigen escape of tumor cells. The relapse of tumor may due to the hook effect from Ab, the dose of which may saturate the Ab-binding sites on tumor and T cells. The dose of Fabrack T cells was two million in MCF7 xenograft study compared to ten millions in OVCAR3 study so there were fewer Fabrack T cells for Ab binding. In addition MCF7 and OVCAR3 are low HER2 expression so their HER2 are easily saturated by Ab. Dosing schedules to optimize tumor eradication are underway.

In some aspects, the antibodies include a heavy chain variable (VH) region and/or a light chain variable (VL) region. In some aspects, the VL region has an amino acid sequence comprising a threonine, serine, or aspartate at position 40, a residue other than glycine at position 41, and/or an aspartate or asparagine at position 85, according to Kabat numbering, and/or comprises an isoleucine or leucine at position 10 and isoleucine at position 83, according to Kabat numbering, and/or comprises a valine or isoleucine at position 9 and a residue other than glutamine at position 100, according to Kabat numbering. In some examples, the amino acid sequence of the VL region has a threonine at position 40, an asparagine at position 41, and an aspartate at position 85, according to Kabat numbering.

In some aspects, the VH region has an amino acid sequence comprising a serine or proline at position 40 and an isoleucine, tyrosine, methionine, phenylalanine, or tryptophan at position 89, according to Kabat numbering. In some examples, the amino acid sequence of the VH region has a serine at position 40 and an isoleucine at position 89, according to Kabat numbering.

TABLES

TABLE 1

Examples of transmembrane domains.

| Protein | NCBI Accession No. | Length | Transmembrane Domain Sequence |
|---|---|---|---|
| CD3z | GI:623041 | 21 aa | LCYLLDGILFIYGVILTALFL (SEQ ID NO: 1) |
| CD28 | GI:340545506 | 27aa | FWVLVVVGGVLACYSLLVTVA FIIFWV (SEQ ID NO: 2) |
| CD4 | GI:179143 | 22aa | MALIVLGGVAGLLLFIGLGIFF (SEQ ID NO: 3) |
| CD8 | GI:225007534 | 21aa | IYIWAPLAGTCGVLLLSLVIT (SEQ ID NO: 4) |
| CD8 | GI:225007534 | 23aa | IYIWAPLAGTCGVLLLSLVITLY (SEQ ID NO: 5) |
| CD8 | GI:225007534 | 24aa | IYIWAPLAGTCGVLLLSLVITLY C (SEQ ID NO: 6) |
| 41BB | GI:315259099 | 27aa | IISFFLALTSTALLFLLFF LTLRFSVV (SEQ ID NO: 7) |
| OX40 | GI:315360637 | 21 aa | VAAILGLGLVLGLLGPLAILL (SEQ ID NO: 8) |
| ICOS | GI:251823951 | 21aa | FWLPIGCAAFVVVCILGCILI (SEQ ID NO: 9) |
| CD62L | GI:262206314 | 23aa | PLFIPVAVMVTAFSGLAFIIWLA (SEQ ID NO: 10) |

TABLE 2

Examples of signaling domains.

| Protein | NCBI Accession No. | Length | Endo Signaling |
|---|---|---|---|
| CDζ | GI:623041 | 113 aa | SEQ ID NO: 11: RVKFSRSADAPAYQQGQNQLYNELN LGRREEYDVLDKRRGRDPEMGGKPQ RRKNPQEGLY |
| CD28 | GI:340545506 | 42aa | SEQ ID NO: 12: RSKRSRLLHSDYMNMTPRRPGPTRK HYQPYAPPRDFAAYRS |
| CD28gg* | GI:340545506 | 42aa | SEQ ID NO: 13: RSKRSRGGHSDYMNMTPRRPGPTRK HYQPYAPPRDFAAYRS (ref) |
| 41BB | GI:315259099 | 42aa | SEQ ID NO: 14: KRGRKKLLYIFKQPFMRPVQTTQEE DGCSCRFPEEEEGGCEL |
| OX40 | GI:315360637 | 42aa | SEQ ID NO: 15: ALYLLRRDQRLPPDAHKPPGGGSFR TPIQEEQADAHSTLAKI |
| ICOS | GI:251823951 | 38 aa | SEQ ID NO: 16: CWLTKKKYSSSVHDPNGEYMFMRAV NTAKKSRLTDVTL |

P EMBODIMENTS

Embodiment P1. A first recombinant protein comprising: (i) a first non-CDR Fab binding peptide domain; (ii) a first intracellular T-cell signaling domain; and (iii) a first transmembrane domain connecting said first non-CDR Fab binding peptide domain to said first intracellular T-cell signaling domain.

Embodiment P2. The first recombinant protein of embodiment P1, further comprising a first spacer region connecting said first non-CDR Fab binding peptide domain to said first transmembrane domain.

Embodiment P3. The first recombinant protein of embodiment P2, wherein said first spacer region is a first CH3 region.

Embodiment P4. The first recombinant protein of embodiment P3, wherein said first recombinant protein is non-covalently bound to a second recombinant protein, said second recombinant protein comprising: (i) a second non-CDR Fab binding peptide domain; (ii) a second intracellular T-cell signaling domain; (iii) a second transmembrane domain connecting said second non-CDR Fab binding peptide domain to said second intracellular T-cell signaling domain; and (iv) a second spacer region, wherein said second spacer region connects said second non-CDR Fab binding peptide domain to said second transmembrane domain, wherein said second spacer region comprises a second CH3 region and wherein said first CH3 region is bound to said second CH3 region.

Embodiment P5. The first recombinant protein of any one of embodiments P1-P5, wherein said first non-CDR Fab binding peptide domain and said second non-CDR Fab binding peptide domain are chemically different.

Embodiment P6. The first recombinant protein of any one of embodiments P1-P5, wherein said first non-CDR Fab binding peptide domain and said second non-CDR Fab binding peptide domain are chemically the same.

Embodiment P7. The first recombinant protein of any one of embodiments P1-P6, wherein said first and said second intracellular T-cell signaling domain are independently a CD3 (intracellular T-cell signaling domain.

Embodiment P8. The first recombinant protein of any one of embodiments P1-P7, wherein said first non-CDR Fab binding peptide domain is non-covalently bound to a first antigen-binding domain.

Embodiment P9. The first recombinant protein of any one of embodiments P1-P8, wherein said second non-CDR Fab binding peptide domain is non-covalently bound to a second antigen-binding domain.

Embodiment P10. An isolated nucleic acid encoding the first recombinant protein of any one of embodiments 1-3.

Embodiment P11. An expression vector comprising the nucleic acid of embodiment P10.

Embodiment P12. The expression vector of embodiment P11, wherein said virus is a lentivirus or onco-retrovirus.

Embodiment P13. A T lymphocyte comprising the expression vector of one of embodiments P11-P12.

Embodiment P14. A T lymphocyte comprising the first recombinant protein of any one of embodiments P1-P9.

Embodiment P15. A T lymphocyte comprising the first recombinant protein of one of embodiments P1-P9, wherein said transmembrane domain is within the cell membrane of said T lymphocyte.

Embodiment P16. A method of treating cancer, said method comprising administering to a subject in need thereof an effective amount of the T-lymphocyte of embodiment P15, wherein said first antigen-binding domain and said second antigen-binding domain are independently an anti-cancer antigen-binding domain.

EMBODIMENTS

Embodiment 1. A recombinant protein comprising: (i) a non-CDR Fab binding peptide domain; (ii) an intracellular T-cell signaling domain; and (iii) a transmembrane domain connecting said non-CDR Fab binding peptide domain to said intracellular T-cell signaling domain.

Embodiment 2. The recombinant protein of embodiment 1, wherein said intracellular T-cell signaling domain is a CD3ζ intracellular T-cell signaling domain.

Embodiment 3. The recombinant protein of embodiment 1 or 2, wherein said transmembrane domain is a CD8α transmembrane domain, a CD28 transmembrane domain, a CD4 transmembrane domain or a CD3-zeta transmembrane domain.

Embodiment 4. The recombinant protein of any one of embodiments 1-3, wherein said transmembrane domain is a CD28 transmembrane domain.

Embodiment 5. The recombinant protein of any one of embodiments 1-4, further comprising a spacer region connecting said non-CDR Fab binding peptide domain to said transmembrane domain.

Embodiment 6. The recombinant protein of embodiment 5, wherein said spacer region is a constant heavy chain 3 (CH3) domain.

Embodiment 7. The recombinant protein of any one of embodiments 1-6, further comprising a peptide linker connecting said non-CDR Fab binding peptide domain to said spacer region.

Embodiment 8. The recombinant protein of any one of embodiments 1-7, further comprising an intracellular co-stimulatory signaling domain connecting said transmembrane domain to said intracellular T-cell signaling domain.

Embodiment 9. The recombinant protein of embodiment 8, wherein said intracellular co-stimulatory signaling domain is a CD28 intracellular co-stimulatory signaling domain, a 4-1BB intracellular co-stimulatory signaling domain, a ICOS intracellular co-stimulatory signaling domain, or an OX-40 intracellular co-stimulatory signaling domain.

Embodiment 10. The recombinant protein of embodiment 8 or 9, wherein said intracellular co-stimulatory signaling domain is a CD28 intracellular co-stimulatory signaling domain.

Embodiment 11. The recombinant protein of any one of embodiments 8-10, wherein said intracellular co-stimulatory signaling domain is a 4-1BB intracellular co-stimulatory signaling domain.

Embodiment 12. The recombinant protein of any one of embodiments 1-11, further comprising a detectable domain bound to the C-terminus of said intracellular T-cell signaling domain.

Embodiment 13. The recombinant protein of embodiment 12, wherein said detectable domain is a truncated CD19 protein.

Embodiment 14. The recombinant protein of any one of embodiments 1-13, further comprising a self-cleaving peptidyl sequence connecting said intracellular T-cell signaling domain to said detectable domain.

Embodiment 15. The recombinant protein of embodiment 14, wherein said self-cleaving peptidyl linker sequence is a T2A sequence or a 2A sequence.

Embodiment 16. The recombinant protein of any one of embodiments 1-15, wherein said recombinant protein forms part of a cell.

Embodiment 17. The recombinant protein of any one of embodiments 1-16, wherein said recombinant protein forms part of a T cell.

Embodiment 18. The recombinant protein of any one of embodiments 1-17, wherein said non-CDR Fab binding peptide domain is bound to an antigen-binding domain.

Embodiment 19. The recombinant protein of embodiment 18, wherein said antigen-binding domain is a Fab, an IgG, or a bispecific antibody.

Embodiment 20. The recombinant protein of any one of embodiments 18-19, wherein said antigen-binding domain is a cetuximab meditope-enabled domain, trastuzumab meditope-enabled domain, pertuzumab meditope-enabled domain, M5A meditope-enabled domain or rituximab meditope-enabled domain.

Embodiment 21. The recombinant protein of any one of embodiments 18-20, wherein said antigen-binding domain capable of binding to a cancer antigen.

Embodiment 22. The recombinant protein of any one of embodiments 18-21, wherein said antigen-binding domain capable of binding to a cancer antigen.

Embodiment 23. The recombinant protein of embodiment 21 or 22, wherein said cancer antigen is Her2, EGFR, CD19 or CD20.

Embodiment 24. The recombinant protein of embodiment 21 or 22, wherein said cancer antigen forms part of a cell.

Embodiment 25. The recombinant protein of embodiment 24, wherein said cell is a cancer cell.

Embodiment 26. The recombinant protein of embodiment 25, wherein said cancer is a ovarian cancer, renal cell carcinoma, a B-cell malignancy, leukemia, lymphoma, breast cancer, colorectal cancer, prostate cancer, neuroblastoma, melanoma, medulloblastoma, lung cancer, osteosarcoma, glioblastoma or glioma Embodiment 27. An isolated nucleic acid encoding a recombinant protein of any one of embodiments 1 to 26.

Embodiment 28. An expression vector comprising the nucleic acid of embodiment 27.

Embodiment 29. The expression vector of embodiment 28, wherein said virus is a lentivirus or onco-retrovirus.

Embodiment 30. A T lymphocyte comprising the expression vector of one of embodiments 28-29.

Embodiment 31. A T lymphocyte comprising the recombinant protein of any one of embodiments 1-26.

Embodiment 32. A T lymphocyte comprising the recombinant protein of any one of embodiments 1-26, wherein said transmembrane domain is within the cell membrane of said T lymphocyte.

Embodiment 33. The T lymphocyte of any one of embodiments 30-32, wherein said T-lymphocyte is an autologous T-lymphocyte.

Embodiment 34. The T lymphocyte of any one of embodiments 30-32, wherein said T-lymphocyte is a heterologous T-lymphocyte.

Embodiment 35. The T lymphocyte of any one of embodiments 30-34, wherein said non-CDR Fab binding peptide domain is bound to an antigen-binding domain.

Embodiment 36. The T lymphocyte of embodiment 35, wherein said antigen-binding domain is a Fab, an IgG, or a bispecific antibody.

Embodiment 37. The T lymphocyte of embodiment 35 or 36, wherein said antigen-binding domain is bound to a cancer antigen.

Embodiment 38. The T lymphocyte of embodiment 37, wherein said cancer antigen is Her2, EGFR, CD19 or CD20.

Embodiment 39. The T lymphocyte of any one of embodiments 35-38, wherein said antigen-binding domain is a cancer antigen-binding domain.

Embodiment 40. The T lymphocyte of any one of embodiments 35-39, wherein said antigen-binding domain is a cetuximab meditope-enabled domain, trastuzumab meditope-enabled domain, pertuzumab meditope-enabled domain, M5A meditope-enabled domain or rituximab meditope-enabled domain.

Embodiment 41. A method of treating cancer, said method comprising administering to a subject in need thereof an effective amount of the T lymphocyte of any one of embodiments 30-34 and an antigen-binding domain capable of binding to said non-CDR Fab binding peptide domain, wherein said antigen-binding domain is a cancer antigen-binding domain.

Embodiment 42. The method of embodiment 41, wherein said T-lymphocyte and said antigen-binding domain are administered simultaneously or sequentially.

Embodiment 43. The method of embodiment 41 or 42, wherein said T-lymphocyte is administered at a first time point and said antigen-binding domain is administered at a second time point, wherein the first time point precedes the second time point.

Embodiment 44. The method of embodiment 41 or 42, wherein said antigen-binding domain is administered at a first time point and said T-lymphocyte is administered at a second time point, wherein the first time point precedes the second time point.

Embodiment 45. The method of embodiment 41, said method comprising: (i) prior to said administering allowing said non-CDR Fab binding peptide domain to bind said antigen-binding domain in vitro, thereby forming a T-lymphocyte-recombinant protein complex; and (ii) administering said T-lymphocyte-recombinant protein complex to said subject, thereby treating cancer in said subject.

Embodiment 46. The method of any one of embodiments 41-45, wherein said cancer is ovarian cancer, renal cell carcinoma, a B-cell malignancy, leukemia, lymphoma, breast cancer, colorectal cancer, prostate cancer, neuroblastoma, melanoma, medulloblastoma, lung cancer, osteosarcoma, glioblastoma or glioma.

Embodiment 47. The method of any one of embodiments 41-46, wherein said antigen-binding domain is a cetuximab meditope-enabled domain, trastuzumab meditope-enabled domain, pertuzumab meditope-enabled domain, M5A meditope-enabled domain or rituximab meditope-enabled domain.

Embodiment 48. The recombinant protein of any one of embodiments 1-26, wherein said recombinant protein is a first recombinant protein, said non-CDR Fab binding peptide domain is a first non-CDR Fab binding peptide domain, said intracellular T-cell signaling domain is a first intracellular T-cell signaling domain, said transmembrane domain is a first transmembrane domain, said spacer region is a first spacer region and said intracellular co-stimulatory signaling domain is a first intracellular co-stimulatory signaling domain.

Embodiment 49. The recombinant protein of embodiment 48, wherein said first recombinant protein is non-covalently bound to a second recombinant protein, said second recombinant protein comprising: (i) a second non-CDR Fab binding peptide domain; (ii) a second intracellular T-cell signaling domain; (iii) a second transmembrane domain connecting said second non-CDR Fab binding peptide domain to said second intracellular T-cell signaling domain; and (iv) a second spacer region, wherein said second spacer region connects said second non-CDR Fab binding peptide domain to said second transmembrane domain, wherein said first spacer region is non-covalently bound to said second spacer region.

Embodiment 50. The recombinant protein of embodiment 49, wherein said first spacer region and said second spacer region are a first constant heavy chain 3 (CH3) domain and a second constant heavy chain 3 (CH3) domain.

Embodiment 51. The recombinant protein of any one of embodiments 48-50, wherein said first non-CDR Fab binding peptide domain and said second non-CDR Fab binding peptide domain are chemically different.

Embodiment 52. The recombinant protein of any one of embodiments 48-50, wherein said first non-CDR Fab binding peptide domain and said second non-CDR Fab binding peptide domain are chemically the same.

Embodiment 53. The recombinant protein of any one of embodiments 48-52, wherein said first non-CDR Fab binding peptide domain is non-covalently bound to a first antigen-binding domain.

Embodiment 54. The recombinant protein of any one of embodiments 49-53, wherein said second non-CDR Fab binding peptide domain is non-covalently bound to a second antigen-binding domain.

Embodiment 55. The recombinant protein of embodiment 53 or 54, wherein said first antigen-binding domain and said second antigen-binding domain are chemically different or the same.

Embodiment 56. The recombinant protein of any one of embodiments 53-55, wherein said first antigen-binding domain and said second antigen-binding domain are independently a cetuximab meditope-enabled domain, trastuzumab meditope-enabled domain, pertuzumab meditope-enabled domain, M5A meditope-enabled domain or rituximab meditope-enabled domain.

---

INFORMAL SEQUENCE LISTING

CD3z; GI:623041 (SEQ ID NO: 1)
LCYLLDGILFIYGVILTALFL

CD28; GI:340545506 (SEQ ID NO: 2)
FWVLVVVGGVLACYSLLVTVAFIIFWV

CD4; GI:179143 (SEQ ID NO: 3)
MALIVLGGVAGLLLFIGLGIFF

CD8; GI:225007534 (SEQ ID NO: 4)
IYIWAPLAGTCGVLLLSLVIT

-continued

---

INFORMAL SEQUENCE LISTING

---

CD8; GI:225007534 (SEQ ID NO: 5)
IYIWAPLAGTCGVLLLSLVITLY

CD8; GI:225007534 (SEQ ID NO: 6)
IYIWAPLAGTCGVLLLSLVITLYC

41BB; GI:315259099 (SEQ ID NO: 7)
IISFFLALTSTALLFLLFFLTLRFSVV

OX40; GI:315360637 (SEQ ID NO: 8)
VAAILGLGLVLGLLGPLAILL

ICOS; GI:251823951 (SEQ ID NO: 9)
FWLPIGCAAFVVVCILGCILI

CD62L; GI:262206314 (SEQ ID NO: 10)
PLFIPVAVMVTAFSGLAFIIWLA

CD3ζ; GI:623041; SEQ ID NO: 11:
RVKFSRSADAPAYQQGQNQLYNELNLGRREEYDVLDKRRGRDPEMGGKPQRRKNP
QEGLY

CD28; GI:340545506; SEQ ID NO: 12:
RSKRSRLLHSDYMNMTPRRPGPTRKHYQPYAPPRDFAAYRS

CD28gg*; GI:340545506; SEQ ID NO: 13:
RSKRSRGGHSDYMNMTPRRPGPTRKHYQPYAPPRDFAAYRS (ref)

41BB; GI:315259099; SEQ ID NO: 14:
KRGRKKLLYIFKQPFMRPVQTTQEEDGCSCRFPEEEEGGCEL

OX40; GI:315360637; SEQ ID NO: 15:
ALYLLRRDQRLPPDAHKPPGGGSFRTPIQEEQADAHSTLAKI

ICOS; GI:251823951; SEQ ID NO: 16:
CWLTKKKYSSSVHDPNGEYMFMRAVNTAKKSRLTDVTL

Spacer (including IgG4-CH3) SEQ ID NO: 17:
GGGSSGGGSGGQPREPQVYTLPPSQEEMTKNQVSLTCLVKGFYPSDIAVEWESNGQP
ENNYKTTPPVLDSDGSFFLYSRLTVDKSRWQEGNVFSCSVMHEALHNHYTQKSLSL
SLGK CD28 transmembrane SEQ ID NO: 18:
MFWVLVVVGGVLACYSLLVTVAFIIFWV CD28cyto (LLmGG) SEQ ID NO: 19:
RSKRSRGGHSDYMNMTPRRPGPTRKHYQPYAPPRDFAAYRS Intracellular T-cell signaling domain (CD3-Zeta) SEQ ID NO: 20:
RVKFSRSADAPAYQQGQNQLYNELNLGRREEYDVLDKRRGRDPEMGGKPRRKNPQ
EGLYNELQKDKMAEAYSEIGMKGERRRGKGHDGLYQGLSTATKDTYDALHMQAL
PPR Self-cleaving peptidyl linker (T2A) SEQ ID NO: 21:
LEGGGEGRGSLLTCGDVEENPGPTR Marker peptide (CD19t) SEQ ID NO: 22:
MPPPRLLFFLLFLTPMEVRPEEPLVVKVEEGDNAVLQCLKGTSDGPTQQLTWSRESP
LKPFLKLSLGLPGLGIHMRPLAIWLFIFNVSQQMGGFYLCQPGPPSEKAWQPGWTVN
VEGSGELFRWNVSDLGGLGCGLKNRSSEGPSSPSGKLMSPKLYVWAKDRPEIWEGE
PPCVPPRDSLNQSLSQDLTMAPGSTLWLSCGVPPDSVSRGPLSWTHVHPKGPKSLLS
LELKDDRPARDMWVMETGLLLPRATAQDAGKYYCHRGNLTMSFHLEITARPVLWH
WLLRTGGWKVSAVTLAYLIFCLCSLVGILHLQRALVLRRKR Self-cleaving peptidyl linker (2A) SEQ ID NO: 23:
GGSTSEGRGSLLTCGDVEENPGP Spacer region SEQ ID NO: 24
GSGSGSGS Peptide linker SEQ ID NO: 25
SAPASSASAPSAASAPAG

SEQ ID NO: 26
SAPASSASAPSAASAPAG

---

INFORMAL SEQUENCE LISTING

--- self-cleaving peptidyl linker SEQ ID NO: 27
PVKQLLNFDLLKLAGDVESNPGP self-cleaving peptidyl linker SEQ ID NO: 28
QCTNYALLKLAGDVESNPGP self-cleaving peptidyl linker SEQ ID NO: 29
ATNFSLLKQAGDVEENPGP self-cleaving peptidyl linker SEQ ID NO: 30
EGRGSLLTCGDVESNPGP Spacer region SEQ ID NO: 31
GGGSSGGGSG SEQ ID NO: 32; Meditope (non-CDR Fab binding peptide domain)
CQFDLSTRRLQC SEQ ID NO: 33; CH3 (spacer region)
QPREPQVYTLPPSQEEMTKNQVSLTCLVKGFYPSDIAVEWESNGQPENNYKTTPPVL
DSDGSFFLYSRLTVDKSRWQEGNVFSCSVMHEALHNHYTQKSLSLSLGK SEQ ID NO: 34; CD3 zeta chain (intracellular T-cell signaling domain)
RVKFSRSADAPAYQQGQNQLYNELNLGRREEYDVLDKRRGRDPEMGGKPRRKNPQ
EGLYNELQKDKMAEAYSEIGMKGERRRGKGHDGLYQGLSTATKDTYDALHMQAL
PPR SEQ ID NO: 35; entire 4-1BB Fabrack sequence
MLLLVTSLLLCELPHPAFLLIPCQFDLSTRRLQCSAPASSASAPSAASAPAGGQPREPQ
VYTLPPSQEEMTKNQVSLTCLVKGFYPSDIAVEWESNGQPENNYKTTPPVLDSDGSF
FLYSRLTVDKSRWQEGNVFSCSVMHEALHNHYTQKSLSLSLGKMFWVLVVVGGVL
ACYSLLVTVAFIIFWVKRGRKKLLYIFKQPFMRPVQTTQEEDGCSCRFPEEEEGGCEL
GGGRVKFSRSADAPAYQQGQNQLYNELNLGRREEYDVLDKRRGRDPEMGGKPRRK
NPQEGLYNELQKDKMAEAYSEIGMKGERRRGKGHDGLYQGLSTATKDTYDALHM
QALPPRLEGGGEGRGSLLTCGDVEENPGPTRMPPPRLLFFLLFLTPMEVRPEEPLVVK
VEEGDNAVLQCLKGTSDGPTQQLTWSRESPLKPFLKLSLGLPGLGIHMRPLAIWLFIF
NVSQQMGGFYLCQPGPPSEKAWQPGWTVNVEGSGELFRWNVSDLGGLGCGLKNRS
SEGPSSPSGKLMSPKLYVWAKDRPEIWEGEPPCVPPRDSLNQSLSQDLTMAPGSTLW
LSCGVPPDSVSRGPLSWTHVHPKGPKSLLSLELKDDRPARDMWVMETGLLLPRATA
QDAGKYYCHRGNLTMSFHLEITARPVLWHWLLRTGGWKVSAVTLAYLIFCLCSLV
GILHLQRALVLRRKR SEQ ID NO: 36; entire CD28 Fabrack sequence
MLLLVTSLLLCELPHPAFLLIPCQFDLSTRRLQCSAPASSASAPSAASAPAGGQPREPQ
VYTLPPSQEEMTKNQVSLTCLVKGFYPSDIAVEWESNGQPENNYKTTPPVLDSDGSF
FLYSRLTVDKSRWQEGNVFSCSVMHEALHNHYTQKSLSLSLGKMFWVLVVVGGVL
ACYSLLVTVAFIIFWVRSKRSRGGHSDYMNMTPRRPGPTRKHYQPYAPPRDFAAYRS
GGGRVKFSRSADAPAYQQGQNQLYNELNLGRREEYDVLDKRRGRDPEMGGKPRRK
NPQEGLYNELQKDKMAEAYSEIGMKGERRRGKGHDGLYQGLSTATKDTYDALHM
QALPPRLEGGGEGRGSLLTCGDVEENPGPRMPPPRLLFFLLFLTPMEVRPEEPLVVKV
EEGDNAVLQCLKGTSDGPTQQLTWSRESPLKPFLKLSLGLPGLGIHMRPLAIWLFIFN
VSQQMGGFYLCQPGPPSEKAWQPGWTVNVEGSGELFRWNVSDLGGLGCGLKNRSS
EGPSSPSGKLMSPKLYVWAKDRPEIWEGEPPCVPPRDSLNQSLSQDLTMAPGSTLWL
SCGVPPDSVSRGPLSWTHVHPKGPKSLLSLELKDDRPARDMWVMETGLLLPRATAQ
DAGKYYCHRGNLTMSFHLEITARPVLWHWLLRTGGWKVSAVTLAYLIFCLCSLVGI
LHLQRALVLRRKR SEQ ID NO: 37; signal peptide
MLLLVTSLLLCELPHPAFLLIP

---

SEQUENCE LISTING

---

<160> NUMBER OF SEQ ID NOS: 37

<210> SEQ ID NO 1
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 1

```
Leu Cys Tyr Leu Leu Asp Gly Ile Leu Phe Ile Tyr Gly Val Ile Leu
1               5                   10                  15

Thr Ala Leu Phe Leu
            20

<210> SEQ ID NO 2
<211> LENGTH: 27
<212> TYPE: PRT
<213> ORGANISM: Artificial sequence
<220> FEATURE:
<223> OTHER INFORMATION: Synthetic polypeptide

<400> SEQUENCE: 2

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 3
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 3

Met Ala Leu Ile Val Leu Gly Gly Val Ala Gly Leu Leu Leu Phe Ile
1               5                   10                  15

Gly Leu Gly Ile Phe Phe
            20

<210> SEQ ID NO 4
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 4

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 5
<211> LENGTH: 23
<212> TYPE: PRT
<213> ORGANISM: Artificial sequence
<220> FEATURE:
<223> OTHER INFORMATION: Synthetic polypeptide

<400> SEQUENCE: 5

Ile Tyr Ile Trp Ala Pro Leu Ala Gly Thr Cys Gly Val Leu Leu Leu
1               5                   10                  15

Ser Leu Val Ile Thr Leu Tyr
            20

<210> SEQ ID NO 6
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 6
```

```
Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 7
<211> LENGTH: 27
<212> TYPE: PRT
<213> ORGANISM: Artificial sequence
<220> FEATURE:
<223> OTHER INFORMATION: Synthetic polypeptide

<400> SEQUENCE: 7

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 8
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 8

Val Ala Ala Ile Leu Gly Leu Gly Leu Val Leu Gly Leu Leu Gly Pro
1               5                   10                  15

Leu Ala Ile Leu Leu
            20

<210> SEQ ID NO 9
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 9

Phe Trp Leu Pro Ile Gly Cys Ala Ala Phe Val Val Val Cys Ile Leu
1               5                   10                  15

Gly Cys Ile Leu Ile
            20

<210> SEQ ID NO 10
<211> LENGTH: 23
<212> TYPE: PRT
<213> ORGANISM: Artificial sequence
<220> FEATURE:
<223> OTHER INFORMATION: Synthetic polypeptide

<400> SEQUENCE: 10

Pro Leu Phe Ile Pro Val Ala Val Met Val Thr Ala Phe Ser Gly Leu
1               5                   10                  15

Ala Phe Ile Ile Trp Leu Ala
            20

<210> SEQ ID NO 11
<211> LENGTH: 60
<212> TYPE: PRT
<213> ORGANISM: Artificial sequence
<220> FEATURE:
<223> OTHER INFORMATION: Synthetic polypeptide
```

-continued

```
<400> SEQUENCE: 11

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Gln Arg Arg Lys Asn Pro Gln Glu Gly Leu Tyr
        50                  55                  60

<210> SEQ ID NO 12
<211> LENGTH: 41
<212> TYPE: PRT
<213> ORGANISM: Artificial sequence
<220> FEATURE:
<223> OTHER INFORMATION: Synthetic polypeptide

<400> SEQUENCE: 12

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
        35                  40

<210> SEQ ID NO 13
<211> LENGTH: 41
<212> TYPE: PRT
<213> ORGANISM: Artificial sequence
<220> FEATURE:
<223> OTHER INFORMATION: Synthetic polypeptide

<400> SEQUENCE: 13

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
        35                  40

<210> SEQ ID NO 14
<211> LENGTH: 42
<212> TYPE: PRT
<213> ORGANISM: Artificial sequence
<220> FEATURE:
<223> OTHER INFORMATION: Synthetic polypeptide

<400> SEQUENCE: 14

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
        35                  40

<210> SEQ ID NO 15
<211> LENGTH: 42
<212> TYPE: PRT
<213> ORGANISM: Artificial sequence
<220> FEATURE:
<223> OTHER INFORMATION: Synthetic polypeptide
```

```
<400> SEQUENCE: 15

Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
            20                  25                  30

Ala Asp Ala His Ser Thr Leu Ala Lys Ile
        35                  40

<210> SEQ ID NO 16
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 16

Cys Trp Leu Thr Lys Lys Lys Tyr Ser Ser Ser Val His Asp Pro Asn
1               5                   10                  15

Gly Glu Tyr Met Phe Met Arg Ala Val Asn Thr Ala Lys Lys Ser Arg
            20                  25                  30

Leu Thr Asp Val Thr Leu
        35

<210> SEQ ID NO 17
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 17

Gly Gly Gly Ser Ser Gly Gly Gly Ser Gly Gly Gln Pro Arg Glu Pro
1               5                   10                  15

Gln Val Tyr Thr Leu Pro Pro Ser Gln Glu Glu Met Thr Lys Asn Gln
            20                  25                  30

Val Ser Leu Thr Cys Leu Val Lys Gly Phe Tyr Pro Ser Asp Ile Ala
        35                  40                  45

Val Glu Trp Glu Ser Asn Gly Gln Pro Glu Asn Asn Tyr Lys Thr Thr
    50                  55                  60

Pro Pro Val Leu Asp Ser Asp Gly Ser Phe Phe Leu Tyr Ser Arg Leu
65                  70                  75                  80

Thr Val Asp Lys Ser Arg Trp Gln Glu Gly Asn Val Phe Ser Cys Ser
                85                  90                  95

Val Met His Glu Ala Leu His Asn His Tyr Thr Gln Lys Ser Leu Ser
            100                 105                 110

Leu Ser Leu Gly Lys
        115

<210> SEQ ID NO 18
<211> LENGTH: 28
<212> TYPE: PRT
<213> ORGANISM: Artificial sequence
<220> FEATURE:
<223> OTHER INFORMATION: Synthetic polypeptide

<400> SEQUENCE: 18

Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25
```

```
<210> SEQ ID NO 19
<211> LENGTH: 41
<212> TYPE: PRT
<213> ORGANISM: Artificial sequence
<220> FEATURE:
<223> OTHER INFORMATION: Synthetic polypeptide

<400> SEQUENCE: 19

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 20
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 20

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 21
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 21

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 22
<211> LENGTH: 323
<212> TYPE: PRT
<213> ORGANISM: Artificial sequence
<220> FEATURE:
<223> OTHER INFORMATION: Synthetic polypeptide

<400> SEQUENCE: 22

Met Pro Pro Pro Arg Leu Leu Phe Phe Leu Leu Phe Leu Thr Pro Met
1               5                   10                  15
```

```
Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
            35                  40                  45

Gln Leu Thr Trp Ser Arg Glu Ser Pro Leu Lys Pro Phe Leu Lys Leu
        50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
            115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Val Pro Pro
            165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
            195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
            245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
            275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg

<210> SEQ ID NO 23
<211> LENGTH: 23
<212> TYPE: PRT
<213> ORGANISM: Artificial sequence
<220> FEATURE:
<223> OTHER INFORMATION: Synthetic polypeptide

<400> SEQUENCE: 23

Gly Gly Ser Thr Ser Glu Gly Arg Gly Ser Leu Leu Thr Cys Gly Asp
1               5                   10                  15

Val Glu Glu Asn Pro Gly Pro
            20

<210> SEQ ID NO 24
<211> LENGTH: 8
```

```
<212> TYPE: PRT
<213> ORGANISM: Artificial sequence
<220> FEATURE:
<223> OTHER INFORMATION: Synthetic polypeptide

<400> SEQUENCE: 24

Gly Ser Gly Ser Gly Ser Gly Ser
1               5

<210> SEQ ID NO 25
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 25

Ser Ala Pro Ala Ser Ser Ala Ser Ala Pro Ser Ala Ala Ser Ala Pro
1               5                   10                  15

Ala Gly

<210> SEQ ID NO 26
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 26

Ser Ala Pro Ala Ser Ser Ala Ser Ala Pro Ser Ala Ala Ser Ala Pro
1               5                   10                  15

Ala Gly

<210> SEQ ID NO 27
<211> LENGTH: 23
<212> TYPE: PRT
<213> ORGANISM: Artificial sequence
<220> FEATURE:
<223> OTHER INFORMATION: Synthetic polypeptide

<400> SEQUENCE: 27

Pro Val Lys Gln Leu Leu Asn Phe Asp Leu Leu Lys Leu Ala Gly Asp
1               5                   10                  15

Val Glu Ser Asn Pro Gly Pro
            20

<210> SEQ ID NO 28
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 28

Gln Cys Thr Asn Tyr Ala Leu Leu Lys Leu Ala Gly Asp Val Glu Ser
1               5                   10                  15

Asn Pro Gly Pro
            20

<210> SEQ ID NO 29
<211> LENGTH: 19
<212> TYPE: PRT
<213> ORGANISM: Artificial sequence
<220> FEATURE:
<223> OTHER INFORMATION: Synthetic polypeptide
```

<400> SEQUENCE: 29

Ala Thr Asn Phe Ser Leu Leu Lys Gln Ala Gly Asp Val Glu Glu Asn
1               5                   10                  15

Pro Gly Pro

<210> SEQ ID NO 30
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 30

Glu Gly Arg Gly Ser Leu Leu Thr Cys Gly Asp Val Glu Ser Asn Pro
1               5                   10                  15

Gly Pro

<210> SEQ ID NO 31
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 31

Gly Gly Gly Ser Ser Gly Gly Gly Ser Gly
1               5                   10

<210> SEQ ID NO 32
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 32

Cys Gln Phe Asp Leu Ser Thr Arg Arg Leu Gln Cys
1               5                   10

<210> SEQ ID NO 33
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 33

Gln Pro Arg Glu Pro Gln Val Tyr Thr Leu Pro Pro Ser Gln Glu Glu
1               5                   10                  15

Met Thr Lys Asn Gln Val Ser Leu Thr Cys Leu Val Lys Gly Phe Tyr
            20                  25                  30

Pro Ser Asp Ile Ala Val Glu Trp Glu Ser Asn Gly Gln Pro Glu Asn
        35                  40                  45

Asn Tyr Lys Thr Thr Pro Pro Val Leu Asp Ser Asp Gly Ser Phe Phe
    50                  55                  60

Leu Tyr Ser Arg Leu Thr Val Asp Lys Ser Arg Trp Gln Glu Gly Asn
65                  70                  75                  80

Val Phe Ser Cys Ser Val Met His Glu Ala Leu His Asn His Tyr Thr
                85                  90                  95

Gln Lys Ser Leu Ser Leu Ser Leu Gly Lys
            100                 105

-continued

```
<210> SEQ ID NO 34
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 34

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 35
<211> LENGTH: 692
<212> TYPE: PRT
<213> ORGANISM: Artificial sequence
<220> FEATURE:
<223> OTHER INFORMATION: Synthetic polypeptide

<400> SEQUENCE: 35

Met Leu Leu Leu Val Thr Ser Leu Leu Leu Cys Glu Leu Pro His Pro
1               5                   10                  15

Ala Phe Leu Leu Ile Pro Cys Gln Phe Asp Leu Ser Thr Arg Arg Leu
                20                  25                  30

Gln Cys Ser Ala Pro Ala Ser Ser Ala Ser Ala Pro Ser Ala Ala Ser
            35                  40                  45

Ala Pro Ala Gly Gly Gln Pro Arg Glu Pro Gln Val Tyr Thr Leu Pro
        50                  55                  60

Pro Ser Gln Glu Glu Met Thr Lys Asn Gln Val Ser Leu Thr Cys Leu
65                  70                  75                  80

Val Lys Gly Phe Tyr Pro Ser Asp Ile Ala Val Glu Trp Glu Ser Asn
                85                  90                  95

Gly Gln Pro Glu Asn Asn Tyr Lys Thr Thr Pro Pro Val Leu Asp Ser
                100                 105                 110

Asp Gly Ser Phe Phe Leu Tyr Ser Arg Leu Thr Val Asp Lys Ser Arg
            115                 120                 125

Trp Gln Glu Gly Asn Val Phe Ser Cys Ser Val Met His Glu Ala Leu
        130                 135                 140

His Asn His Tyr Thr Gln Lys Ser Leu Ser Leu Ser Leu Gly Lys Met
145                 150                 155                 160

Phe Trp Val Leu Val Val Val Gly Gly Val Leu Ala Cys Tyr Ser Leu
                165                 170                 175

Leu Val Thr Val Ala Phe Ile Ile Phe Trp Val Lys Arg Gly Arg Lys
                180                 185                 190

Lys Leu Leu Tyr Ile Phe Lys Gln Pro Phe Met Arg Pro Val Gln Thr
```

-continued

```
                195                 200                 205

Thr Gln Glu Glu Asp Gly Cys Ser Cys Arg Phe Pro Glu Glu Glu Glu
    210                 215                 220

Gly Gly Cys Glu Leu Gly Gly Gly Arg Val Lys Phe Ser Arg Ser Ala
225                 230                 235                 240

Asp Ala Pro Ala Tyr Gln Gln Gly Gln Asn Gln Leu Tyr Asn Glu Leu
                245                 250                 255

Asn Leu Gly Arg Arg Glu Glu Tyr Asp Val Leu Asp Lys Arg Arg Gly
                260                 265                 270

Arg Asp Pro Glu Met Gly Gly Lys Pro Arg Arg Lys Asn Pro Gln Glu
                275                 280                 285

Gly Leu Tyr Asn Glu Leu Gln Lys Asp Lys Met Ala Glu Ala Tyr Ser
                290                 295                 300

Glu Ile Gly Met Lys Gly Glu Arg Arg Arg Gly Lys Gly His Asp Gly
305                 310                 315                 320

Leu Tyr Gln Gly Leu Ser Thr Ala Thr Lys Asp Thr Tyr Asp Ala Leu
                325                 330                 335

His Met Gln Ala Leu Pro Pro Arg Leu Glu Gly Gly Gly Glu Gly Arg
                340                 345                 350

Gly Ser Leu Leu Thr Cys Gly Asp Val Glu Glu Asn Pro Gly Pro Thr
                355                 360                 365

Arg Met Pro Pro Pro Arg Leu Leu Phe Phe Leu Leu Phe Leu Thr Pro
370                 375                 380

Met Glu Val Arg Pro Glu Glu Pro Leu Val Val Lys Val Glu Glu Gly
385                 390                 395                 400

Asp Asn Ala Val Leu Gln Cys Leu Lys Gly Thr Ser Asp Gly Pro Thr
                405                 410                 415

Gln Gln Leu Thr Trp Ser Arg Glu Ser Pro Leu Lys Pro Phe Leu Lys
                420                 425                 430

Leu Ser Leu Gly Leu Pro Gly Leu Gly Ile His Met Arg Pro Leu Ala
                435                 440                 445

Ile Trp Leu Phe Ile Phe Asn Val Ser Gln Gln Met Gly Gly Phe Tyr
                450                 455                 460

Leu Cys Gln Pro Gly Pro Pro Ser Glu Lys Ala Trp Gln Pro Gly Trp
465                 470                 475                 480

Thr Val Asn Val Glu Gly Ser Gly Glu Leu Phe Arg Trp Asn Val Ser
                485                 490                 495

Asp Leu Gly Gly Leu Gly Cys Gly Leu Lys Asn Arg Ser Ser Glu Gly
                500                 505                 510

Pro Ser Ser Pro Ser Gly Lys Leu Met Ser Pro Lys Leu Tyr Val Trp
                515                 520                 525

Ala Lys Asp Arg Pro Glu Ile Trp Glu Gly Glu Pro Pro Cys Val Pro
                530                 535                 540

Pro Arg Asp Ser Leu Asn Gln Ser Leu Ser Gln Asp Leu Thr Met Ala
545                 550                 555                 560

Pro Gly Ser Thr Leu Trp Leu Ser Cys Gly Val Pro Pro Asp Ser Val
                565                 570                 575

Ser Arg Gly Pro Leu Ser Trp Thr His Val His Pro Lys Gly Pro Lys
                580                 585                 590

Ser Leu Leu Ser Leu Glu Leu Lys Asp Asp Arg Pro Ala Arg Asp Met
                595                 600                 605

Trp Val Met Glu Thr Gly Leu Leu Leu Pro Arg Ala Thr Ala Gln Asp
                610                 615                 620
```

-continued

Ala Gly Lys Tyr Tyr Cys His Arg Gly Asn Leu Thr Met Ser Phe His
625                 630                 635                 640

Leu Glu Ile Thr Ala Arg Pro Val Leu Trp His Trp Leu Leu Arg Thr
                    645                 650                 655

Gly Gly Trp Lys Val Ser Ala Val Thr Leu Ala Tyr Leu Ile Phe Cys
                660                 665                 670

Leu Cys Ser Leu Val Gly Ile Leu His Leu Gln Arg Ala Leu Val Leu
                675                 680                 685

Arg Arg Lys Arg
                690

<210> SEQ ID NO 36
<211> LENGTH: 690
<212> TYPE: PRT
<213> ORGANISM: Artificial sequence
<220> FEATURE:
<223> OTHER INFORMATION: Synthetic polypeptide

<400> SEQUENCE: 36

Met Leu Leu Leu Val Thr Ser Leu Leu Leu Cys Glu Leu Pro His Pro
1                   5                   10                  15

Ala Phe Leu Leu Ile Pro Cys Gln Phe Asp Leu Ser Thr Arg Arg Leu
                    20                  25                  30

Gln Cys Ser Ala Pro Ala Ser Ser Ala Ser Ala Pro Ser Ala Ala Ser
                35                  40                  45

Ala Pro Ala Gly Gly Gln Pro Arg Glu Pro Gln Val Tyr Thr Leu Pro
                50                  55                  60

Pro Ser Gln Glu Glu Met Thr Lys Asn Gln Val Ser Leu Thr Cys Leu
65                  70                  75                  80

Val Lys Gly Phe Tyr Pro Ser Asp Ile Ala Val Glu Trp Glu Ser Asn
                85                  90                  95

Gly Gln Pro Glu Asn Asn Tyr Lys Thr Thr Pro Pro Val Leu Asp Ser
                100                 105                 110

Asp Gly Ser Phe Phe Leu Tyr Ser Arg Leu Thr Val Asp Lys Ser Arg
                115                 120                 125

Trp Gln Glu Gly Asn Val Phe Ser Cys Ser Val Met His Glu Ala Leu
                130                 135                 140

His Asn His Tyr Thr Gln Lys Ser Leu Ser Leu Ser Leu Gly Lys Met
145                 150                 155                 160

Phe Trp Val Leu Val Val Val Gly Gly Val Leu Ala Cys Tyr Ser Leu
                    165                 170                 175

Leu Val Thr Val Ala Phe Ile Ile Phe Trp Val Arg Ser Lys Arg Ser
                    180                 185                 190

Arg Gly Gly His Ser Asp Tyr Met Asn Met Thr Pro Arg Arg Pro Gly
                195                 200                 205

Pro Thr Arg Lys His Tyr Gln Pro Tyr Ala Pro Pro Arg Asp Phe Ala
                210                 215                 220

Ala Tyr Arg Ser Gly Gly Gly Arg Val Lys Phe Ser Arg Ser Ala Asp
225                 230                 235                 240

Ala Pro Ala Tyr Gln Gln Gly Gln Asn Gln Leu Tyr Asn Glu Leu Asn
                245                 250                 255

Leu Gly Arg Arg Glu Glu Tyr Asp Val Leu Asp Lys Arg Arg Gly Arg
                260                 265                 270

Asp Pro Glu Met Gly Gly Lys Pro Arg Arg Lys Asn Pro Gln Glu Gly
                275                 280                 285

-continued

```
Leu Tyr Asn Glu Leu Gln Lys Asp Lys Met Ala Glu Ala Tyr Ser Glu
    290                 295                 300

Ile Gly Met Lys Gly Glu Arg Arg Arg Gly Lys Gly His Asp Gly Leu
305                 310                 315                 320

Tyr Gln Gly Leu Ser Thr Ala Thr Lys Asp Thr Tyr Asp Ala Leu His
                325                 330                 335

Met Gln Ala Leu Pro Pro Arg Leu Glu Gly Gly Gly Glu Gly Arg Gly
                340                 345                 350

Ser Leu Leu Thr Cys Gly Asp Val Glu Glu Asn Pro Gly Pro Arg Met
                355                 360                 365

Pro Pro Pro Arg Leu Leu Phe Phe Leu Leu Phe Leu Thr Pro Met Glu
    370                 375                 380

Val Arg Pro Glu Glu Pro Leu Val Val Lys Val Glu Glu Gly Asp Asn
385                 390                 395                 400

Ala Val Leu Gln Cys Leu Lys Gly Thr Ser Asp Gly Pro Thr Gln Gln
                405                 410                 415

Leu Thr Trp Ser Arg Glu Ser Pro Leu Lys Pro Phe Leu Lys Leu Ser
                420                 425                 430

Leu Gly Leu Pro Gly Leu Gly Ile His Met Arg Pro Leu Ala Ile Trp
                435                 440                 445

Leu Phe Ile Phe Asn Val Ser Gln Gln Met Gly Gly Phe Tyr Leu Cys
    450                 455                 460

Gln Pro Gly Pro Pro Ser Glu Lys Ala Trp Gln Pro Gly Trp Thr Val
465                 470                 475                 480

Asn Val Glu Gly Ser Gly Glu Leu Phe Arg Trp Asn Val Ser Asp Leu
                485                 490                 495

Gly Gly Leu Gly Cys Gly Leu Lys Asn Arg Ser Ser Glu Gly Pro Ser
                500                 505                 510

Ser Pro Ser Gly Lys Leu Met Ser Pro Lys Leu Tyr Val Trp Ala Lys
                515                 520                 525

Asp Arg Pro Glu Ile Trp Glu Gly Glu Pro Pro Cys Val Pro Pro Arg
    530                 535                 540

Asp Ser Leu Asn Gln Ser Leu Ser Gln Asp Leu Thr Met Ala Pro Gly
545                 550                 555                 560

Ser Thr Leu Trp Leu Ser Cys Gly Val Pro Pro Asp Ser Val Ser Arg
                565                 570                 575

Gly Pro Leu Ser Trp Thr His Val His Pro Lys Gly Pro Lys Ser Leu
                580                 585                 590

Leu Ser Leu Glu Leu Lys Asp Asp Arg Pro Ala Arg Asp Met Trp Val
                595                 600                 605

Met Glu Thr Gly Leu Leu Leu Pro Arg Ala Thr Ala Gln Asp Ala Gly
    610                 615                 620

Lys Tyr Tyr Cys His Arg Gly Asn Leu Thr Met Ser Phe His Leu Glu
625                 630                 635                 640

Ile Thr Ala Arg Pro Val Leu Trp His Trp Leu Leu Arg Thr Gly Gly
                645                 650                 655

Trp Lys Val Ser Ala Val Thr Leu Ala Tyr Leu Ile Phe Cys Leu Cys
                660                 665                 670

Ser Leu Val Gly Ile Leu His Leu Gln Arg Ala Leu Val Leu Arg Arg
                675                 680                 685

Lys Arg
    690
```

-continued

```
<210> SEQ ID NO 37
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 37

Met Leu Leu Leu Val Thr Ser Leu Leu Leu Cys Glu Leu Pro His Pro
1               5                   10                  15

Ala Phe Leu Leu Ile Pro
            20
```

What is claimed:

1. A recombinant protein comprising:
   (i) a meditope capable of binding a meditope-enabled Fab;
   (ii) an intracellular T-cell signaling domain; and
   (iii) a transmembrane domain connecting said meditope to said intracellular T-cell signaling domain; wherein said recombinant protein does not comprise an antigen binding domain.

2. The recombinant protein of claim 1, further comprising a spacer region connecting said meditope to said transmembrane domain.

3. The recombinant protein of claim 2, wherein said spacer region is a constant heavy chain 3 (CH3) domain.

4. The recombinant protein of claim 3, further comprising a peptide linker connecting said meditope to said spacer region.

5. The recombinant protein of claim 1, further comprising a detectable domain bound to the C-terminus of said intracellular T-cell signaling domain.

6. The recombinant protein of claim 5, further comprising a self-cleaving peptidyl sequence connecting said intracellular T-cell signaling domain to said detectable domain.

7. An isolated nucleic acid encoding a recombinant protein of claim 1.

8. An expression vector comprising the nucleic acid of claim 7.

9. A T lymphocyte comprising the expression vector of claim 8.

10. A T lymphocyte comprising the recombinant protein of claim 1.

11. A method of treating cancer, said method comprising administering to a subject in need thereof an effective amount of the T lymphocyte of claim 9 and an antigen-binding domain capable of binding to said meditope, wherein said antigen-binding domain is a cetuximab meditope-enabled domain, trastuzumab meditope-enabled domain, pertuzumab meditope-enabled domain, M5A meditope-enabled domain or rituximab meditope-enabled domain.

12. The method of claim 11, wherein said T-lymphocyte and said antigen-binding domain are administered simultaneously or sequentially.

13. The method of claim 11, said method comprising:
   (i) prior to said administering allowing said meditope to bind said antigen-binding domain in vitro, thereby forming a T-lymphocyte-recombinant protein complex; and
   (ii) administering said T-lymphocyte-recombinant protein complex to said subject, thereby treating cancer in said subject.

14. The recombinant protein of claim 2, wherein said recombinant protein is a first recombinant protein, said meditope is a first meditope, said intracellular T-cell signaling domain is a first intracellular T-cell signaling domain, said transmembrane domain is a first transmembrane domain and said spacer region is a first spacer region.

15. The recombinant protein of claim 14, wherein said first recombinant protein is non-covalently bound to a second recombinant protein, said second recombinant protein comprising:
   (i) a second meditope;
   (ii) a second intracellular T-cell signaling domain;
   (iii) a second transmembrane domain connecting said meditope to said second intracellular T-cell signaling domain; and
   (iv) a second spacer region, wherein said second spacer region connects said second meditope to said second transmembrane domain, wherein said first spacer region is non-covalently bound to said second spacer region; wherein said second recombinant protein does not comprise an antigen binding domain.

16. The recombinant protein of claim 15, wherein said first meditope and said second meditope are chemically different or chemically the same.

17. The recombinant protein of claim 1, wherein said meditope has the formula:

$$X0\text{-}X1\text{-}X2\text{-}X3\text{-}X4\text{-}X5\text{-}X6\text{-}X7\text{-}X8\text{-}X9\text{-}X10\text{-}X11\text{-}X12 \tag{I},$$

wherein

X0 is Ser or null;

X1 is Ser, Cys, Gly, β-alanine, diaminopropionic acid, β-azidoalanine, or null;

X2 is Gln or null, X3 is Phe, Tyr, β,β'-diphenyl-Ala, His, Asp, 2-bromo-L-phenylalanine, 3-bromo-L-phenylalanine, 4-bromo-L-phenylalanine, Asn, Gln, a modified Phe, a hydratable carbonyl-containing residue, or a boronic acid-containing residue;

X4 is Asp or Asn;

X5 is Leu, β,β'-diphenyl-Ala, Phe, Trp, Tyr, a non-natural analog of phenylalanine, tryptophan, or tyrosine, a hydratable carbonyl-containing residue, or a boronic acid-containing residue;

X6 is Cys or Ser;

X7 is Cys, Thr, or Ser;

X8 is protected Arg, Arg, or Ala;

X9 is Cys, Arg or Ala;

X10 is Leu, Gln, Glu, β,β'-diphenyl-Ala, Phe, Trp, Tyr, a non-natural analog of phenylalanine, tryptophan, or tyrosine, a hydratable carbonyl-containing residue, or a boronic acid-containing residue;

X11 is Cys, Gln, Lys or Arg;

X12 is Ser, Cys, Gly, 7-aminoheptanoic acid, β-alanine, diaminopropionic acid, propargylglycine, isoaspartic acid, or null; and X1 and X12 are optionally joined together to form a cyclic peptidyl moiety.

18. The recombinant protein of claim 17, wherein the VL region of said meditope-enabled Fab comprises a threonine at position 40, an asparagine at position 41, and an aspartate at position 85, according to Kabat numbering, and the VH region of said meditope-enabled Fab comprises a serine or proline at position 40 and an isoleucine, tyrosine, methionine, phenylalanine, or a tryptophan at position 89, according to Kabat numbering.

\* \* \* \* \*